(12) United States Patent
Shindo

(10) Patent No.: US 9,072,777 B2
(45) Date of Patent: Jul. 7, 2015

(54) METHOD FOR SCREENING SUBSTANCE HAVING PROANGIOGENIC EFFECT

(76) Inventor: Takayuki Shindo, Nagano (JP)

( * ) Notice: Subject to any disclaimer, the term of this patent is extended or adjusted under 35 U.S.C. 154(b) by 1139 days.

(21) Appl. No.: 11/922,261

(22) PCT Filed: Mar. 1, 2006

(86) PCT No.: PCT/JP2006/304422
§ 371 (c)(1),
(2), (4) Date: Mar. 18, 2008

(87) PCT Pub. No.: WO2006/134692
PCT Pub. Date: Dec. 21, 2006

(65) Prior Publication Data
US 2009/0081125 A1   Mar. 26, 2009

(30) Foreign Application Priority Data

Jun. 16, 2005 (JP) ................. 2005-176580

(51) Int. Cl.
*C12Q 1/02* (2006.01)
*A61K 45/06* (2006.01)
*A61K 38/18* (2006.01)
*A61K 38/17* (2006.01)
*A61K 38/22* (2006.01)
*A61K 48/00* (2006.01)

(52) U.S. Cl.
CPC ................ *A61K 45/06* (2013.01); *A61K 38/18* (2013.01); *A61K 48/00* (2013.01); *A61K 38/1709* (2013.01); *A61K 38/1796* (2013.01); *A61K 38/22* (2013.01)

(58) Field of Classification Search
None
See application file for complete search history.

(56) References Cited

U.S. PATENT DOCUMENTS

| | | | | |
|---|---|---|---|---|
| 6,927,317 B2 * | 8/2005 | McNeish et al. | ............ | 800/18 |
| 2002/0178459 A1 * | 11/2002 | McNeish et al. | ............ | 800/18 |
| 2007/0105101 A1 * | 5/2007 | Susa Spring et al. | ............ | 435/6 |

FOREIGN PATENT DOCUMENTS

EP          1212941          6/2002

OTHER PUBLICATIONS

Deckers., Expression of vascular endothelial growth factors and their receptors during osteoblast differentiation, Endocrinology 141(5):1667-74, 2000.*
Dackor et al., Receptor activity-modifying proteins 2 and 3 have distinct physiological functions from embryogenesis to old age J. Biol. Chem. Jun. 22, 2007;282(25):18094-9.*
Fernandez-Sauze et al., Effects of adrenomedullin on endothelial cells in the multistep process of angiogenesis: involvement of CRLR/RAMP2 and CRLR/RAMP3 receptors, Int J Cancer. 108(6):797-804, 2004.*
McLatchie et al. "RAMPs regulate the transport and ligand specificity of the calcitonin-receptor-like receptor." Nature, vol. 393, pp. 333-339, 1998.*
Fernandez-Sauze et al. "Effects of adrenomedullin on endothelial cells in the Multistep process of angiogenesis: involvement of Crlr/ramp2 and crlr/ramp3 receptors." Int. J. Cancer (2004); 108: pp. 797-804.*
Fernandez-Sauze et al., "Effects of adrenomedullin on endothelial cells in the multistep process of angiogenesis: involvement of CRLR/RAMP2 and CRLR/RAMP3 receptors." Int J Cancern (2004);. 108(6):797-804.*
Iwase, et al., "Adrenomedullin Enhances Angiogenic Potency of Bone Marrow Transplantation in a Rat Model of Hindlimb Ischemia," Circulation, vol. 111, No. 3, Jan. 25, 2005, pp. 356-362.
Ashizuka, et al., "Effect of Adrenomedullin Administration on Acetic Acid-Induced Colitis in Rats," Peptides, vol. 26, No. 12, Dec. 1, 2005, pp. 2610-2615.
Morfis et al., "RAMPs: 5 years on, where to now?" Trends in Pharmacological Sciences vol. 24 No. 11, (Nov. 2003) 596-601.
Hay et al., "GPCR modulation by RAMPs" Pharmacology & Therapeutics 109 (2006) 173-197.
Dackor et al., "Receptor activity modifying proteins 2 and 3 Have Distinct Physiological Functions From Embryogenesis to Old Age" JBC Papers in Press, published Apr. 30, 2007 as Manuscript M703544200, 1-13.
Shigeki Kamitani et al., "The RAMP2/CRLR Complex is a Functional Adrenomedullin Recepter in Human Endothelial and Vascular Smooth Muscle Cells," Federation of European Biochemical Societies (FEBS), 1999, vol. 448, pp. 111-114.
Notice of Reasons for Rejection issued to JP Application No. 2007-521123, mailed Sep. 13, 2011.
Hippenstiel et al., "Adrenomedullin Reduces Endothelial Hyperpermeability", Circulation Research, vol. 91, 2002, pp. 618-625.
Chu et al., "Studies of the microvascular effects of adrenomedullin and related peptides", Peptides, vol. 22, 2001, pp. 1881-1886.
Kato et al., "Adrenomedullin as an Autocrine/Paracrine Apoptosis Survival Factor for Rat Endothelial Cells", Endocrinology, vol. 138, 1997, No. 6, pp. 2615-2620.
Gotoh et al., "Apoptosis in microvascular endothelial cells of perfused rabbit lungs with acute hydrostatic edema", Journal of Applied Physiology, vol. 88, 2000, pp. 518-526.
Kis et al., "Adrenomedullin, an Autocrine Mediator of Blood-Brain Barrier Function", Hypertension Research, vol. 26 (suppl), 2003, pp. S61-S70.
Iimuro et al., "Angiogenic Effects of Adrenomedullin in Ischemia and Tumor Growth", Circulation Research, vol. 95, 2004, pp. 415-423.

(Continued)

Primary Examiner — Thaian N Ton
Assistant Examiner — Titilayo Moloye
(74) Attorney, Agent, or Firm — Hoffmann & Baron, LLP

(57) ABSTRACT

It is intended to provide an angiogenic agent which contains, as the active ingredient, at least one substance selected from the group consisting of adrenomedullin, a substance inhibiting the activity of adrenomedullin degrading enzyme, an adrenomedullin receptor activity-modifying protein, a calcitonin receptor-like receptor and an adrenomedullin receptor.

2 Claims, 38 Drawing Sheets

(56) References Cited

OTHER PUBLICATIONS

Tokunaga et al., "Adrenomedullin Gene Transfer Induces Therapeutic Angiogenesis in a Rabbit Model of Chronic Hind Limb Ischemia", Circulation, vol. 109, 2004, pp. 526-531.

Caron et al., "Extreme hydrops fetalis and cardiovascular abnormalities in mice lacking a functional Adrenomedullin gene", PNAS, vol. 98, No. 2, 2001, pp. 615-619.

Shindo et al., "Hypotension and Resistance to Lipopolysaccharide-Induced Shock in Transgenic Mice Overexpressing Adrenomedullin in Their Vasculature", Circulation, vol. 101, 2000, pp. 2309-2316.

Shindo et al., "Vascular Abnormalities and Elevated Blood Pressure in Mice Lacking Adrenomedullin Gane", Circulation, vol. 104, 2001, pp. 1964-1971.

Oh-hashi et al., "Elevated Sympathetic Nervous Activity in Mice Deficient in αCGRP", Circulation Research, vol. 89, 2001, pp. 983-990.

Nishimatsu et al., "Role of Endogenous Adrenomedullin in the Regulation of Vascular Tone and Ischemic Renal Injury: Studies on Transgenic/Knockout Mice of Adrenomedullin Gane", Circulation Research, vol. 90, 2002, pp. 657-663.

Imai et al., "Resistance to Neointimal Hyperplasia and Fatty Streak Formation in Mice With Adrenomedullin Overexpression", Arteriosclerosis Thrombosis and Vascular Biology, vol. 22, 2002, pp. 1310-1315.

Niu et al., "Protective Effects of Endogenous Adrenomedullin on Cardiac Hypertrophy, Fibrosis, and Renal Damage", Circulation, vol. 109, 2004, pp. 1789-1794.

* cited by examiner

FIG. 6
A
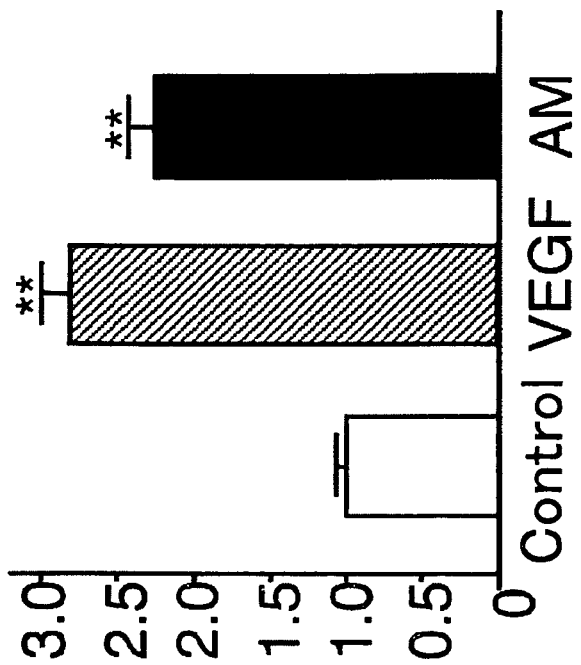
B
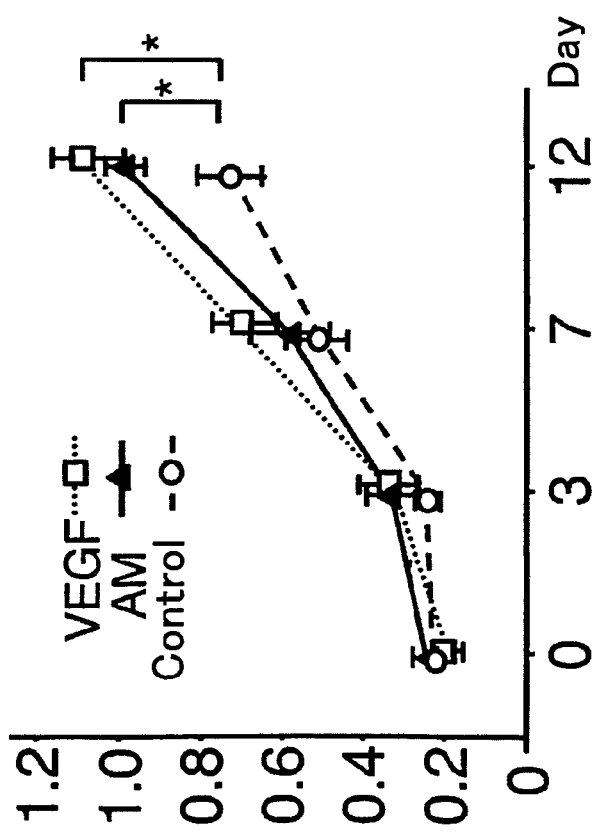

FIG. 7
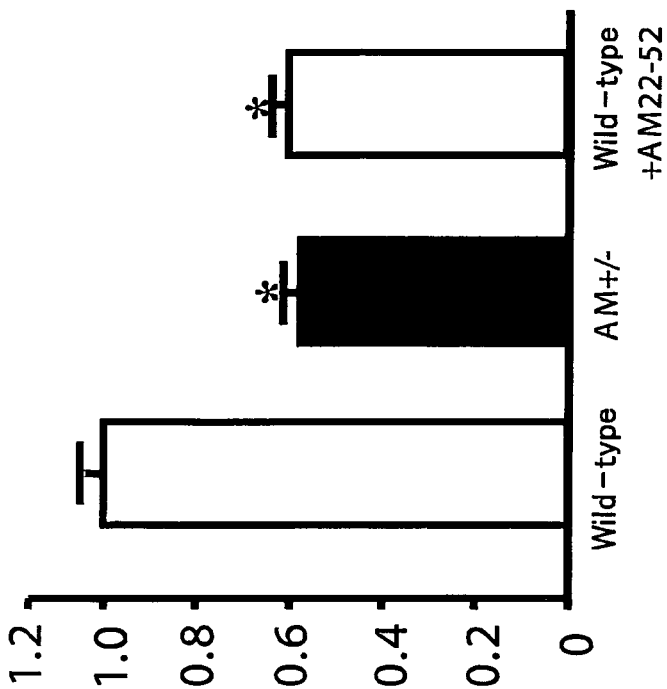
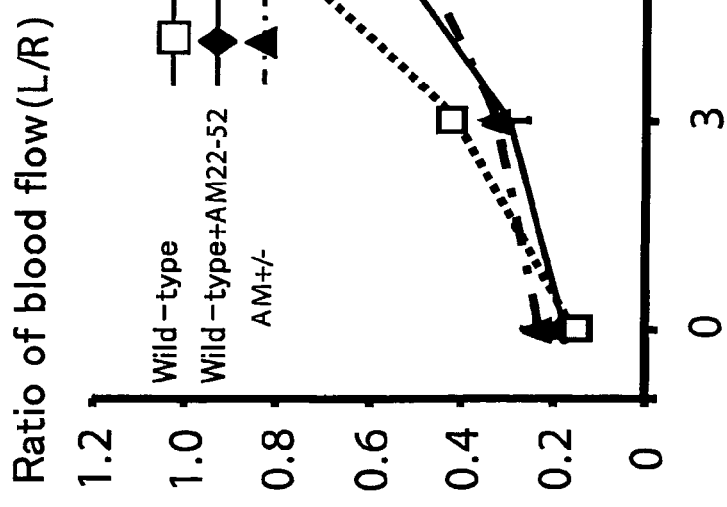

FIG. 11
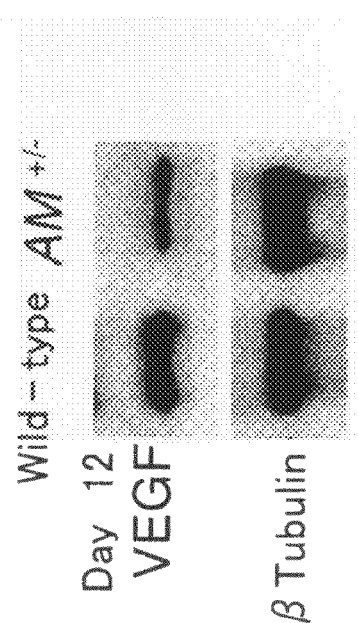
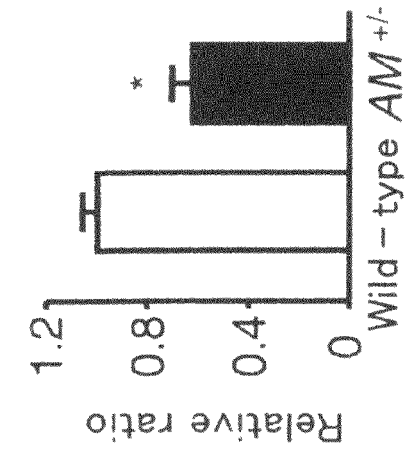
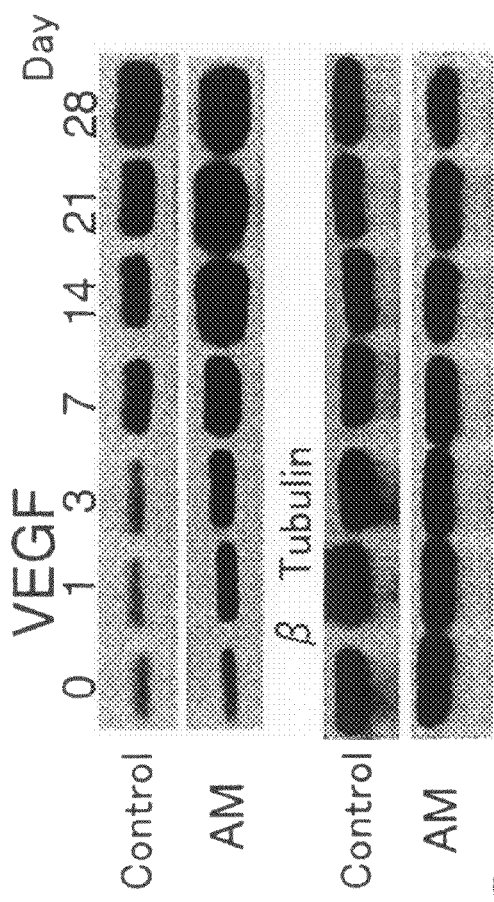
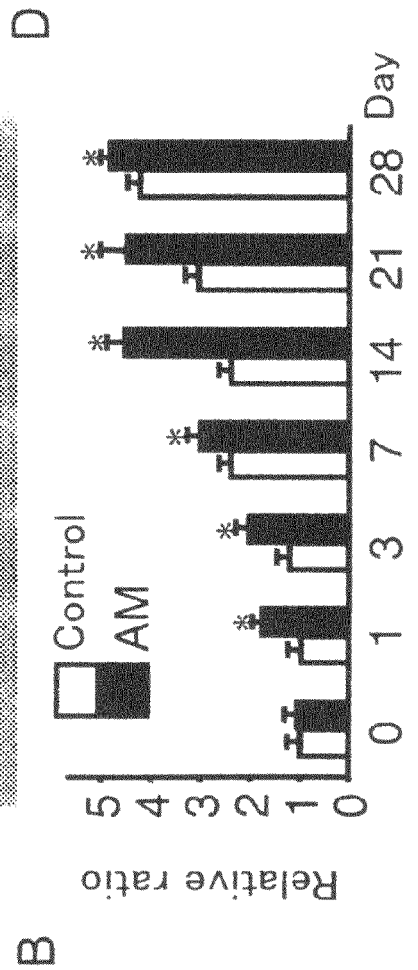

FIG. 20
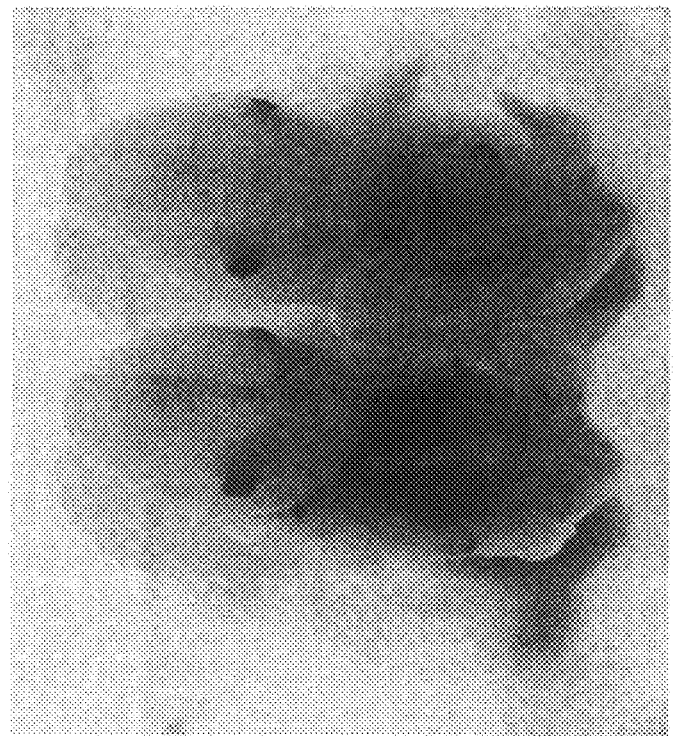

FIG. 29
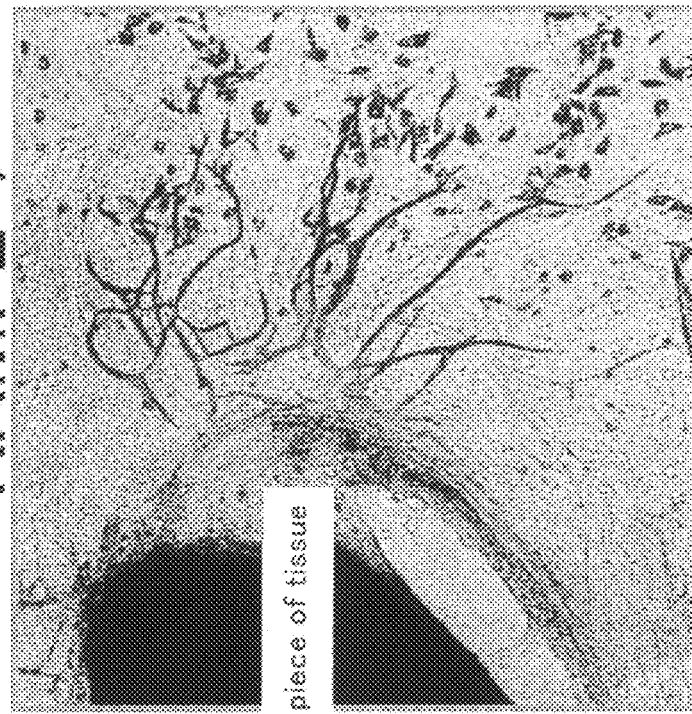
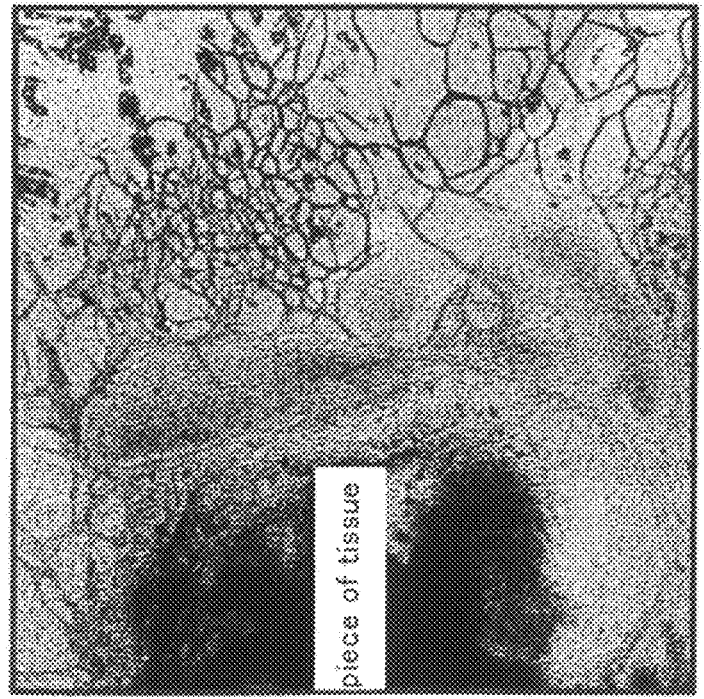

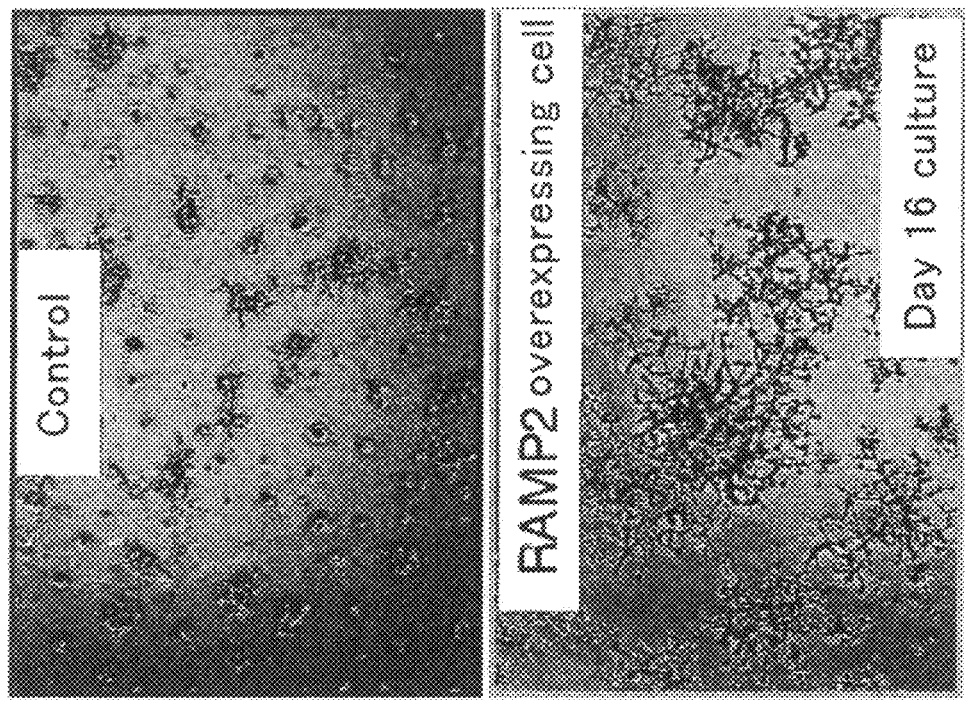
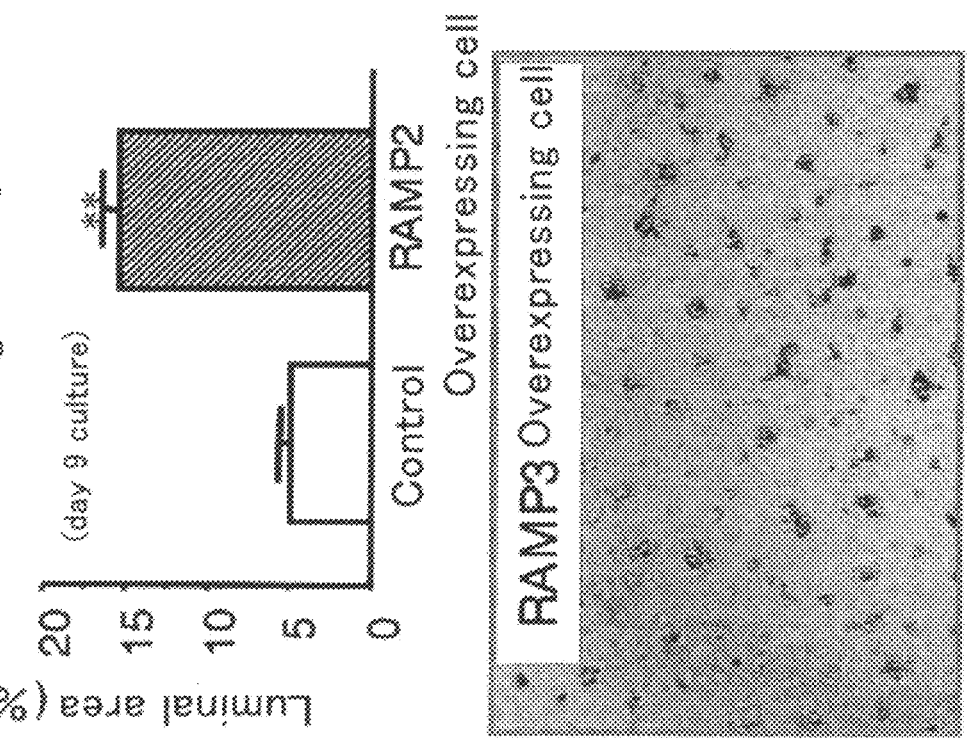
FIG. 36

FIG. 37 Cell proliferation (BrdU uptake assay) / Cell survival (WST-8 assay)

SEQUENCE LISTING

```
<160> NUMBER OF SEQ ID NOS: 24

<210> SEQ ID NO 1
<211> LENGTH: 1449
<212> TYPE: DNA
<213> ORGANISM: Homo sapiens
<220> FEATURE:
<221> NAME/KEY: CDS
<222> LOCATION: (439)..(594)

<400> SEQUENCE: 1
ctggatagaa cagctcaagc cttgccactt cgggcttctc actgcagctg ggcttggact      60
tcggagtttt gccattgcca gtgggacgtc tgagactttc tccttcaagt acttggcaga     120
tcactctctt agcagggtct gcgcttcgca gccgggatga agctggtttc cgtcgccctg     180
atgtacctgg gttcgctcgc cttcctaggc gctgacaccg ctcggttgga tgtcgcgtcg     240
gagtttcgaa agaagtggaa taagtgggct ctgagtcgtg ggaagaggga actgcggatg     300
```

-continued

```
tccagcagct accccaccgg gctcgctgac gtgaaggccg ggcctgccca gacccttatt       360 cggcccagg acatgaaggg tgcctctcga agccccgaag acagcagtcc ggatgccgcc        420
cgcatccgag tcaagcgc tac cgc cag agc atg aac aac ttc cag ggc ctc        471
                    Tyr Arg Gln Ser Met Asn Asn Phe Gln Gly Leu
                     1               5                   10 cgg agc ttt ggc tgc cgc ttc ggg acg tgc acg gtg cag aag ctg gca        519
Arg Ser Phe Gly Cys Arg Phe Gly Thr Cys Thr Val Gln Lys Leu Ala
         15                  20                  25 cac cag atc tac cag ttc aca gat aag gac aag gac aac gtc gcc ccc        567
His Gln Ile Tyr Gln Phe Thr Asp Lys Asp Lys Asp Asn Val Ala Pro
         30                  35                  40 agg agc aag atc agc ccc cag ggc tac ggccgccggc gccggcgctc              614
Arg Ser Lys Ile Ser Pro Gln Gly Tyr
         45                  50 cctgcccgag gccggcccgg gtcggactct ggtgtcttct aagccacaag cacacggggc      674 tccagcccc ccgagtggaa gtgctcccca cttctttag gatttaggcg cccatggtac        734
aaggaatagt cgcgcaagca tcccgctggt gcctcccggg acgaaggact tcccgagcgg      794 tgtgggacc gggctctgac agccctgcgg agaccctgag tccgggaggc accgtccggc      854
ggcgagctct ggctttgcaa gggcccctcc ttctgggggc ttcgcttcct tagccttgct      914
caggtgcaag tgccccaggg ggcggggtgc agaagaatcc gagtgtttgc aggcttaag      974 gagaggagaa actgagaaat gaatgctgag accccggag caggggtctg agccacagcc      1034
gtgctcgccc acaaactgat ttctcacggc gtgtcacccc accagggcgc aagcctcact     1094
attacttgaa ctttccaaaa cctaaagagg aaaagtgcaa tgcgtgttgt acatacagag     1154
gtaactatca atatttaagt ttgttgctgt caagatttt tttgtaactt caaatataga     1214
gatatttttg tacgttatat attgtattaa gggcatttta aaagcaatta tattgtcctc     1274
ccctatttta agacgtgaat gtctcagcga ggtgtaaagt tgttcgccgc gtggaatgtg     1334
agtgtgtttg tgtgcatgaa agagaaagac tgattacctc ctgtgtggaa gaaggaaaca     1394
ccgagtctct gtataatcta tttacataaa atgggtgata tgcgaacagc aaacc          1449
```

<210> SEQ ID NO 2
<211> LENGTH: 52
<212> TYPE: PRT
<213> ORGANISM: Homo sapiens

<400> SEQUENCE: 2

```
Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
             20                  25                  30

Phe Thr Asp Lys Asp Lys Asp Asn Val Ala Pro Arg Ser Lys Ile Ser
         35                  40                  45

Pro Gln Gly Tyr
     50
```

<210> SEQ ID NO 3
<211> LENGTH: 2984
<212> TYPE: DNA
<213> ORGANISM: Homo sapiens
<220> FEATURE:
<221> NAME/KEY: CDS
<222> LOCATION: (506)..(1891)

<400> SEQUENCE: 3

```
gaacaacctc tctctctcca gcagagagtg tcacctcctg ctttaggacc atcaagctct    60
gctaactgaa tctcatccta attgcaggat cacattgcaa agctttcact ctttcccacc   120
ttgcttgtgg gtaaatctct tctgcggaat ctcagaaagt aaagttccat cctgagaata   180
tttcacaaag aatttcctta agagctggac tgggtcttga cccctgaatt taagaaattc   240
ttaaagacaa tgtcaaatat gatccaagag aaaatgtgat ttgagtctgg agacaattgt   300
gcatatcgtc taataataaa aacccatact agcctataga aaacaatatt tgaaagattg   360
ctaccactaa aaagaaaact actacaactt gacaagactg ctgcaaactt caatttgtca   420
accacaactt gacaaggttg ctataaaaca agattgctac aacttctagt ttatgttata   480
cagcatattt cattttggct taatg atg gag aaa aag tgt acc ctg tat ttt    532
                            Met Glu Lys Lys Cys Thr Leu Tyr Phe
                             1               5 ctg gtt ctc ttg cct ttt ttt atg att ctt gta aca gca gaa tta gaa    580
Leu Val Leu Leu Pro Phe Phe Met Ile Leu Val Thr Ala Glu Leu Glu
 10              15                  20                  25 gag agt cct gag gac tca att cag ttg gga gtt act aga aat aaa atc    628
Glu Ser Pro Glu Asp Ser Ile Gln Leu Gly Val Thr Arg Asn Lys Ile
                 30                  35                  40 atg aca gct caa tat gaa tgt tac caa aag att atg caa gac ccc att    676
Met Thr Ala Gln Tyr Glu Cys Tyr Gln Lys Ile Met Gln Asp Pro Ile
                 45                  50                  55 caa caa gca gaa ggc gtt tac tgc aac aga acc tgg gat gga tgg ctc    724
Gln Gln Ala Glu Gly Val Tyr Cys Asn Arg Thr Trp Asp Gly Trp Leu
             60                  65                  70 tgc tgg aac gat gtt gca gca gga act gaa tca atg cag ctc tgc cct    772
Cys Trp Asn Asp Val Ala Ala Gly Thr Glu Ser Met Gln Leu Cys Pro
 75                  80                  85 gat tac ttt cag gac ttt gat cca tca gaa aaa gtt aca aag atc tgt    820
Asp Tyr Phe Gln Asp Phe Asp Pro Ser Glu Lys Val Thr Lys Ile Cys
 90                  95                 100                 105 gac caa gat gga aac tgg ttt aga cat cca gca agc aac aga aca tgg    868
Asp Gln Asp Gly Asn Trp Phe Arg His Pro Ala Ser Asn Arg Thr Trp
                110                 115                 120 aca aat tat acc cag tgt aat gtt aac acc cac gag aaa gtg aag act    916
Thr Asn Tyr Thr Gln Cys Asn Val Asn Thr His Glu Lys Val Lys Thr
                125                 130                 135 gca cta aat ttg ttt tac ctg acc ata att gga cac gga ttg tct att    964
Ala Leu Asn Leu Phe Tyr Leu Thr Ile Ile Gly His Gly Leu Ser Ile
        140                 145                 150 gca tca ctg ctt atc tcg ctt ggc ata ttc ttt tat ttc aag agc cta   1012
Ala Ser Leu Leu Ile Ser Leu Gly Ile Phe Phe Tyr Phe Lys Ser Leu
155                 160                 165 agt tgc caa agg att acc tta cac aaa aat ctg ttc ttc tca ttt gtt   1060
Ser Cys Gln Arg Ile Thr Leu His Lys Asn Leu Phe Phe Ser Phe Val
170                 175                 180                 185 tgt aac tct gtt gta aca atc att cac ctc act gca gtg gcc aac aac   1108
Cys Asn Ser Val Val Thr Ile Ile His Leu Thr Ala Val Ala Asn Asn
                190                 195                 200 cag gcc tta gta gcc aca aat cct gtt agt tgc aaa gtg tcc cag ttc   1156
Gln Ala Leu Val Ala Thr Asn Pro Val Ser Cys Lys Val Ser Gln Phe
            205                 210                 215 att cat ctt tac ctg atg ggc tgt aat tac ttt tgg atg ctc tgt gaa   1204
Ile His Leu Tyr Leu Met Gly Cys Asn Tyr Phe Trp Met Leu Cys Glu
            220                 225                 230 ggc att tac cta cac aca ctc att gtg gtg gcc gtg ttt gca gag aag   1252
Gly Ile Tyr Leu His Thr Leu Ile Val Val Ala Val Phe Ala Glu Lys
        235                 240                 245
```

```
caa cat tta atg tgg tat tat ttt ctt ggc tgg gga ttt cca ctg att      1300
Gln His Leu Met Trp Tyr Tyr Phe Leu Gly Trp Gly Phe Pro Leu Ile
250                 255                 260                 265 cct gct tgt ata cat gcc att gct aga agc tta tat tac aat gac aat      1348
Pro Ala Cys Ile His Ala Ile Ala Arg Ser Leu Tyr Tyr Asn Asp Asn
                270                 275                 280 tgc tgg atc agt tct gat acc cat ctc ctc tac att atc cat ggc cca      1396
Cys Trp Ile Ser Ser Asp Thr His Leu Leu Tyr Ile Ile His Gly Pro
            285                 290                 295 att tgt gct gct tta ctg gtg aat ctt ttt ttc ttg tta aat att gta      1444
Ile Cys Ala Ala Leu Leu Val Asn Leu Phe Phe Leu Leu Asn Ile Val
        300                 305                 310 cgc gtt ctc atc acc aag tta aaa gtt aca cac caa gcg gaa tcc aat      1492
Arg Val Leu Ile Thr Lys Leu Lys Val Thr His Gln Ala Glu Ser Asn
    315                 320                 325 ctg tac atg aaa gct gtg aga gct act ctt atc ttg gtg cca ttg ctt      1540
Leu Tyr Met Lys Ala Val Arg Ala Thr Leu Ile Leu Val Pro Leu Leu
330                 335                 340                 345 ggc att gaa ttt gtg ctg att cca tgg cga cct gaa gga aag att gca      1588
Gly Ile Glu Phe Val Leu Ile Pro Trp Arg Pro Glu Gly Lys Ile Ala
                350                 355                 360 gag gag gta tat gac tac atc atg cac atc ctt atg cac ttc cag ggt      1636
Glu Glu Val Tyr Asp Tyr Ile Met His Ile Leu Met His Phe Gln Gly
            365                 370                 375 ctt ttg gtc tct acc att ttc tgc ttc ttt aat gga gag gtt caa gca      1684
Leu Leu Val Ser Thr Ile Phe Cys Phe Phe Asn Gly Glu Val Gln Ala
        380                 385                 390 att ctg aga aga aac tgg aat caa tac aaa atc caa ttt gga aac agc      1732
Ile Leu Arg Arg Asn Trp Asn Gln Tyr Lys Ile Gln Phe Gly Asn Ser
    395                 400                 405 ttt tcc aac tca gaa gct ctt cgt agt gcg tct tac aca gtg tca aca      1780
Phe Ser Asn Ser Glu Ala Leu Arg Ser Ala Ser Tyr Thr Val Ser Thr
410                 415                 420                 425 atc agt gat ggt cca ggt tat agt cat gac tgt cct agt gaa cac tta      1828
Ile Ser Asp Gly Pro Gly Tyr Ser His Asp Cys Pro Ser Glu His Leu
                430                 435                 440 aat gga aaa agc atc cat gat att gaa aat gtt ctc tta aaa cca gaa      1876
Asn Gly Lys Ser Ile His Asp Ile Glu Asn Val Leu Leu Lys Pro Glu
            445                 450                 455 aat tta tat aat tga aaatagaagg atggttgtct cactgttttg tgcttctcct      1931
Asn Leu Tyr Asn
        460 aactcaagga cttggaccca tgactctgta gccagaagac ttcaatatta aatgactttt    1991 tgaatgtcat aaagaagagc cttcacatga aattagtagt gtgttgataa gagtgtaaca    2051 tccagctcta tgtgggaaaa agaaatcct ggtttgtaat gtttgtcagt aaatactccc     2111 actatgcctg atgtgacgct actaacctga catcaccaag tgtggaattg agaaaagca     2171 caatcaactt ttctgagctg gtgtaagcca gttccagcac accattgcat gaattcacaa    2231 acaaatggct gtaaaactaa acatacatgt tgggcatgat tctacccta ttgccccaag     2291 agacctagct aaggtctata acatgaagg gaaaattagc ttttagtttt aaaactcttt     2351 atcccatctt gattggggca gttgactttt tttttgccca gagtgccgta gtcctttttg    2411 taactaccct ctcaaatgga caataccaga agtgaattat ccctgctggc tttcttttct    2471 ctatgaaaag caactgagta caattgttat gatctactca tttgctgaca catcagttat    2531 atcttgtggc atatccattg tggaaactgg atgaacagga tgtataatat gcaatcctac    2591
```

-continued

```
ttctatatca ttaggaaaac atcttagttg atgctacaaa acaccttgtc aacctcttcc      2651
tgtcttacca acagtggga gggaattcct agctgtaaat ataaattttg tcccttccat       2711
ttctactgta taaacaaatt agcaatcatt ttatataaag aaaatcaatg aaggatttct      2771 tatttcttg gaattttgta aaagaaatt gtgaaaaatg agcttgtaaa tactccatta        2831
ttttatttta tagtctcaaa tcaaatacat acaacctatg taattttaa agcaaatata        2891 taatgcaaca atgtgtgtat gttaatatct gatactgtat ctgggctgat ttttaaata       2951 aaatagagtc tggaatgcta aaaaaaaaaa aaa                                   2984
```

<210> SEQ ID NO 4
<211> LENGTH: 461
<212> TYPE: PRT
<213> ORGANISM: Homo sapiens

<400> SEQUENCE: 4

```
Met Glu Lys Lys Cys Thr Leu Tyr Phe Leu Val Leu Leu Pro Phe Phe
1               5                   10                  15

Met Ile Leu Val Thr Ala Glu Leu Glu Glu Ser Pro Glu Asp Ser Ile
                20                  25                  30

Gln Leu Gly Val Thr Arg Asn Lys Ile Met Thr Ala Gln Tyr Glu Cys
            35                  40                  45

Tyr Gln Lys Ile Met Gln Asp Pro Ile Gln Gln Ala Glu Gly Val Tyr
        50                  55                  60

Cys Asn Arg Thr Trp Asp Gly Trp Leu Cys Trp Asn Asp Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala Leu Asn Leu Phe Tyr Leu
    130                 135                 140

Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Ile Pro Ala Cys Ile His Ala Ile
            260                 265                 270

Ala Arg Ser Leu Tyr Tyr Asn Asp Asn Cys Trp Ile Ser Ser Asp Thr
        275                 280                 285

His Leu Leu Tyr Ile Ile His Gly Pro Ile Cys Ala Ala Leu Leu Val
    290                 295                 300
```

```
Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
            325                 330                 335

Ala Thr Leu Ile Leu Val Pro Leu Leu Gly Ile Glu Phe Val Leu Ile
            340                 345                 350

Pro Trp Arg Pro Glu Gly Lys Ile Ala Glu Glu Val Tyr Asp Tyr Ile
        355                 360                 365

Met His Ile Leu Met His Phe Gln Gly Leu Leu Val Ser Thr Ile Phe
    370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Ser Phe Ser Asn Ser Glu Ala Leu
            405                 410                 415

Arg Ser Ala Ser Tyr Thr Val Ser Thr Ile Ser Asp Gly Pro Gly Tyr
            420                 425                 430

Ser His Asp Cys Pro Ser Glu His Leu Asn Gly Lys Ser Ile His Asp
        435                 440                 445

Ile Glu Asn Val Leu Leu Lys Pro Glu Asn Leu Tyr Asn
    450                 455                 460

<210> SEQ ID NO 5
<211> LENGTH: 1620
<212> TYPE: DNA
<213> ORGANISM: Homo sapiens
<220> FEATURE:
<221> NAME/KEY: CDS
<222> LOCATION: (95)..(1309)

<400> SEQUENCE: 5
cagcctcctc acagctcccc atagcctgga cctgccggcc ctccctccag gaccgagggg      60
ctcccaaggg aaactcaggc gtgtgctggt ccca atg tca gtg aaa ccc agc tgg    115
                                    Met Ser Val Lys Pro Ser Trp
                                      1               5 ggg cct ggc ccc tcg gag ggg gtc acc gca gtg cct acc agt gac ctt      163
Gly Pro Gly Pro Ser Glu Gly Val Thr Ala Val Pro Thr Ser Asp Leu
         10                  15                  20 gga gag atc cac aac tgg acc gag ctg ctt gac ctc ttc aac cac act      211
Gly Glu Ile His Asn Trp Thr Glu Leu Leu Asp Leu Phe Asn His Thr
 25                  30                  35 ttg tct gag tgc cac gtg gag ctc agc cag agc acc aag cgc gtg gtc      259
Leu Ser Glu Cys His Val Glu Leu Ser Gln Ser Thr Lys Arg Val Val
 40                  45                  50                  55 ctc ttt gcc ctc tac ctg gcc atg ttt gtg gtt ggg ctg gtg gag aac      307
Leu Phe Ala Leu Tyr Leu Ala Met Phe Val Val Gly Leu Val Glu Asn
             60                  65                  70 ctc ctg gtg ata tgc gtc aac tgg cgc ggc tca ggc cgg gca ggg ctg      355
Leu Leu Val Ile Cys Val Asn Trp Arg Gly Ser Gly Arg Ala Gly Leu
         75                  80                  85 atg aac ctc tac atc ctc aac atg gcc atc gcg gac ctg ggc att gtc      403
Met Asn Leu Tyr Ile Leu Asn Met Ala Ile Ala Asp Leu Gly Ile Val
 90                  95                 100 ctg tct ctg ccc gtg tgg atg ctg gag gtc acg ctg gac tac acc tgg      451
Leu Ser Leu Pro Val Trp Met Leu Glu Val Thr Leu Asp Tyr Thr Trp
            105                 110                 115 ctc tgg ggc agc ttc tcc tgc cgc ttc act cac tac ttc tac ttt gtc      499
Leu Trp Gly Ser Phe Ser Cys Arg Phe Thr His Tyr Phe Tyr Phe Val
120                 125                 130                 135
```

```
aac atg tat agc agc atc ttc ttc ctg gtg tgc ctc agt gtc gac cgc    547
Asn Met Tyr Ser Ser Ile Phe Phe Leu Val Cys Leu Ser Val Asp Arg
            140                 145                 150 tat gtc acc ctc acc agc gcc tcc ccc tcc tgg cag cgt tac cag cac    595
Tyr Val Thr Leu Thr Ser Ala Ser Pro Ser Trp Gln Arg Tyr Gln His
            155                 160                 165 cga gtg cgg cgg gcc atg tgt gca ggc atc tgg gtc ctc tcg gcc atc    643
Arg Val Arg Arg Ala Met Cys Ala Gly Ile Trp Val Leu Ser Ala Ile
            170                 175                 180 atc ccg ctg cct gag gtg gtc cac atc cag ctg gtg gag ggc cct gag    691
Ile Pro Leu Pro Glu Val Val His Ile Gln Leu Val Glu Gly Pro Glu
        185                 190                 195 ccc atg tgc ctc ttc atg gca cct ttt gaa acg tac agc acc tgg gcc    739
Pro Met Cys Leu Phe Met Ala Pro Phe Glu Thr Tyr Ser Thr Trp Ala
200                 205                 210                 215 ctg gcg gtg gcc ctg tcc acc acc atc ctg ggc ttc ctg ctg ccc ttc    787
Leu Ala Val Ala Leu Ser Thr Thr Ile Leu Gly Phe Leu Leu Pro Phe
                220                 225                 230 cct ctc atc aca gtc ttc aat gtg ctg aca gcc tgc cgg ctg cgg cag    835
Pro Leu Ile Thr Val Phe Asn Val Leu Thr Ala Cys Arg Leu Arg Gln
                235                 240                 245 cca gga caa ccc aag agc cgg cgc cac tgc ctg ctg ctg tgc gcc tac    883
Pro Gly Gln Pro Lys Ser Arg Arg His Cys Leu Leu Leu Cys Ala Tyr
            250                 255                 260 gtg gcc gtc ttt gtc atg tgc tgg ctg ccc tat cat gtg acc ctg ctg    931
Val Ala Val Phe Val Met Cys Trp Leu Pro Tyr His Val Thr Leu Leu
265                 270                 275 ctg ctc aca ctg cat ggg acc cac atc tcc ctc cac tgc cac ctg gtc    979
Leu Leu Thr Leu His Gly Thr His Ile Ser Leu His Cys His Leu Val
280                 285                 290                 295 cac ctg ctc tac ttc ttc tat gat gtc att gac tgc ttc tcc atg ctg   1027
His Leu Leu Tyr Phe Phe Tyr Asp Val Ile Asp Cys Phe Ser Met Leu
                300                 305                 310 cac tgt gtc atc aac ccc atc ctt tac aac ttt ctc agc cca cac ttc   1075
His Cys Val Ile Asn Pro Ile Leu Tyr Asn Phe Leu Ser Pro His Phe
                315                 320                 325 cgg ggc cgg ctc ctg aat gct gta gtc cat tac ctt cct aag gac cag   1123
Arg Gly Arg Leu Leu Asn Ala Val Val His Tyr Leu Pro Lys Asp Gln
            330                 335                 340 acc aag gcg ggc aca tgc gcc tcc tct tcc tcc tgt tcc acc cag cat   1171
Thr Lys Ala Gly Thr Cys Ala Ser Ser Ser Ser Cys Ser Thr Gln His
        345                 350                 355 tcc atc atc atc acc aag ggt gat agc cag cct gct gca gcc ccc       1219
Ser Ile Ile Ile Thr Lys Gly Asp Ser Gln Pro Ala Ala Ala Pro
360                 365                 370                 375 cac cct gag cca agc ctg agc ttt cag gca cac cat ttg ctt cca aat   1267
His Pro Glu Pro Ser Leu Ser Phe Gln Ala His His Leu Leu Pro Asn
                380                 385                 390 act tcc ccc atc tct ccc act cag cct ctt aca ccc agc tga           1309
Thr Ser Pro Ile Ser Pro Thr Gln Pro Leu Thr Pro Ser
                395                 400 ggtagaggcc agactcctcc aacagtgaag gaaaaggcac aggtgagagt ataggtggga  1369
gatttggggg gatgtagagg ggagggtcaa agcactcgtg gtcaattttg aatctatctt  1429
aaaatactga ggtgtggaga gagagacagg atcaggagcg atagagagca ggccctcagt  1489
gttgtactat ttgtctcggt ccttgtgtct aaggagcaat gcagaaaaaa aggtgaaata  1549 aatgaagagag atagccatgg aaaaaaaaaa aaaaaaaaaa aaaaaaaaaa aaaaaaaaaa  1609
aaaaaaaaaa a                                                       1620
```

```
<210> SEQ ID NO 6
<211> LENGTH: 404
<212> TYPE: PRT
<213> ORGANISM: Homo sapiens

<400> SEQUENCE: 6

Met Ser Val Lys Pro Ser Trp Gly Pro Gly Pro Ser Glu Gly Val Thr
1               5                   10                  15

Ala Val Pro Thr Ser Asp Leu Gly Glu Ile His Asn Trp Thr Glu Leu
            20                  25                  30

Leu Asp Leu Phe Asn His Thr Leu Ser Glu Cys His Val Glu Leu Ser
        35                  40                  45

Gln Ser Thr Lys Arg Val Val Leu Phe Ala Leu Tyr Leu Ala Met Phe
    50                  55                  60

Val Gly Leu Val Glu Asn Leu Leu Val Ile Cys Val Asn Trp Arg
65                  70                  75                  80

Gly Ser Gly Arg Ala Gly Leu Met Asn Leu Tyr Ile Leu Asn Met Ala
                85                  90                  95

Ile Ala Asp Leu Gly Ile Val Leu Ser Leu Pro Val Trp Met Leu Glu
            100                 105                 110

Val Thr Leu Asp Tyr Thr Trp Leu Trp Gly Ser Phe Ser Cys Arg Phe
        115                 120                 125

Thr His Tyr Phe Tyr Phe Val Asn Met Tyr Ser Ser Ile Phe Phe Leu
    130                 135                 140

Val Cys Leu Ser Val Asp Arg Tyr Val Thr Leu Thr Ser Ala Ser Pro
145                 150                 155                 160

Ser Trp Gln Arg Tyr Gln His Arg Val Arg Arg Ala Met Cys Ala Gly
                165                 170                 175

Ile Trp Val Leu Ser Ala Ile Ile Pro Leu Pro Glu Val Val His Ile
            180                 185                 190

Gln Leu Val Glu Gly Pro Glu Pro Met Cys Leu Phe Met Ala Pro Phe
        195                 200                 205

Glu Thr Tyr Ser Thr Trp Ala Leu Ala Val Ala Leu Ser Thr Thr Ile
    210                 215                 220

Leu Gly Phe Leu Leu Pro Phe Pro Leu Ile Thr Val Phe Asn Val Leu
225                 230                 235                 240

Thr Ala Cys Arg Leu Arg Gln Pro Gly Gln Pro Lys Ser Arg Arg His
                245                 250                 255

Cys Leu Leu Leu Cys Ala Tyr Val Ala Val Phe Val Met Cys Trp Leu
            260                 265                 270

Pro Tyr His Val Thr Leu Leu Leu Thr Leu His Gly Thr His Ile
        275                 280                 285

Ser Leu His Cys His Leu Val His Leu Leu Tyr Phe Phe Tyr Asp Val
    290                 295                 300

Ile Asp Cys Phe Ser Met Leu His Cys Val Ile Asn Pro Ile Leu Tyr
305                 310                 315                 320

Asn Phe Leu Ser Pro His Phe Arg Gly Arg Leu Leu Asn Ala Val Val
                325                 330                 335

His Tyr Leu Pro Lys Asp Gln Thr Lys Ala Gly Thr Cys Ala Ser Ser
            340                 345                 350

Ser Ser Cys Ser Thr Gln His Ser Ile Ile Ile Thr Lys Gly Asp Ser
        355                 360                 365

Gln Pro Ala Ala Ala Ala Pro His Pro Glu Pro Ser Leu Ser Phe Gln
```

```
                370                 375                 380
Ala His His Leu Leu Pro Asn Thr Ser Pro Ile Ser Pro Thr Gln Pro
385                 390                 395                 400

Leu Thr Pro Ser

<210> SEQ ID NO 7
<211> LENGTH: 800
<212> TYPE: DNA
<213> ORGANISM: Homo sapiens
<220> FEATURE:
<221> NAME/KEY: CDS
<222> LOCATION: (33)..(479)

<400> SEQUENCE: 7
cgagcggact cgactcggca ccgctgtgca cc atg gcc cgg gcc ctg tgc cgc       53
                                   Met Ala Arg Ala Leu Cys Arg
                                     1               5 ctc ccg cgg cgc ggc ctc tgg ctg ctc ctg gcc cat cac ctc ttc atg     101
Leu Pro Arg Arg Gly Leu Trp Leu Leu Leu Ala His His Leu Phe Met
         10                  15                  20 acc act gcc tgc cag gag gct aac tac ggt gcc ctc ctc cgg gag ctc     149
Thr Thr Ala Cys Gln Glu Ala Asn Tyr Gly Ala Leu Leu Arg Glu Leu
 25                  30                  35 tgc ctc acc cag ttc cag gta gac atg gag gcc gtc ggg gag acg ctg     197
Cys Leu Thr Gln Phe Gln Val Asp Met Glu Ala Val Gly Glu Thr Leu
40                  45                  50                  55 tgg tgt gac tgg ggc agg acc atc agg agc tac agg gag ctg gcc gac     245
Trp Cys Asp Trp Gly Arg Thr Ile Arg Ser Tyr Arg Glu Leu Ala Asp
                 60                  65                  70 tgc acc tgg cac atg gcg gag aag ctg ggc tgc ttc tgg ccc aat gca     293
Cys Thr Trp His Met Ala Glu Lys Leu Gly Cys Phe Trp Pro Asn Ala
             75                  80                  85 gag gtg gac agg ttc ttc ctg gca gtg cat ggc cgc tac ttc agg agc     341
Glu Val Asp Arg Phe Phe Leu Ala Val His Gly Arg Tyr Phe Arg Ser
         90                  95                 100 tgc ccc atc tca ggc agg gcc gtg cgg gac ccg ccc ggc agc atc ctc     389
Cys Pro Ile Ser Gly Arg Ala Val Arg Asp Pro Pro Gly Ser Ile Leu
    105                 110                 115 tac ccc ttc atc gtg gtc ccc atc acg gtg acc ctg ctg gtg acg gca     437
Tyr Pro Phe Ile Val Val Pro Ile Thr Val Thr Leu Leu Val Thr Ala
120                 125                 130                 135 ctg gtg gtc tgg cag agc aag cgc act gag ggc att gtg tag           479
Leu Val Val Trp Gln Ser Lys Arg Thr Glu Gly Ile Val
                140                 145 gcggggccca ggctgcccgc gggtgcaccc aggctgcagg gtgaggccag gcaggcctgg    539
gtaggggcag cttctggagc cttgggacag agcaggccca caatgccccc cttcttccag    599
ccaagaagag ctcacaggag tccagagtag ccgaggctct ggtattaacc tggaagcccc    659
cctggctgga ggccaccgcc accctaggaa gggggcaggg acgtgacctt gacttacctc    719
tggaaagggt cccagcctag actgcttacc ccatagccac atttgtggat gagtggtttg    779
tgattaaaag ggatgttctt g                                             800

<210> SEQ ID NO 8
<211> LENGTH: 148
<212> TYPE: PRT
<213> ORGANISM: Homo sapiens

<400> SEQUENCE: 8

Met Ala Arg Ala Leu Cys Arg Leu Pro Arg Arg Gly Leu Trp Leu Leu
```

```
                1               5                       10                      15
            Leu Ala His His Leu Phe Met Thr Thr Ala Cys Gln Glu Ala Asn Tyr
                                20                      25                      30

Gly Ala Leu Leu Arg Glu Leu Cys Leu Thr Gln Phe Gln Val Asp Met
                                35                      40                      45

Glu Ala Val Gly Glu Thr Leu Trp Cys Asp Trp Gly Arg Thr Ile Arg
                                50                      55                      60

Ser Tyr Arg Glu Leu Ala Asp Cys Thr Trp His Met Ala Glu Lys Leu
            65                      70                      75                      80

Gly Cys Phe Trp Pro Asn Ala Glu Val Asp Arg Phe Leu Ala Val
                                    85                      90                      95

His Gly Arg Tyr Phe Arg Ser Cys Pro Ile Ser Gly Arg Ala Val Arg
                                100                     105                     110

Asp Pro Pro Gly Ser Ile Leu Tyr Pro Phe Ile Val Pro Ile Thr
                                115                     120                     125

Val Thr Leu Leu Val Thr Ala Leu Val Val Trp Gln Ser Lys Arg Thr
                                130                     135                     140

Glu Gly Ile Val
            145

<210> SEQ ID NO 9
<211> LENGTH: 780
<212> TYPE: DNA
<213> ORGANISM: Homo sapiens
<220> FEATURE:
<221> NAME/KEY: CDS
<222> LOCATION: (69)..(596)

<400> SEQUENCE: 9
ggatataggc gccccacac ccgggcccgg ctaagcgccg ccgccgctcc tcgcctcctt         60 gctgcacg atg gcc tcg ctc cgg gtg gag cgc gcc ggc ggc ccg cgt ctc       110
         Met Ala Ser Leu Arg Val Glu Arg Ala Gly Gly Pro Arg Leu
             1               5                       10 cct agg acc cga gtc ggg cgg ccg gca gcc gtc cgc ctc ctc ctt ctg       158
Pro Arg Thr Arg Val Gly Arg Pro Ala Ala Val Arg Leu Leu Leu Leu
15                  20                      25                      30 ctg ggc gct gtc ctg aat ccc cac gag gcc ctg gct cag cct ctt ccc       206
Leu Gly Ala Val Leu Asn Pro His Glu Ala Leu Ala Gln Pro Leu Pro
                    35                      40                      45 acc aca ggc aca cca ggg tca gaa ggg ggg acg gtg aag aac tat gag       254
Thr Thr Gly Thr Pro Gly Ser Glu Gly Gly Thr Val Lys Asn Tyr Glu
                50                      55                      60 aca gct gtc caa ttt tgc tgg aat cat tat aag gat caa atg gat cct       302
Thr Ala Val Gln Phe Cys Trp Asn His Tyr Lys Asp Gln Met Asp Pro
65                  70                      75 atc gaa aag gat tgg tgc gac tgg gcc atg att agc agg cct tat agc       350
Ile Glu Lys Asp Trp Cys Asp Trp Ala Met Ile Ser Arg Pro Tyr Ser
80                      85                      90 acc ctg cga gat tgc ctg gag cac ttt gca gag ttg ttt gac ctg ggc       398
Thr Leu Arg Asp Cys Leu Glu His Phe Ala Glu Leu Phe Asp Leu Gly
95                      100                     105                     110 ttc ccc aat ccc ttg gca gag agg atc atc ttt gag act cac cag atc       446
Phe Pro Asn Pro Leu Ala Glu Arg Ile Ile Phe Glu Thr His Gln Ile
                        115                     120                     125 cac ttt gcc aac tgc tcc ctg gtg cag ccc acc ttc tct gac ccc cca       494
His Phe Ala Asn Cys Ser Leu Val Gln Pro Thr Phe Ser Asp Pro Pro
                    130                     135                     140 gag gat gta ctc ctg gcc atg atc ata gcc ccc atc tgc ctc atc ccc       542
Glu Asp Val Leu Leu Ala Met Ile Ile Ala Pro Ile Cys Leu Ile Pro
```

```
Glu Asp Val Leu Leu Ala Met Ile Ile Ala Pro Ile Cys Leu Ile Pro
            145                 150                 155 ttc ctc atc act ctt gta gta tgg agg agt aaa gac agt gag gcc cag         590
Phe Leu Ile Thr Leu Val Val Trp Arg Ser Lys Asp Ser Glu Ala Gln
    160                 165                 170 gcc tag ggggcacgag cttctcaaca accatgttac tccacttccc caccccacc           646
Ala
175 aggcctccct cctcccctcc tactccctt tctcactctc atccccacca cagatccctg         706 gattgctggg aatggaagcc agggttgggc atggcacaag ttctgtaatc ttcaaaataa       766 aactttttt ttga                                                           780

<210> SEQ ID NO 10
<211> LENGTH: 175
<212> TYPE: PRT
<213> ORGANISM: Homo sapiens

<400> SEQUENCE: 10

Met Ala Ser Leu Arg Val Glu Arg Ala Gly Gly Pro Arg Leu Pro Arg
1               5                   10                  15

Thr Arg Val Gly Arg Pro Ala Ala Val Arg Leu Leu Leu Leu Leu Gly
            20                  25                  30

Ala Val Leu Asn Pro His Glu Ala Leu Ala Gln Pro Leu Pro Thr Thr
        35                  40                  45

Gly Thr Pro Gly Ser Glu Gly Gly Thr Val Lys Asn Tyr Glu Thr Ala
    50                  55                  60

Val Gln Phe Cys Trp Asn His Tyr Lys Asp Gln Met Asp Pro Ile Glu
65                  70                  75                  80

Lys Asp Trp Cys Asp Trp Ala Met Ile Ser Arg Pro Tyr Ser Thr Leu
                85                  90                  95

Arg Asp Cys Leu Glu His Phe Ala Glu Leu Phe Asp Leu Gly Phe Pro
            100                 105                 110

Asn Pro Leu Ala Glu Arg Ile Ile Phe Glu Thr His Gln Ile His Phe
        115                 120                 125

Ala Asn Cys Ser Leu Val Gln Pro Thr Phe Ser Asp Pro Pro Glu Asp
    130                 135                 140

Val Leu Leu Ala Met Ile Ile Ala Pro Ile Cys Leu Ile Pro Phe Leu
145                 150                 155                 160

Ile Thr Leu Val Val Trp Arg Ser Lys Asp Ser Glu Ala Gln Ala
                165                 170                 175

<210> SEQ ID NO 11
<211> LENGTH: 1312
<212> TYPE: DNA
<213> ORGANISM: Homo sapiens
<220> FEATURE:
<221> NAME/KEY: CDS
<222> LOCATION: (30)..(476)

<400> SEQUENCE: 11
gagcgtgacc cagctgcggc cggccagcc atg gag act gga gcg ctg cgg cgc        53
                                Met Glu Thr Gly Ala Leu Arg Arg
                                1               5 ccg caa ctt ctc ccg ttg ctg ctg ctg ctc tgc ggt ggg tgt ccc aga        101
Pro Gln Leu Leu Pro Leu Leu Leu Leu Leu Cys Gly Gly Cys Pro Arg
        10                  15                  20 gca ggc ggc tgc aac gag aca ggc atg ttg gag agg ctg ccc ctg tgt       149
Ala Gly Gly Cys Asn Glu Thr Gly Met Leu Glu Arg Leu Pro Leu Cys
```

```
              25                  30                  35                  40
ggg aag gct ttc gca gac atg atg ggc aag gtg gac gtc tgg aag tgg        197
Gly Lys Ala Phe Ala Asp Met Met Gly Lys Val Asp Val Trp Lys Trp
                    45                  50                  55 tgc aac ctg tcc gag ttc atc gtg tac tat gag agt ttc acc aac tgc        245
Cys Asn Leu Ser Glu Phe Ile Val Tyr Tyr Glu Ser Phe Thr Asn Cys
             60                  65                  70 acc gag atg gag gcc aat gtc gtg ggc tgc tac tgg ccc aac ccc ctg        293
Thr Glu Met Glu Ala Asn Val Val Gly Cys Tyr Trp Pro Asn Pro Leu
         75                  80                  85 gcc cag ggc ttc atc acc ggc atc cac agg cag ttc ttc tcc aac tgc        341
Ala Gln Gly Phe Ile Thr Gly Ile His Arg Gln Phe Phe Ser Asn Cys
     90                  95                 100 acc gtg gac agg gtc cac ttg gag gac ccc cca gac gag gtt ctc atc        389
Thr Val Asp Arg Val His Leu Glu Asp Pro Pro Asp Glu Val Leu Ile
105                 110                 115                 120 ccg ctg atc gtt ata ccc gtc gtt ctg act gtc gcc atg gct ggc ctg        437
Pro Leu Ile Val Ile Pro Val Val Leu Thr Val Ala Met Ala Gly Leu
                125                 130                 135 gtg gtg tgg cgc agc aaa cgc acc gac acg ctg ctg tga gggtcccggt         486
Val Val Trp Arg Ser Lys Arg Thr Asp Thr Leu Leu
                140                 145 gagatggagt gggtcacacc tggcaagctg aagaaagtt ccctggggat gggagatcgg        546
gtgggtgctg ccaatctcca gctactgtgg ccacacccca cctggtcatg gcagacccc        606 tcccttcctg gctgaccctg ctccctcgag gccagcctgc tccctggctg aggctcaggc       666
tatccgccca agtctttgc tcattctagg gccagtggag gaaaatgtga taaggccaga        726
gcttgtgtgc tgggcaagaa atcacctgct gcatcctgtg ctccgcaggc tgggccggaa       786
gcctctgcct gcaggtttct atgctgtttc ttagcacaga atccagccta gccttagccg       846
cagtctaggc cctgcttgga ctaggactcc ttgcttgacc ccatctctgg ttcctgccct       906
ggctcctgca ccagccccag ctcctgccta catccaggca gaaatatagg caggggctct       966
tggaagacgt tccgtgctgt gacctccgag ccctcctggt gggaagacag ctggaaaggc      1026
tgggaggaga agggaggggc tgggggttcc caggagccat gcgtggcctg cagagtccat      1086
tccatcatga tgctgtgccc gctatgggct gtgtccatga ccagaggctg gagtgggggt      1146
gtgttatagc ccctcaccgg gacttgctgt gcggatgggg cctgggcctc cttcctacag      1206
gggctcctct gtgggtgagg ggccctctgg aatggcatcc catgagcttg tggcctctat      1266
ctgctaccat ctgtgtttta tctgagtaaa gttaccttac ttctgg                    1312

<210> SEQ ID NO 12
<211> LENGTH: 148
<212> TYPE: PRT
<213> ORGANISM: Homo sapiens

<400> SEQUENCE: 12

Met Glu Thr Gly Ala Leu Arg Arg Pro Gln Leu Leu Pro Leu Leu Leu
1               5                  10                  15

Leu Leu Cys Gly Gly Cys Pro Arg Ala Gly Gly Cys Asn Glu Thr Gly
             20                  25                  30

Met Leu Glu Arg Leu Pro Leu Cys Gly Lys Ala Phe Ala Asp Met Met
         35                  40                  45

Gly Lys Val Asp Val Trp Lys Trp Cys Asn Leu Ser Glu Phe Ile Val
     50                  55                  60

Tyr Tyr Glu Ser Phe Thr Asn Cys Thr Glu Met Glu Ala Asn Val Val
```

```
                    65                  70                  75                  80
Gly Cys Tyr Trp Pro Asn Pro Leu Ala Gln Gly Phe Ile Thr Gly Ile
                        85                  90                  95

His Arg Gln Phe Phe Ser Asn Cys Thr Val Asp Arg Val His Leu Glu
                100                 105                 110

Asp Pro Pro Asp Glu Val Leu Ile Pro Leu Ile Val Ile Pro Val Val
                115                 120                 125

Leu Thr Val Ala Met Ala Gly Leu Val Val Trp Arg Ser Lys Arg Thr
        130                 135                 140

Asp Thr Leu Leu
145

<210> SEQ ID NO 13
<211> LENGTH: 3539
<212> TYPE: DNA
<213> ORGANISM: Mus musculus
<220> FEATURE:
<221> NAME/KEY: CDS
<222> LOCATION: (2548)..(2697)

<400> SEQUENCE: 13
agatctgccg gggtcgccag gaagaggaca tgagttgtct gtgtccacat caccagggct     60
gggggctagg agctgtcgta ggtcatgtct ttagcttcgg gaccttccgg gagacctgca    120
tgcggagcta cgcctgtcgc ccagtttggc cctagaaggg aagaaagtga actcacggat    180
ctgtgaagag caccagcccg tggcaaacgt gttcgaactg attcatcgtg aattagcaca    240
tatctctggg ctaggcgggg gccggcattc tcccccacc tgatgagaat ggtgacccca     300
gccagaaaac cgagccgctg tgccccagtc ttttgagtcc agactctaca gcttcccacc    360
tttagtgtga ctgggcaata gacttaccct ttcggcactt cactttaatt caagagaaca    420
ccagctcggg agtgtagaga tcaaaagcga ttgggatctg gctgggattt gtcaactgta    480
aagtgattaa catatgtgag gcattagtgt gctcccagtc agtcaatcct cacgtttatg    540
atggatgaat gaaggcagtc aggtcaactc gcaggtcata gccttataag ggataatagt    600
atcacaagga agaaaacaaa actatctctc ttcctaattt tggctattcc tgtatttcca    660
aataggaatg tgagttctga attttcagat aactaccctc tccaaacccc aatttccaat    720
tcagctgttc ccagttctgc ccttattacg aaatccgtac tggctagtct atcgagaaac    780
ccctcagtcc cagtcactgg agactgagcc tctcccttcc aggtgtaccc tgcgggcaca    840 gatggggtc gaggctcagt aggtgctaag ccggcagggg gcgcggtcca tttgaggtca    900
cagctcccca agtccggggt tttggttatc catgtgtccc acccgtctcc cggttcttgc    960
agcactgtcc aggaagctca gatcagcact ctgggttgta cacattatgg gcaaaggatt   1020
caccccaccc gagttgttct ggttcccctt cccttctcac tgtttgaact ctatgctggg   1080
aaattagggc aagggaagtc ctgctccagt ctaatctctc agagcggatc tctgagatgt   1140
ctagccacag gggacctctt accctaccc ccatacccca caggcaagct gcagggcagg    1200 tctggttta gaagcaagca cgctggagag ggaggactcc agggcaaatc tgaccacgcc    1260
caccgtccgc ccctgagcgc ttataagacg ctggagctgg tgctcactag tcagtggttt   1320
cttggtgaca ctagacagag caactccagc gttaccgctc ccgctcctgg tttctcggct   1380
tctcatcgca gtcaatcttg gactttgggg ttttgctact gtcagaagga cttctttctg   1440
cttcaagtgt tgacaacgc accccttat caggtaggaa ccgctggcct ccagcatgtt    1500
agggaggggg acggctttgc caaagcccca aaacttgcag agctggacaa ggggaacaa    1560
```

```
cccactttag ggtatccaat gtagagaaca cctcattgcc caggtctagc tcatgcgcac    1620
agctggagct ctcttgagat cccccctcct ccttgggctg agatcctggg actttagttg    1680
gaaacctctg gaagcctggc acttctcaat ggcttccttt gccttgcttg tcacccaccc    1740
ggccagcgca aaaatctccg tgtttctct gcgccagtgg gggagataag cagctgagcc    1800
aggaagagcg ctgccaagcg gctccccgtc ctgccgccac ccttcgcgtg ctgacgggat    1860
cgtgctgctg gcccggttgc tcacactcgg tgtcttgttc cttccaggg tatcagagca    1920 tcgccacaga atgaagctgg tttccatcac cctgatgtta ttgggttcac tcgctttcct    1980
aggcgcggac actgcagggc cagatactcc ttcgcagttc cgaaagaagt gagtttgggc    2040
cgtgctttct ttcttcactt tgaatacctg gcaatgagag aaaactgaga gatggtctgg    2100
aggtgttaca aagggagtgg agctggctgg acatcactt gaacttaggc caaacgcatc    2160
tgcttgtgtt ttctaggtgg aataagtggg cgctaagtcg tgggaagagg gaactacaag    2220
catccagcag ctaccctacg ggactcgctg atgagacgac agttcctacc cagactcttg    2280
atccattcct ggacgagcag aacacaactg gccccctaca agccaggtaa ctatgctctc    2340
tgcagaggat gtgccctctc cactactctg accctgggga ttgtcctggc tgcactgcag    2400
ctgaggctcc ggcggaggga acgggttcca ggtccctcgg gtactgcatg gctccggtcc    2460
caggtggttg ggaccaaagc cccggttgat gaggtgtcct tccttcttca cagcaatcag    2520
agcgaagccc acattcgtgt caaacgc tac cgc cag agc atg aac cag ggt tcc    2574
                                 Tyr Arg Gln Ser Met Asn Gln Gly Ser
                                  1               5 cgc agc aat gga tgc cgc ttc ggg acc tgc aca ttt cag aaa ttg gcc    2622
Arg Ser Asn Gly Cys Arg Phe Gly Thr Cys Thr Phe Gln Lys Leu Ala
 10              15                  20                  25 cac cag atc tac cag cta aca gac aaa gac aag gac ggc atg gct ccc    2670
His Gln Ile Tyr Gln Leu Thr Asp Lys Asp Lys Asp Gly Met Ala Pro
             30                  35                  40 aga aac aag atc agc cct caa ggc tat ggccgccggc gccggcgttc           2717
Arg Asn Lys Ile Ser Pro Gln Gly Tyr
         45                  50 cctgctggag gtcctccggt cccggactgt ggagtcctcc caggagcaga cacacacagc    2777
cccagccccc tgggcgcaca tctccagact ctttaggata taggtgcggg tgacagcatt    2837
gaacagtcgg gcgagtatcc cgttggcgcc tgcggaatca gagaacttcg caccggggcg    2897
gactgagaca atcctgcaga gatctgcctg gctgccccta ggggaggcag aggaacccaa    2957
gaccaagcca ggctcatgcc agaaaccgag acttacaggc tgatactctc cggggcagggg    3017 tctgagccac tgccttgccc gctcataaac tggtttctca cggggcataa gcctcattac    3077
tacttgaact ttccaaaacc tagcgaggaa cgtgcaatgc ttgttgtcca gccaaaggta    3137
actatagtat ttaagtttgt tgctgtcaag gttttttttt tggtaacttc aaatatatag    3197 agatatttt gtacgttata tattgtatta agggcatttt aaagtgatta tattgtcacc    3257
ttcccctatt ttaagacgtg aatgtctcag caaggtgtaa ggttgtttgg ttccgtgtgt    3317
gtgtgtgtgt gtgtgtgtgt gtgtgtgtgt gtgtaaggtg gagagcgcct gattatcgcc    3377
tgtggatgaa gaaaaaacat tgtgtttcct ataatctatt tacataaaat atgtgatctg    3437
ggaaaaagca aaccaataaa ctgtctcaat gctgattcat tctcggttca tgcatttggg    3497
gaaggatggt ggtctgggtt tgggtcggcc tggaagtgct ga                      3539
```

<210> SEQ ID NO 14

```
<211> LENGTH: 50
<212> TYPE: PRT
<213> ORGANISM: Mus musculus

<400> SEQUENCE: 14

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu Thr
            20                  25                  30

Asp Lys Asp Lys Asp Gly Met Ala Pro Arg Asn Lys Ile Ser Pro Gln
        35                  40                  45

Gly Tyr
    50

<210> SEQ ID NO 15
<211> LENGTH: 4447
<212> TYPE: DNA
<213> ORGANISM: Mus musculus
<220> FEATURE:
<221> NAME/KEY: CDS
<222> LOCATION: (195)..(1586)

<400> SEQUENCE: 15
tgagtctgga gacaattgtg tatgtatact tttcttaaga tattaaaaaa caaatccaag      60
gtcacaggtt gcttattgat agaagagaaa caatacggat agaagagaaa tcagaaaatt     120
gcttatgatt gacaagaaca gctgcagcag ctacctagct tgaacataca gcacatttca     180
tttggactct aata atg gat aaa aag cat ata cta tgt ttt ctg gtt ctc       230
              Met Asp Lys Lys His Ile Leu Cys Phe Leu Val Leu
              1               5                   10 ttg cct ctt aat atg gct ctc atc tca gca gag tcg gaa gaa ggc gtg       278
Leu Pro Leu Asn Met Ala Leu Ile Ser Ala Glu Ser Glu Glu Gly Val
        15                  20                  25 aac caa aca gac ttg gga gtc act aga aac aag atc atg acg gct caa       326
Asn Gln Thr Asp Leu Gly Val Thr Arg Asn Lys Ile Met Thr Ala Gln
    30                  35                  40 tat gaa tgt tac cag aag atc atg cag gac ccc att caa caa gca gaa       374
Tyr Glu Cys Tyr Gln Lys Ile Met Gln Asp Pro Ile Gln Gln Ala Glu
45                  50                  55                  60 ggc ctt tac tgc aat agg acc tgg gac gga tgg cta tgc tgg aat gac       422
Gly Leu Tyr Cys Asn Arg Thr Trp Asp Gly Trp Leu Cys Trp Asn Asp
                65                  70                  75 gtt gca gca ggg acg gaa tca atg cag tac tgc cct gac tat ttt cag       470
Val Ala Ala Gly Thr Glu Ser Met Gln Tyr Cys Pro Asp Tyr Phe Gln
            80                  85                  90 gat ttt gat cct tca gag aag gtt aca aag atc tgt gac caa gat gga       518
Asp Phe Asp Pro Ser Glu Lys Val Thr Lys Ile Cys Asp Gln Asp Gly
        95                  100                 105 cac tgg ttt cgg cat ccg gat agt aat aga aca tgg acc aac tac acc       566
His Trp Phe Arg His Pro Asp Ser Asn Arg Thr Trp Thr Asn Tyr Thr
    110                 115                 120 ctg tgt aat aac agc acg cat gag aaa gtg aag aca gcc ctg aat ctg       614
Leu Cys Asn Asn Ser Thr His Glu Lys Val Lys Thr Ala Leu Asn Leu
125                 130                 135                 140 ttc tac cta act ata att gga cat gga tta tct att gca tct ctg atc       662
Phe Tyr Leu Thr Ile Ile Gly His Gly Leu Ser Ile Ala Ser Leu Ile
                145                 150                 155 atc tct ctc atc ata ttt ttt tac ttc aag agc cta agt tgc caa cgg       710
Ile Ser Leu Ile Ile Phe Phe Tyr Phe Lys Ser Leu Ser Cys Gln Arg
            160                 165                 170
```

```
atc aca ttg cat aaa aac ctg ttc ttt tca ttt att tgt aat tcg att    758
Ile Thr Leu His Lys Asn Leu Phe Phe Ser Phe Ile Cys Asn Ser Ile
        175                 180                 185 gta aca atc atc cac ctc acg gca gtg gcc aat aac cag gcc tta gtg    806
Val Thr Ile Ile His Leu Thr Ala Val Ala Asn Asn Gln Ala Leu Val
    190                 195                 200 gcc aca aat cct gtg agc tgc aaa gtg tct cag ttt atc cat ctc tac    854
Ala Thr Asn Pro Val Ser Cys Lys Val Ser Gln Phe Ile His Leu Tyr
205                 210                 215                 220 ctg atg ggc tgt aac tac ttc tgg atg ctc tgt gaa ggc gtt tac ctg    902
Leu Met Gly Cys Asn Tyr Phe Trp Met Leu Cys Glu Gly Val Tyr Leu
                225                 230                 235 cac aca ctc atc gtg gtg gct gtg ttt gcg gag aag cag cac ttg atg    950
His Thr Leu Ile Val Val Ala Val Phe Ala Glu Lys Gln His Leu Met
            240                 245                 250 tgg tat tat ttt ctc ggc tgg ggg ttt cct ctg ctt cct gcc tgc atc    998
Trp Tyr Tyr Phe Leu Gly Trp Gly Phe Pro Leu Leu Pro Ala Cys Ile
        255                 260                 265 cac gcc att gcc aga agc ttg tat tac aac gac aat tgc tgg atc agc   1046
His Ala Ile Ala Arg Ser Leu Tyr Tyr Asn Asp Asn Cys Trp Ile Ser
    270                 275                 280 tca gac act cat ctc ctc tac att atc cat ggt ccg att tgt gct gct   1094
Ser Asp Thr His Leu Leu Tyr Ile Ile His Gly Pro Ile Cys Ala Ala
285                 290                 295                 300 ttg ttg gta aat ctc ttt ttc cta tta aat att gta cgt gtt ctc atc   1142
Leu Leu Val Asn Leu Phe Phe Leu Leu Asn Ile Val Arg Val Leu Ile
                305                 310                 315 acc aag ttg aaa gtt aca cac caa gtg gaa tcc aat ctc tac atg aaa   1190
Thr Lys Leu Lys Val Thr His Gln Val Glu Ser Asn Leu Tyr Met Lys
            320                 325                 330 gcc gta aga gct act ctc atc ttg gta cca cta ctt ggc att gaa ttt   1238
Ala Val Arg Ala Thr Leu Ile Leu Val Pro Leu Leu Gly Ile Glu Phe
        335                 340                 345 gtg ctt ttt ccg tgg cgg cct gaa gga aag gtt gca gag gag gtg tat   1286
Val Leu Phe Pro Trp Arg Pro Glu Gly Lys Val Ala Glu Glu Val Tyr
    350                 355                 360 gac tat gtc atg cac att ttg atg cac ttt cag ggt ctt ttg gtg gct   1334
Asp Tyr Val Met His Ile Leu Met His Phe Gln Gly Leu Leu Val Ala
365                 370                 375                 380 act att ttc tgc ttc ttt aat gga gag gtt caa gca att ctg aga aga   1382
Thr Ile Phe Cys Phe Phe Asn Gly Glu Val Gln Ala Ile Leu Arg Arg
                385                 390                 395 aat tgg aac cag tat aaa atc caa ttt gga aat ggc ttt tcc cac tct   1430
Asn Trp Asn Gln Tyr Lys Ile Gln Phe Gly Asn Gly Phe Ser His Ser
            400                 405                 410 gat gct ctc cgc agt gca tcc tac aca gtg tca aca atc agt gac atg   1478
Asp Ala Leu Arg Ser Ala Ser Tyr Thr Val Ser Thr Ile Ser Asp Met
        415                 420                 425 caa ggg tac agc cat gac tgc ccc act gaa cac tta aat gga aaa agc   1526
Gln Gly Tyr Ser His Asp Cys Pro Thr Glu His Leu Asn Gly Lys Ser
    430                 435                 440 atc cag gat att gaa aat gtt gcc tta aaa tca gaa aat acg tat gat   1574
Ile Gln Asp Ile Glu Asn Val Ala Leu Lys Ser Glu Asn Thr Tyr Asp
445                 450                 455                 460 cta gtg atg tga aaatatataa aatcacacac ttgaacctat gattttatag       1626
Leu Val Met ccaaaagatt ggatagccag caaatggatt tctggaatac catgaagaaa gccctcaaat 1686 gaaatgggaa ttgtatggat aaatgtttaa caaccctctc tctatggggg agaaaagcct 1746
```

```
caatttatat tgttggccag taactactcc taccataact gatttcaagt taccaacctg    1806
acatcactga atgtgtaatt ggaaagaaaa taagcacaaa caactcccag gagctgacat    1866
gttctggaac ctgcacagca ctgcatgccc tcagagatgg aagtctgtgc acactctcac    1926
ccacactgac cagaactctg ctcttctcat ctgaggagac ctcactcgga cttacagaca    1986
tgaaaggaaa gtttggtttt tgttataaaa ctcctcatcc ttttgtcatt tggtgatagt    2046
gaatggtttg tccagaaaca ctttaaccct ctttataact tctcttgtag actagacaaa    2106
gagttcatta tctctgtggt ctcatgttac tttctttaag aaaagcaact gagcagaatt    2166
cccatgggct tcttagttgc tgctacatat tgttgtatcc tgtggtatat gcactctgaa    2226
tcactaggga gacatattgg tagaagctac accttgtcgg ctctctctct ctctctctct    2286
ctctctctct ctctctctct ctctctctct cggcaagaat aggaggaaat cagttttctg    2346
gaatctgtaa atagaaactt tggccttttcc atttctactg tgtagataag taagtgatca    2406
accattttac atgaagggaa tcaatgaagg atttctttttt atcttgggaa tctgagagag    2466
agagagagag agagagagag agagagagag agagagagag agagagagag agagaggttg    2526
tacaaatgaa actgtaagta ctctgtaatt ttattttatt gtttcaattc aaaacacaac    2586
ctaggtaact tttaaagcag atagatgatg caacattata tgcaacttag tatctgatac    2646
tgtgtctggg ctgatttatt ttatagtaaa atagaatcat gaattctata cttggtaaat    2706
attttaagga caaacagata ccagcatcag aagtttgaga actaaaaaca aaccccagaa    2766
atatcaatga taagatatga aatatttatt taaaaatgta aagccataat tttacaagca    2826
tgatatattt ggtgtgctga catactgctt ccaatatgac atattccaat ttgatgacaa    2886
ctcattcaaa ttcagaaatt atgaacaact actgtaagaa gtgctagtct gctacatttg    2946
tgggctttaa ttcactaaat tatagctttta ctgattttta ctaaatgaag atacatgctt    3006
ttgaaaaaga cccaggttat tattttttta tgaaccacag aggaattttc tctatgtaat    3066
aacactgttt cagtatttca gtagactact gtggatgata atacaagcca cgggaagact    3126
tgaacttacc actcattgag gatgaagtgt cagatattta agtaataatt aaattaagac    3186
agaagaagat tttgcttgtg agtttaagtg acattttaaa tggatttagt ttttccaata    3246
ttgcttggtt tggagtttct gaagaacaag attgacttca gttagtaaaa gtcactctgg    3306
ggacagttac atgagtccat gttttttaaa gtgtgtctgt cagtttacag tggatgagag    3366
gagtgactca gccctcactc attgtcttaa gctatagaag agaataaatt aaaaagttgt    3426
ttgaaactgt caaggaaaag aattcaaatt atcaagcact gatgtattac atgatctgac    3486
agacatattt gtaatttctt tttttttttt tctttctttt tttttatatt tgtaattttc    3546
tgaactttca gctgcttaaa ccgtacaaac cttccttttta ataccttcag actttaggta    3606
ttgattattc atatcttcgc tgacagtgtt cgtgtaattc tgcattcttc taaacaaact    3666
gtcaagtatt aacaataaat ggtagtacag aatgccgaat taccagagaa catacttaaa    3726
aggtattgta attttaagtt ttattatttt tttactatac cgagtgtagc tgagattttt    3786
ttactgccaa tatctactgt ggtgtcattc tcagccatag cagtctaaga ttagtcagta    3846 ttagtttttgt aatagtattt ttgaagctgg atttctctaa agctgaagtg ccaattaaaa    3906
tatttctata atgcttgtag aaaaaaaatc caaaaatttt gaaagaaaac ttctctggtg    3966
cctaaaaatt aacttgggga gttttttagct tttaaaagtt gcatctatta ttttttctcta    4026 atactttgtt agagtcatgg ctgacacttt tagaagcgac tttgtatttt tttgttgata    4086
aaccagcctt cctggaggtt agtgtttttt caaatataac aaactgtgta gggtttagga    4146
```

```
gtagtcagtg ttatacttac tgtttagata ttttaatgtg aatctatttt aatttccttt    4206
gtgttttaat ttgctcatag aaacattata tgtaaaacat actcaagttc acttaaaaga    4266
actcatattt tatcgacata aaatctctac ttaggttta tgagaatatt aaagttgtaa     4326
gttatcactc actttcacgc atcctccctg gactatagag caattgaatt cctcacaaaa    4386
ttcttgcagc aaataaagaa atactttgca aaataaaaaa aaaaaaaaaa aaaaaaaaa     4446 a                                                                    4447
```

<210> SEQ ID NO 16
<211> LENGTH: 463
<212> TYPE: PRT
<213> ORGANISM: Mus musculus

<400> SEQUENCE: 16

```
Met Asp Lys Lys His Ile Leu Cys Phe Leu Val Leu Pro Leu Asn
1               5                   10                  15

Met Ala Leu Ile Ser Ala Glu Ser Glu Glu Gly Val Asn Gln Thr Asp
            20                  25                  30

Leu Gly Val Thr Arg Asn Lys Ile Met Thr Ala Gln Tyr Glu Cys Tyr
        35                  40                  45

Gln Lys Ile Met Gln Asp Pro Ile Gln Ala Glu Gly Leu Tyr Cys
    50                  55                  60

Asn Arg Thr Trp Asp Gly Trp Leu Cys Trp Asn Asp Val Ala Ala Gly
65                  70                  75                  80

Thr Glu Ser Met Gln Tyr Cys Pro Asp Tyr Phe Gln Asp Phe Asp Pro
                85                  90                  95

Ser Glu Lys Val Thr Lys Ile Cys Asp Gln Asp Gly His Trp Phe Arg
            100                 105                 110

His Pro Asp Ser Asn Arg Thr Trp Thr Asn Tyr Thr Leu Cys Asn Asn
        115                 120                 125

Ser Thr His Glu Lys Val Lys Thr Ala Leu Asn Leu Phe Tyr Leu Thr
    130                 135                 140

Ile Ile Gly His Gly Leu Ser Ile Ala Ser Leu Ile Ile Ser Leu Ile
145                 150                 155                 160

Ile Phe Phe Tyr Phe Lys Ser Leu Ser Cys Gln Arg Ile Thr Leu His
                165                 170                 175

Lys Asn Leu Phe Phe Ser Phe Ile Cys Asn Ser Ile Val Thr Ile Ile
            180                 185                 190

His Leu Thr Ala Val Ala Asn Asn Gln Ala Leu Val Ala Thr Asn Pro
        195                 200                 205

Val Ser Cys Lys Val Ser Gln Phe Ile His Leu Tyr Leu Met Gly Cys
    210                 215                 220

Asn Tyr Phe Trp Met Leu Cys Glu Gly Val Tyr Leu His Thr Leu Ile
225                 230                 235                 240

Val Val Ala Val Phe Ala Glu Lys Gln His Leu Met Trp Tyr Tyr Phe
                245                 250                 255

Leu Gly Trp Gly Phe Pro Leu Leu Pro Ala Cys Ile His Ala Ile Ala
            260                 265                 270

Arg Ser Leu Tyr Tyr Asn Asp Asn Cys Trp Ile Ser Ser Asp Thr His
        275                 280                 285

Leu Leu Tyr Ile Ile His Gly Pro Ile Cys Ala Ala Leu Leu Val Asn
    290                 295                 300

Leu Phe Phe Leu Leu Asn Ile Val Arg Val Leu Ile Thr Lys Leu Lys
```

```
                305                 310                 315                 320
Val Thr His Gln Val Glu Ser Asn Leu Tyr Met Lys Ala Val Arg Ala
                    325                 330                 335

Thr Leu Ile Leu Val Pro Leu Leu Gly Ile Glu Phe Val Leu Phe Pro
                    340                 345                 350

Trp Arg Pro Glu Gly Lys Val Ala Glu Glu Val Tyr Asp Tyr Val Met
                    355                 360                 365

His Ile Leu Met His Phe Gln Gly Leu Leu Val Ala Thr Ile Phe Cys
                    370                 375                 380

Phe Phe Asn Gly Glu Val Gln Ala Ile Leu Arg Arg Asn Trp Asn Gln
385                 390                 395                 400

Tyr Lys Ile Gln Phe Gly Asn Gly Phe Ser His Ser Asp Ala Leu Arg
                    405                 410                 415

Ser Ala Ser Tyr Thr Val Ser Thr Ile Ser Asp Met Gln Gly Tyr Ser
                    420                 425                 430

His Asp Cys Pro Thr Glu His Leu Asn Gly Lys Ser Ile Gln Asp Ile
                    435                 440                 445

Glu Asn Val Ala Leu Lys Ser Glu Asn Thr Tyr Asp Leu Val Met
                450                 455                 460

<210> SEQ ID NO 17
<211> LENGTH: 1568
<212> TYPE: DNA
<213> ORGANISM: Mus musculus
<220> FEATURE:
<221> NAME/KEY: CDS
<222> LOCATION: (111)..(1298)

<400> SEQUENCE: 17
agcgcctgct ccgcaaagct gcctctgcag cctcctggca ctaacagccc catccacagg      60
ctccccggga caggtgctcc aagagaaat ccagacccaa gttggccctc atg tca        116
                                                      Met Ser
                                                        1 gtc ata ccc agc ccc agg ccc gtc tcc acc ttg gaa ccg gac aat gat      164
Val Ile Pro Ser Pro Arg Pro Val Ser Thr Leu Glu Pro Asp Asn Asp
          5                  10                  15 ttt aga gac atc cac aac tgg aca gag ctg ctc cac ctc ttc aac cag      212
Phe Arg Asp Ile His Asn Trp Thr Glu Leu Leu His Leu Phe Asn Gln
 20                  25                  30 acc ttt acc gat tgc cac ata gaa ttc aac gag aac acc aaa cac gtg      260
Thr Phe Thr Asp Cys His Ile Glu Phe Asn Glu Asn Thr Lys His Val
35                  40                  45                  50 gtc ctc ttc gtc ttc tac ctg gcc atc ttt gtg gta ggc tta gta gag      308
Val Leu Phe Val Phe Tyr Leu Ala Ile Phe Val Val Gly Leu Val Glu
                55                  60                  65 aac gtc ctg gtg ata tgt gtc aac tgc cgc cgt tca ggc cgg gtg ggg      356
Asn Val Leu Val Ile Cys Val Asn Cys Arg Arg Ser Gly Arg Val Gly
        70                  75                  80 atg ctg aac ctg tac atc ctc aac atg gcc atc gca gac ctg ggc atc      404
Met Leu Asn Leu Tyr Ile Leu Asn Met Ala Ile Ala Asp Leu Gly Ile
    85                  90                  95 atc ctg tct ctg cct gtt tgg atg ctg gag gtc atg ctg gag tac act      452
Ile Leu Ser Leu Pro Val Trp Met Leu Glu Val Met Leu Glu Tyr Thr
100                 105                 110 tgg ctc tgg ggc agc ttc tcc tgt cgc ttc att cat tat ttc tac ctt      500
Trp Leu Trp Gly Ser Phe Ser Cys Arg Phe Ile His Tyr Phe Tyr Leu
115                 120                 125                 130 gtc aac atg tac agc agc atc ttc ttc ctg acg tgc ctc agc att gac      548
```

```
                Val Asn Met Tyr Ser Ser Ile Phe Phe Leu Thr Cys Leu Ser Ile Asp
                                135                 140                 145 cgc tac gtc acc ctc acc aac acc tct ccc tcc tgg cag cgc cac cag          596
Arg Tyr Val Thr Leu Thr Asn Thr Ser Pro Ser Trp Gln Arg His Gln
            150                 155                 160 cac cga ata cgg agg gcc gtg tgc gca ggc gtc tgg gtc ctc tcc gcc          644
His Arg Ile Arg Arg Ala Val Cys Ala Gly Val Trp Val Leu Ser Ala
            165                 170                 175 att atc cca ctg ccg gag gtg gtg cac atc cag ctg ttg gat ggc tcc          692
Ile Ile Pro Leu Pro Glu Val Val His Ile Gln Leu Leu Asp Gly Ser
        180                 185                 190 gag ccc atg tgc ctc ttc cta gca cct ttt gaa acg tac agc gcc tgg          740
Glu Pro Met Cys Leu Phe Leu Ala Pro Phe Glu Thr Tyr Ser Ala Trp
195                 200                 205                 210 gcc ctg gca gtg gcc ctg tcg gcc acc atc ctg ggc ttc cta ctg cct          788
Ala Leu Ala Val Ala Leu Ser Ala Thr Ile Leu Gly Phe Leu Leu Pro
            215                 220                 225 ttt ctt ctc atc gca gtg ttc aat atc ctg aca gcc tgc cgg ctt cgg          836
Phe Leu Leu Ile Ala Val Phe Asn Ile Leu Thr Ala Cys Arg Leu Arg
            230                 235                 240 agg caa agg cag acg gag agc agg cgc cac tgc ctg ttg atg tgg gct          884
Arg Gln Arg Gln Thr Glu Ser Arg Arg His Cys Leu Leu Met Trp Ala
        245                 250                 255 tac ata gtt gtc ttt gcc atc tgc tgg ctg ccc tac caa gtg act atg          932
Tyr Ile Val Val Phe Ala Ile Cys Trp Leu Pro Tyr Gln Val Thr Met
    260                 265                 270 ctg ctc act ctg cac ggg acc cac atc ttc ctc cac tgt cac ctg              980
Leu Leu Thr Leu His Gly Thr His Ile Phe Leu His Cys His Leu
275                 280                 285                 290 gtt aac ctt ctc tac ttc ttc tac gaa atc atc gac tgc ttt tcc atg         1028
Val Asn Leu Leu Tyr Phe Phe Tyr Glu Ile Ile Asp Cys Phe Ser Met
            295                 300                 305 ctg cac tgt gtg gcc aac ccc atc ctc tac aac ttt ctc agc ccg agc         1076
Leu His Cys Val Ala Asn Pro Ile Leu Tyr Asn Phe Leu Ser Pro Ser
            310                 315                 320 ttc cgg ggc cga ctg ctg agc ctt gtg gtc cgt tac ctt ccc aag gag         1124
Phe Arg Gly Arg Leu Leu Ser Leu Val Val Arg Tyr Leu Pro Lys Glu
        325                 330                 335 cag gcc agg gca gca ggt ggt cga gcc tcc tct tct tct tcc acc cag         1172
Gln Ala Arg Ala Ala Gly Gly Arg Ala Ser Ser Ser Ser Ser Thr Gln
340                 345                 350 cac tcc atc atc att acc aaa gag ggc agc ctg ccg ctg cag cgg atc         1220
His Ser Ile Ile Ile Thr Lys Glu Gly Ser Leu Pro Leu Gln Arg Ile
355                 360                 365                 370 tcc aca ccc acc cca tcc gaa acg ttc agg cgt cct ctc cgc ctc caa         1268
Ser Thr Pro Thr Pro Ser Glu Thr Phe Arg Arg Pro Leu Arg Leu Gln
            375                 380                 385 aca cct cac cta cac tct gca att ctg tag ccagctaagg tagactctag           1318
Thr Pro His Leu His Ser Ala Ile Leu
        390                 395 cttcctccac caacaagaaa gttcagaggg ggatgcgaga ggtctgtggg aggggggtggg       1378 aaggactggc ttgttcaggg ccaatttaag tatatcaaaa tgttgctgtg gggagaggga       1438
aacggttcgg gaaggacaga gaatggatct ttccttgata gtacactatt tgtttgggta       1498
ctgatgtcta agggagccac accggtgggg cgtggggggt ggggaaccga aataaataaa       1558
tcatagagac                                                             1568

<210> SEQ ID NO 18
```

```
<211> LENGTH: 395
<212> TYPE: PRT
<213> ORGANISM: Mus musculus

<400> SEQUENCE: 18

Met Ser Val Ile Pro Ser Pro Arg Pro Val Ser Thr Leu Glu Pro Asp
1               5                   10                  15

Asn Asp Phe Arg Asp Ile His Asn Trp Thr Glu Leu Leu His Leu Phe
            20                  25                  30

Asn Gln Thr Phe Thr Asp Cys His Ile Glu Phe Asn Glu Asn Thr Lys
        35                  40                  45

His Val Val Leu Phe Val Phe Tyr Leu Ala Ile Phe Val Val Gly Leu
    50                  55                  60

Val Glu Asn Val Leu Val Ile Cys Val Asn Cys Arg Arg Ser Gly Arg
65                  70                  75                  80

Val Gly Met Leu Asn Leu Tyr Ile Leu Asn Met Ala Ile Ala Asp Leu
                85                  90                  95

Gly Ile Ile Leu Ser Leu Pro Val Trp Met Leu Glu Val Met Leu Glu
            100                 105                 110

Tyr Thr Trp Leu Trp Gly Ser Phe Ser Cys Arg Phe Ile His Tyr Phe
        115                 120                 125

Tyr Leu Val Asn Met Tyr Ser Ser Ile Phe Phe Leu Thr Cys Leu Ser
    130                 135                 140

Ile Asp Arg Tyr Val Thr Leu Thr Asn Thr Ser Pro Ser Trp Gln Arg
145                 150                 155                 160

His Gln His Arg Ile Arg Arg Ala Val Cys Ala Gly Val Trp Val Leu
                165                 170                 175

Ser Ala Ile Ile Pro Leu Pro Glu Val Val His Ile Gln Leu Leu Asp
            180                 185                 190

Gly Ser Glu Pro Met Cys Leu Phe Leu Ala Pro Phe Glu Thr Tyr Ser
        195                 200                 205

Ala Trp Ala Leu Ala Val Ala Leu Ser Ala Thr Ile Leu Gly Phe Leu
    210                 215                 220

Leu Pro Phe Leu Leu Ile Ala Val Phe Asn Ile Leu Thr Ala Cys Arg
225                 230                 235                 240

Leu Arg Arg Gln Arg Gln Thr Glu Ser Arg Arg His Cys Leu Leu Met
                245                 250                 255

Trp Ala Tyr Ile Val Val Phe Ala Ile Cys Trp Leu Pro Tyr Gln Val
            260                 265                 270

Thr Met Leu Leu Leu Thr Leu His Gly Thr His Ile Phe Leu His Cys
        275                 280                 285

His Leu Val Asn Leu Leu Tyr Phe Phe Tyr Glu Ile Ile Asp Cys Phe
    290                 295                 300

Ser Met Leu His Cys Val Ala Asn Pro Ile Leu Tyr Asn Phe Leu Ser
305                 310                 315                 320

Pro Ser Phe Arg Gly Arg Leu Ser Leu Val Val Arg Tyr Leu Pro
                325                 330                 335

Lys Glu Gln Ala Arg Ala Ala Gly Gly Arg Ala Ser Ser Ser Ser
            340                 345                 350

Thr Gln His Ser Ile Ile Ile Thr Lys Glu Gly Ser Leu Pro Leu Gln
        355                 360                 365

Arg Ile Ser Thr Pro Thr Pro Ser Glu Thr Phe Arg Arg Pro Leu Arg
    370                 375                 380

Leu Gln Thr Pro His Leu His Ser Ala Ile Leu
```

```
385            390            395

<210> SEQ ID NO 19
<211> LENGTH: 848
<212> TYPE: DNA
<213> ORGANISM: Mus musculus
<220> FEATURE:
<221> NAME/KEY: CDS
<222> LOCATION: (60)..(506)

<400> SEQUENCE: 19
ggcacgagga gcgggcgcag agctcggcaa ggcgctggga cggtggggct ctgcttgcc        59 atg gcc ccg ggc ctg cgg ggc ctc ccg cgg tgc ggc ctc tgg ctg ctg       107
Met Ala Pro Gly Leu Arg Gly Leu Pro Arg Cys Gly Leu Trp Leu Leu
1               5                   10                  15 ctg gct cac cat ctc ttc atg gtc act gcc tgc cgg gac cct gac tat       155
Leu Ala His His Leu Phe Met Val Thr Ala Cys Arg Asp Pro Asp Tyr
             20                  25                  30 ggg act ctc atc cag gag ctg tgc ctc agc cgc ttc aag gag aac atg       203
Gly Thr Leu Ile Gln Glu Leu Cys Leu Ser Arg Phe Lys Glu Asn Met
         35                  40                  45 gag act att ggg aag acg cta tgg tgt gac tgg gga aag acc ata cag       251
Glu Thr Ile Gly Lys Thr Leu Trp Cys Asp Trp Gly Lys Thr Ile Gln
     50                  55                  60 agc tat ggg gag ctc act tac tgc acc aag cac gtg gcg cac acg att       299
Ser Tyr Gly Glu Leu Thr Tyr Cys Thr Lys His Val Ala His Thr Ile
65                  70                  75                  80 ggc tgt ttc tgg ccc aat ccg gaa gtg gac aga ttc ttc atc gct gtc       347
Gly Cys Phe Trp Pro Asn Pro Glu Val Asp Arg Phe Phe Ile Ala Val
                 85                  90                  95 cac cat cga tac ttc agc aag tgc ccc atc tcg ggc agg gcc ctg cgg       395
His His Arg Tyr Phe Ser Lys Cys Pro Ile Ser Gly Arg Ala Leu Arg
            100                 105                 110 gac cct ccc aac agc atc ctc tgc cct ttc att gcg ctc ccc att acg       443
Asp Pro Pro Asn Ser Ile Leu Cys Pro Phe Ile Ala Leu Pro Ile Thr
        115                 120                 125 gtc acg ctg ctc atg act gca ctg gtg gtc tgg agg agc aag cgc aca       491
Val Thr Leu Leu Met Thr Ala Leu Val Val Trp Arg Ser Lys Arg Thr
    130                 135                 140 gag ggc atc gtg tag gtatcccagg tgatgaggga ttggggaacc atgggcctag      546
Glu Gly Ile Val
145 cccagcaaca gcatcaggag caggtcccac cttgcatcct gctctagcct agttagcaca      606 ggacttgaga gtggctctgc attaagctga atatgcccta gccagaggct tctagcaggg      666 gagcaggggc ctgcctctgc ttacctctga gattgttcta agcaccaggt ctctggtaca      726 cttcatcacc actgtgggca ttctgaactc caaggaagac tgcacagatg tgtttgtaga      786 tgcacagttt gtgattaaaa gagtattctt aaacctggaa aaaaaaaaa aaaaaaaa         846 aa                                                                    848

<210> SEQ ID NO 20
<211> LENGTH: 148
<212> TYPE: PRT
<213> ORGANISM: Mus musculus

<400> SEQUENCE: 20

Met Ala Pro Gly Leu Arg Gly Leu Pro Arg Cys Gly Leu Trp Leu Leu
1               5                   10                  15

Leu Ala His His Leu Phe Met Val Thr Ala Cys Arg Asp Pro Asp Tyr
```

```
            20                  25                  30
Gly Thr Leu Ile Gln Glu Leu Cys Leu Ser Arg Phe Lys Glu Asn Met
     35                  40                  45

Glu Thr Ile Gly Lys Thr Leu Trp Cys Asp Trp Gly Lys Thr Ile Gln
 50                  55                  60

Ser Tyr Gly Glu Leu Thr Tyr Cys Thr Lys His Val Ala His Thr Ile
 65                  70                  75                  80

Gly Cys Phe Trp Pro Asn Pro Glu Val Asp Arg Phe Phe Ile Ala Val
                 85                  90                  95

His His Arg Tyr Phe Ser Lys Cys Pro Ile Ser Gly Arg Ala Leu Arg
            100                 105                 110

Asp Pro Pro Asn Ser Ile Leu Cys Pro Phe Ile Ala Leu Pro Ile Thr
            115                 120                 125

Val Thr Leu Leu Met Thr Ala Leu Val Val Trp Arg Ser Lys Arg Thr
        130                 135                 140

Glu Gly Ile Val
145

<210> SEQ ID NO 21
<211> LENGTH: 995
<212> TYPE: DNA
<213> ORGANISM: Mus musculus
<220> FEATURE:
<221> NAME/KEY: CDS
<222> LOCATION: (22)..(591)

<400> SEQUENCE: 21
cgccatctca cccaaggcgt g atg gcc ccg ctc cgg gta gag cgc gcc ccg          51
                       Met Ala Pro Leu Arg Val Glu Arg Ala Pro
                        1               5                  10 ggt gga tct cgg ctt ggt gtg acc cgc gcc cag cgg ccg aca gcg ttg          99
Gly Gly Ser Arg Leu Gly Val Thr Arg Ala Gln Arg Pro Thr Ala Leu
            15                  20                  25 tgc ctc cct ccg ctg ttg ctg ctg ctg ctg ctg ctg ggc gct gtc             147
Cys Leu Pro Pro Leu Leu Leu Leu Leu Leu Leu Leu Gly Ala Val
        30                  35                  40 tca gcc tct ccg gag tcc ctg aac caa tct ctt ccg gag tcc cag aat         195
Ser Ala Ser Pro Glu Ser Leu Asn Gln Ser Leu Pro Glu Ser Gln Asn
    45                  50                  55 caa tct cat ccc act gag gac agc ctt gtg tca aaa ggg aag atg gaa         243
Gln Ser His Pro Thr Glu Asp Ser Leu Val Ser Lys Gly Lys Met Glu
 60                  65                  70 gac tac gaa aca cat gtc cta cct tgc tgg tat gag tac aag agt tgc         291
Asp Tyr Glu Thr His Val Leu Pro Cys Trp Tyr Glu Tyr Lys Ser Cys
 75                  80                  85                  90 atg gac tct gtc aag gac tgg tgc aac tgg act ttg att agc agg cat         339
Met Asp Ser Val Lys Asp Trp Cys Asn Trp Thr Leu Ile Ser Arg His
             95                 100                 105 tac agc gac ctg cag aac tgc ttg gaa tac aat gca gac aag ttt ggg         387
Tyr Ser Asp Leu Gln Asn Cys Leu Glu Tyr Asn Ala Asp Lys Phe Gly
        110                 115                 120 ctg ggc ttc cca aat ccc ttg gca gaa aac atc atc ctt gag gct cac         435
Leu Gly Phe Pro Asn Pro Leu Ala Glu Asn Ile Ile Leu Glu Ala His
        125                 130                 135 ctg ata cac ttt gcg aac tgc tcc ctg gtg cag ccc acc ttc tct gat         483
Leu Ile His Phe Ala Asn Cys Ser Leu Val Gln Pro Thr Phe Ser Asp
        140                 145                 150 ccc cca gag gat gtg ctc ctg gcc atg atc ata gcc ccc atc tgc ctc         531
Pro Pro Glu Asp Val Leu Leu Ala Met Ile Ile Ala Pro Ile Cys Leu
```

```
                      155                 160                 165                 170
atc ccg ttc ctt gtt act ctt gtg gtg tgg agg agt aaa gac agc gat           579
Ile Pro Phe Leu Val Thr Leu Val Val Trp Arg Ser Lys Asp Ser Asp
                175                 180                 185 gcc cag gcc tag ggtccatttc tcagcagcca ttttcccccc cttttccctg               631
Ala Gln Ala ctggaaccag gaatggcgct cctcccctcc ctacccactt actctcatcc ttcccacaga         691
cctgtggatt ggtggaaatg gcagcaaagg ggactcacga cacaatgttt gtagtcttta         751
aaataaagtt atgttttggg agagcagagc agcgtagagc agcacagctg agctcgtgag         811
gcaggagact cagcccgagg aaatcgcaga taagttttta attaaaaaga ttgagcagta         871
aaaagaatta gaactctaaa cttaagctaa tagagtagct tatcgaaata ttacttagtc         931
ttaataatct aagaagatct taagagataa catgaaggct tatttaaaca gtttgaaaaa         991
aaaa                                                                      995

<210> SEQ ID NO 22
<211> LENGTH: 189
<212> TYPE: PRT
<213> ORGANISM: Mus musculus

<400> SEQUENCE: 22

Met Ala Pro Leu Arg Val Glu Arg Ala Pro Gly Gly Ser Arg Leu Gly
1               5                   10                  15

Val Thr Arg Ala Gln Arg Pro Thr Ala Leu Cys Leu Pro Pro Leu Leu
            20                  25                  30

Leu Leu Leu Leu Leu Leu Gly Ala Val Ser Ala Ser Pro Glu Ser
        35                  40                  45

Leu Asn Gln Ser Leu Pro Glu Ser Gln Asn Gln Ser His Pro Thr Glu
    50                  55                  60

Asp Ser Leu Val Ser Lys Gly Lys Met Glu Asp Tyr Glu Thr His Val
65                  70                  75                  80

Leu Pro Cys Trp Tyr Glu Tyr Lys Ser Cys Met Asp Ser Val Lys Asp
                85                  90                  95

Trp Cys Asn Trp Thr Leu Ile Ser Arg His Tyr Ser Asp Leu Gln Asn
            100                 105                 110

Cys Leu Glu Tyr Asn Ala Asp Lys Phe Gly Leu Gly Phe Pro Asn Pro
        115                 120                 125

Leu Ala Glu Asn Ile Ile Leu Glu Ala His Leu Ile His Phe Ala Asn
    130                 135                 140

Cys Ser Leu Val Gln Pro Thr Phe Ser Asp Pro Glu Asp Val Leu
145                 150                 155                 160

Leu Ala Met Ile Ile Ala Pro Ile Cys Leu Ile Pro Phe Leu Val Thr
                165                 170                 175

Leu Val Val Trp Arg Ser Lys Asp Ser Asp Ala Gln Ala
            180                 185

<210> SEQ ID NO 23
<211> LENGTH: 1242
<212> TYPE: DNA
<213> ORGANISM: Mus musculus
<220> FEATURE:
<221> NAME/KEY: CDS
<222> LOCATION: (42)..(485)

<400> SEQUENCE: 23 tatccgctg ttgctgcaag ccggctgcat cttagttggc c atg aag acc cca gca        56
```

```
                                  Met Lys Thr Pro Ala
                                   1               5 cag cgg ctg cac ctt ctt cca ctg ttg ctg ctt tgt ggt gag tgt       104
Gln Arg Leu His Leu Leu Pro Leu Leu Leu Leu Cys Gly Glu Cys
             10                  15                  20 gcc cag gta tgc ggc tgc aac gag aca ggg atg ctg gag agg ctg cct   152
Ala Gln Val Cys Gly Cys Asn Glu Thr Gly Met Leu Glu Arg Leu Pro
             25                  30                  35 cgc tgt ggg aaa gcc ttc gct gac atg atg cag aag gtg gct gtc tgg   200
Arg Cys Gly Lys Ala Phe Ala Asp Met Met Gln Lys Val Ala Val Trp
             40                  45                  50 aag tgg tgc aac ctg tcg gag ttc atc gtg tat tat gaa agc ttc act   248
Lys Trp Cys Asn Leu Ser Glu Phe Ile Val Tyr Tyr Glu Ser Phe Thr
     55                  60                  65 aac tgc acc gag atg gag acc aac atc atg ggc tgc tac tgg ccc aac   296
Asn Cys Thr Glu Met Glu Thr Asn Ile Met Gly Cys Tyr Trp Pro Asn
 70                  75                  80                  85 ccg ctg gcc cag agc ttc atc act gga atc cac agg cag ttc ttt tcc   344
Pro Leu Ala Gln Ser Phe Ile Thr Gly Ile His Arg Gln Phe Phe Ser
                 90                  95                 100 aac tgc acg gtg gac agg acc cac tgg gaa gac ccc ccg gat gaa gta   392
Asn Cys Thr Val Asp Arg Thr His Trp Glu Asp Pro Pro Asp Glu Val
                105                 110                 115 ctc atc cca ctg atc gcg gtt cct gtc gtg ctg act gtg gct atg gct   440
Leu Ile Pro Leu Ile Ala Val Pro Val Val Leu Thr Val Ala Met Ala
                120                 125                 130 ggc ctg gtg gtg tgg cgc agc aag cac act gat cgg ctg ctg tga       485
Gly Leu Val Val Trp Arg Ser Lys His Thr Asp Arg Leu Leu
            135                 140                 145 ggatctgctg gatggagggc catgcctggc aggctgggag aatgttgctc agagctctga  545
gagctggcag actcggcttc tgtctggttt gctttggcca cccctacct ggccatgcca  605 aagtcctccc gaccaggctg gtgtggcccct tgctgtctag cctgccgcct gctgggttc  665 agattgtcca tactttgctc tttcttgggc tagtggaaga aagtgacaaa tcccaagttt  725
gtggaccagg catggaaatc aactgttgct gagccccgct ccccaggctc ggttccctag  785
tttctagccg tttcttggca gagtcttgct cagcctgaac cccgcccag gtcctgaccc   845 atttctagtc ctgaccctga cccctgctac acttggccag agagggcagg caaggtcatc  905
tggaagatgt ggacgccccc ccgcctctat tcaagagact gagcacatca tttatcagac  965
atgaaggata gcctggggtc attaggagcc acgtgtgacc tactgaccca cctgcctgtc 1025 ctctctgtga tctgtcacga ttctgtgtcc agtgtgggct ggagctgtgg cttgtttagc 1085 ccttcaaaga cacctaccct gcaggtagag cgtgaacctc cttcttgagg ggtattcctg 1145 ggagtggggc gcactgagtg tgctcaaggg ttctgtctgc tgatgtcagt tcttttttgat 1205 taaagtgtct ccttacaaaa aaaaaaaaa aaaaaa                              1242

<210> SEQ ID NO 24
<211> LENGTH: 147
<212> TYPE: PRT
<213> ORGANISM: Mus musculus

<400> SEQUENCE: 24

Met Lys Thr Pro Ala Gln Arg Leu His Leu Leu Pro Leu Leu Leu Leu
 1               5                  10                  15

Leu Cys Gly Glu Cys Ala Gln Val Cys Gly Cys Asn Glu Thr Gly Met
             20                  25                  30
```

-continued

```
Leu Glu Arg Leu Pro Arg Cys Gly Lys Ala Phe Ala Asp Met Met Gln
        35                  40                  45
Lys Val Ala Val Trp Lys Trp Cys Asn Leu Ser Glu Phe Ile Val Tyr
     50                  55                  60
Tyr Glu Ser Phe Thr Asn Cys Thr Glu Met Glu Thr Asn Ile Met Gly
65                       70                  75                  80
Cys Tyr Trp Pro Asn Pro Leu Ala Gln Ser Phe Ile Thr Gly Ile His
                 85                  90                  95
Arg Gln Phe Phe Ser Asn Cys Thr Val Asp Arg Thr His Trp Glu Asp
            100                 105                 110
Pro Pro Asp Glu Val Leu Ile Pro Leu Ile Ala Val Pro Val Val Leu
            115                 120                 125
Thr Val Ala Met Ala Gly Leu Val Val Trp Arg Ser Lys His Thr Asp
        130                 135                 140
Arg Leu Leu
145
```

METHOD FOR SCREENING SUBSTANCE HAVING PROANGIOGENIC EFFECT

This application claims benefit of Japanese Patent Application No. 2005-176580 filed Jun. 16, 2005 and the text of application 2005-176580 is incorporated by reference in its entirety herewith.

TECHNICAL FIELD

The present invention relates to an angiogenesis agent containing adrenomedullin as an active ingredient.

BACKGROUND ART

Ischemic disorders such as myocardial infarction and cerebral infarct are one of the major causes of death. Therefore, as the population ages, the social need for the development of the therapeutic medical is increasing. Recently, angiogenic treatment using gene therapy and bone-marrow mononuclear cell transplantation and the like has been investigated as a novel therapy for the ischemic disorders. Major problem of the current angiogenic treatment includes that it is difficult to keep the vascularized blood vessels intact because of their high vascular permeability due their weakness, which may lead to edema, hemorrhage, and restenosis of the blood vessels once vascularized after the treatment. In addition, the use of the growth factors such as vascular endothelial growth factor (VEGF) to the angiogenic treatment includes the risk of developing the arteriosclerotic disease as well. To develop the angiogenic treatment as a safe and effective standard therapy to the ischemic disorders, it is required to solve aforementioned problems and to improve long-term prognosis after treatment.

Major problems of the treatment of cerebral ischemic disorders in the acute phase are management of cerebral edema as well as relief of ischemia. Main aims of the treatment of the cerebral infarction are to recover the function of nerve cells and to protect the uninjured tissue. In the acute phase of cerebral infarction, cerebral edema occurs at site of infarction and its surrounding. In the severe cerebral edema, expansion of the injured area due to the compression of uninjured tissue against cranium as well as the compression of brain-stem which make vital prognosis worse may occur. For cerebral edema, there is no effective therapy other than the administration of the hyperosmotic substances so far. In spite of its importance, there has been no significant progress in the development of the therapy for cerebral edema occurring in conjunction with cerebral infarction and improved drugs for these decades.

A management of the cerebral edema includes the administration of hyperosmotic substances such as glycerol and mannitol. As reported, meta-analysis showed that the administration of the hyperosmotic agents significantly reduced the mortality rate within 14 days after the onset of cerebral infarction. However, there are doubts about long-term prognosis and functional prognosis. To improve the vital prognosis and the functional prognosis after the treatment, a novel therapy based on the mechanism of the onset of the cerebral edema is expected.

Adrenomedullin (AM) is a peptide consisting of 52 amino acids found by Kitamura and Kangawa et al. in 1993. AM attracted attention as a venotropic agent with vasodilating effect when it has been found, however, subsequent studies revealed that it has a variety of physiological activities such as regulation of the cell migration, regulation of differentiation, anti-inflammatory effect, body fluid volume regulating effect, and cardiac effect.

The present inventors have established the transgenic mice in which AM gene overexpress vascular specifically, AM-knockout mice as well as calcitonin gene related peptide (CGRP) (a family of AM) knockout mice and reported the result of the series of studies (Circulation. 2000; 101: 2309; Circulation. 2001; 104: 1964; Circ Res. 2001, 89, 983; Circ Res. 2002; 90:657; Arterioscler Thromb Vasc Biol. 2002 22: 1310-5; Circulation. 2004; 109:1789; Circ Res. 2004; 95: 415). In addition, it has also been reported that organ injury when ischemia and reperfusion injury occurred in kidney was increased in the heterozygotes of AM-knockout mice, which was suppressed, in contrast, in the transgenic mice, which shows that AM is the physiological active substance with not only vasodilating effect but also organ protective effect. Also, it has also been reported that immature blood vessels and significant abnormality in the blood vessel wall itself were observed in the homozygotes of AM-knockout mice, which were lethal at the 14th embryonic day of embryonic life due to the hemorrhage and the systemic edema (Circulation, 2001; 104; 1964).

DISCLOSURE OF THE INVENTION

The present invention provides an angiogenic agent including adrenomedullin as an active ingredient.

The present inventors intensively studied to solve aforementioned problems. It was found that AM contributes to the maturation and stabilization of the blood vessels and suppression of the vascular permeability. Accordingly, the present invention was accomplished.

First aspect of the present invention provides a stabilizing agent of vascular structure including adrenomedullin as an active agent.

Second aspect of the present invention provides a stabilizing agent of vascular structure including at least one substance selected from the group consisting of a substance inhibiting the activity of adrenomedullin degrading enzyme, an adrenomedullin receptor activity-modifying protein, a calcitonin receptor-like receptor and an adrenomedullin receptor.

Third aspect of the present invention provides the stabilizing agent according to the second aspect of the present invention in which the adrenomedullin receptor activity-modifying protein is RAMP 1, RAMP 2 or RAMP 3.

Fourth aspect of the present invention provides a suppressing agent of vascular permeability including adrenomedullin as the active ingredient.

Fifth aspect of the present invention provides a suppressing agent of vascular permeability including at least one substance selected from the group consisting of a substance inhibiting the activity of adrenomedullin degrading enzyme, an adrenomedullin receptor activity-modifying protein, a calcitonin receptor-like receptor and an adrenomedullin receptor.

Sixth aspect of the present invention provides the suppressing agent according to the fifth aspect of the present invention in which the adrenomedullin receptor activity-modifying protein is RAMP 1, RAMP 2 or RAMP 3.

Seventh aspect of the present invention provides an angiogenesis agent including adrenomedullin as the active ingredient.

Eighth aspect of the present invention provides an angiogenic agent which contains, as the active ingredient, at least one substance selected from the group consisting of a substance inhibiting the activity of adrenomedullin degrading enzyme, an adrenomedullin receptor activity-modifying protein, a calcitonin receptor-like receptor and an adrenomedullin receptor.

Ninth aspect of the present invention provides the angiogenesis agent according to the eighth aspect of the present invention in which the adrenomedullin receptor activity-modifying protein is RAMP 1, RAMP 2 or RAMP 3.

Tenth aspect of the present invention provides the angiogenesis agent according to the seventh aspect of the present invention in which the angiogenesis arises from the stabilization of the vascular structure by adrenomedullin.

Eleventh aspect of the present invention provides the angiogenesis agent according to the seventh aspect of the present invention in which the angiogenesis arises from the suppression of the vascular permeability by adrenomedullin.

Twelfth aspect of the present invention provides the angiogenesis agent according to the seventh to eleventh aspects of the present invention for treating or preventing ischemic disorders or edema.

Thirteenth aspect of the present invention provides the angiogenesis agent according to the twelfth aspect of the present invention in which the ischemic disorder is selected from the group consisting of cerebral infarction, myocardial infarction, angina pectoris, arteriosclerosis obliterans, and Buerger's disease.

Fourteenth aspect of the present invention provides the angiogenesis agent according to the twelfth aspect of the present invention in which the edema is cerebral edema.

Fifteenth aspect of the present invention provides a pharmaceutical composition for combination therapy for ischemic disorders or edema comprising adrenomedullin, at least one substance selected from the group consisting of angiogenesis enhancing factor, a substance inhibiting the activity of adrenomedullin degrading enzyme, an adrenomedullin receptor activity-modifying protein, a calcitonin receptor-like receptor and an adrenomedullin receptor.

Sixteenth aspect of the present invention provides the angiogenesis agent according to the fifteenth aspect of the present invention in which the angiogenesis enhancing factor is at least one substance selected from the group consisting of vascular endothelial growth factor, hepatocellular growth factor, fibroblast growth factor-2, angiopoietin, hypoxia inducible factor, and transforming growth factor-β.

Seventeenth aspect of the present invention provides the pharmaceutical composition according to the fifteenth aspect of the present invention in which the adrenomedullin receptor activity-modifying protein is RAMP 1, RAMP 2 or RAMP 3.

Eighteenth aspect of the present invention provides the pharmaceutical composition according to the fifteenth aspect of the present invention in which the ischemic disorder is selected from the group consisting of cerebral infarction, myocardial infarction, angina pectoris, arteriosclerosis obliterans, and Buerger's disease.

Nineteenth aspect of the present invention provides the pharmaceutical composition according to the fifteenth aspect of the present invention in which the edema is cerebral edema.

Twentieth aspect of the present invention provides a method for stabilizing vessel structure in mammals characterized by that at least one substance selected from the group consisting of adrenomedullin, angiogenesis enhancing factor, a substance inhibiting the activity of adrenomedullin degrading enzyme, an adrenomedullin receptor activity-modifying protein, a calcitonin receptor-like receptor and an adrenomedullin receptor is administered to the mammals or expressed in the mammals.

Twenty-first aspect of the present invention provides a method for stabilizing vessel structure in mammals characterized by that at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is administered to the mammals.

Twenty-second aspect of the present invention provides a method for suppressing vascular permeability in mammals characterized by that at least one substance selected from the group consisting of adrenomedullin, angiogenesis enhancing factor, a substance inhibiting the activity of adrenomedullin degrading enzyme, an adrenomedullin receptor activity-modifying protein, a calcitonin receptor-like receptor and an adrenomedullin receptor is administered to the mammals or expressed in the mammals.

Twenty-third aspect of the present invention provides a method for suppressing vascular permeability in mammals characterized by that at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is administered to the mammals or expressed in the mammals.

Twenty-fourth aspect of the present invention provides the method according to the twenty-second or twenty-third aspects of the present invention in which the angiogenesis enhancing factor is at least one substance selected from the group consisting of vascular endothelial growth factor, hepatocellular growth factor, fibroblast growth factor-2, angiopoietin, hypoxia inducible factor, and transforming growth factor-β.

Twenty-fifth aspect of the present invention provides the method according to the twenty-second or twenty-third aspects of the present invention in which according to the eighth aspect of the present invention in which the adrenomedullin receptor activity-modifying protein is RAMP 1, RAMP 2 or RAMP 3.

Twenty-sixth aspect of the present invention provides a method for angiogenesis in mammals characterized by that adrenomedullin is administered to the mammals.

Twenty-seventh aspect of the present invention provides the method according to the twenty-sixth aspect of the present invention in which the angiogenesis arises from the stabilization of the vascular structure by adrenomedullin.

Twenty-eighth aspect of the present invention provides the method according to the twenty-sixth aspect of the present invention in which the angiogenesis arises from the suppression of the vascular permeability by adrenomedullin.

Twenty-ninth aspect of the present invention provides a process for angiogenesis in mammals characterized by that at least one substance selected from the group consisting of adrenomedullin, angiogenesis enhancing factor, a substance inhibiting the activity of adrenomedullin degrading enzyme, an adrenomedullin receptor activity-modifying protein, a calcitonin receptor-like receptor and an adrenomedullin receptor is administered to the mammals or expressed in the mammals.

Thirtieth aspect of the present invention provides a process for angiogenesis in mammals characterized by that at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is administered to the mammals.

Thirty-first aspect of the present invention provides the method according to the twenty-ninth or thirtieth aspects of the present invention in which the angiogenesis enhancing factor is at least one substance selected from the group consisting of vascular endothelial growth factor, hepatocellular growth factor, fibroblast growth factor-2, angiopoietin, hypoxia inducible factor, and transforming growth factor-β.

Thirty-second aspect of the present invention provides the method according to the twenty-ninth or thirties aspects of the present invention in which the adrenomedullin receptor activity-modifying protein is RAMP 1, RAMP 2 or RAMP 3.

Thirty-third aspect of the present invention provides a method for treating or preventing ischemic disorders or edema in mammals characterized by that the angiogenesis agent according to one of the seventh to fourteenth aspects of the present invention or the pharmaceutical composition according to one of the fifteenth to nineteenth aspects of the present invention to the mammals.

Thirty-fourth aspect of the present invention provides a method for treating or preventing ischemic disorders or edema in mammals characterized by that at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is administered to the mammals.

Thirty-fifth aspect of the present invention provides the method according to the thirty-fourth aspect of the present invention in which the angiogenesis enhancing factor is at least one substance selected from the group consisting of vascular endothelial growth factor, hepatocellular growth factor, fibroblast growth factor-2, angiopoietin, hypoxia inducible factor, and transforming growth factor-β.

Thirty-sixth aspect of the present invention provides the method according to the thirty-fourth aspect of the present invention in which the adrenomedullin receptor activity-modifying protein is RAMP 1, RAMP 2 or RAMP 3.

Thirty-seventh aspect of the present invention provides the method according to the thirty-fourth aspect of the present invention in which the ischemic disorder is selected from the group consisting of cerebral infarction, myocardial infarction, angina pectoris, arteriosclerosis obliterans, and Buerger's disease.

Thirty-eighth aspect of the present invention provides the method according to the thirty-fourth aspect of the present invention in which the edema is cerebral edema.

Thirty-ninth aspect of the present invention provides a method for screening a substance having an effect of stabilizing vascular structure, a substance having angiogenesis effect or a substance enhancing the angiogenesis effect, comprising administrating a test article to a nonhuman animal in which at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is knocked out, and then the effect of the test article in the nonhuman animal is analyzed.

Fortieth aspect of the present invention provides a method for screening a substance having an effect of stabilizing vascular structure, a substance having angiogenesis effect or a substance enhancing the angiogenesis effect in vitro, comprising contacting a test article to a cell in which at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is knocked out, and then the effect of the test article in the cell is analyzed.

Forty-first aspect of the present invention provides a method for screening a substance having an effect of stabilizing vascular structure, a substance having angiogenesis effect or a substance enhancing the angiogenesis effect, comprising contacting a test article to a cell containing at least one protein selected from the group consisting of adrenomedullin, angiogenesis enhancing factor, an adrenomedullin receptor activity-modifying protein, a calcitonin receptor-like receptor and an adrenomedullin receptor, and then the effect of the test article in the cell is analyzed.

Forty-second aspect of the present invention provides a method for screening a substance having an effect of stabilizing vascular structure, a substance having angiogenesis effect or a substance enhancing the angiogenesis effect, comprising contacting a test article to a cell in which at least one gene selected from the group consisting of a gene encoding adrenomedullin, a gene encoding angiogenesis enhancing factor, a gene encoding an adrenomedullin receptor activity-modifying protein, a gene encoding a calcitonin receptor-like receptor and a gene encoding an adrenomedullin receptor is expressed, and then the effect of the test article in the cell is analyzed.

Forty-third aspect of the present invention provides the method according to the thirty ninth to forty-first aspects of the present invention in which the angiogenesis enhancing factor is at least one substance selected from the group consisting of vascular endothelial growth factor, hepatocellular growth factor, fibroblast growth factor-2, angiopoietin, hypoxia inducible factor, and transforming growth factor-β.

Forty-fourth aspect of the present invention provides the method according to the thirty-ninth to forty-second aspects of the present invention in which the adrenomedullin receptor activity-modifying protein is RAMP 1, RAMP 2 or RAMP 3.

BRIEF DESCRIPTION OF THE DRAWINGS

FIG. 6 shows the recovery of blood flow and the enhancement of angiogenesis by the administration of AM;

FIG. 7 shows the reduction of the blood flow and the angiogenesis in AM heterozygous knockout mice and AM 22-52 administered mice;

FIG. 11 shows the result of Western Blot analysis showing the expression of VEGF is increased by the administration of AM;

FIG. 20 shows the embryo of RAMP 2 homozygous knockout mice at embryonic day 13.5 embryos;

FIG. 29 shows the result of immunohistochemical staining of AGM (aorta-gonad-mesonephros region) at embryonic day 10.5 embryos cultured on OP 9 cells using PECAM-1;

FIG. 36 shows the measurement of the in vitro angiogenesis using Matrigel assay;

PREFERRED MODE FOR CARRYING OUT THE INVENTION

Figure 1:
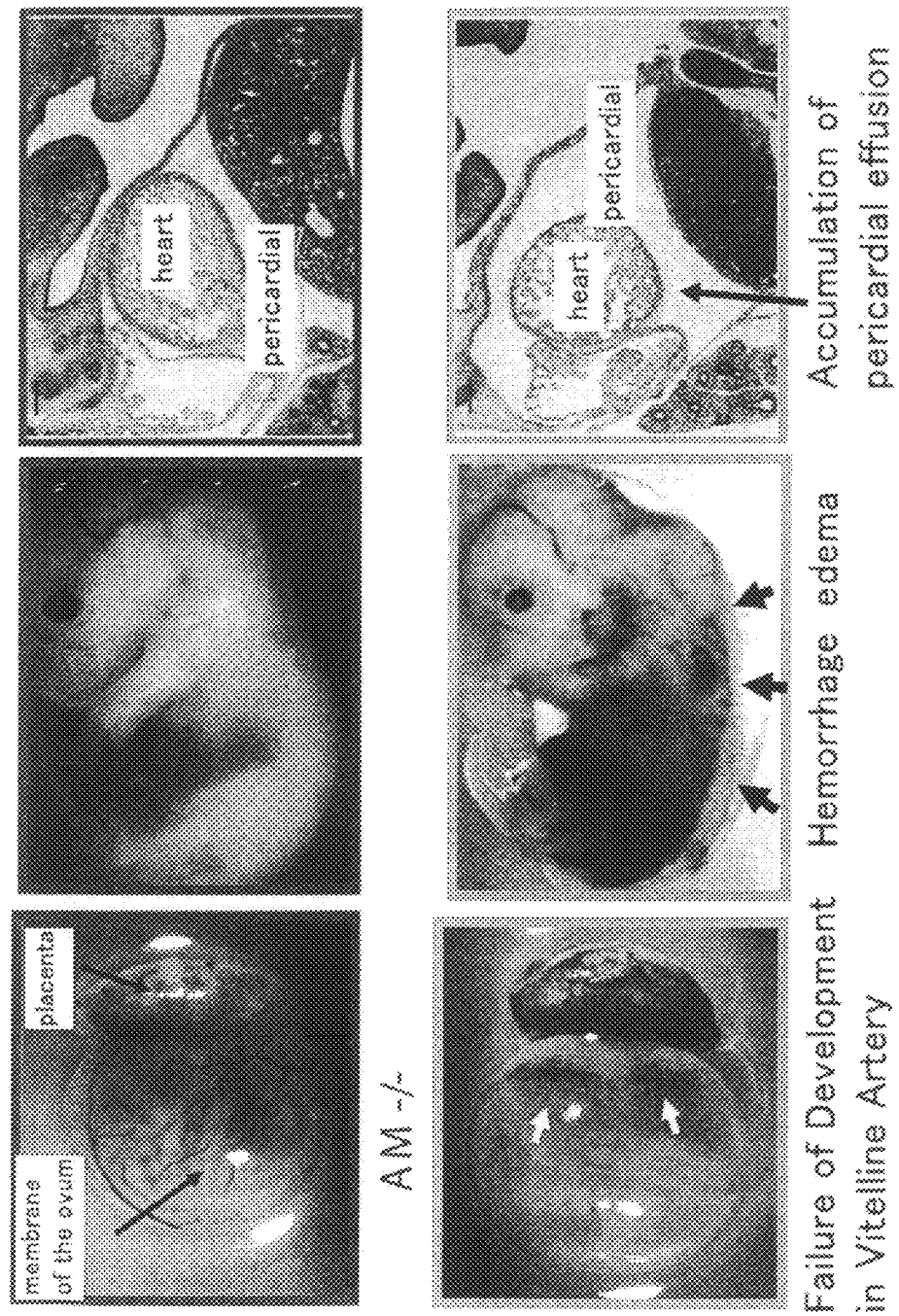
FIG. 1 shows the abnormality in the development of AM homozygous knockout mice.

The present invention will be further described hereafter. The embodiments shown below are provided as examples to explain the present invention. The present invention is not limited to the embodiments. Various variations can be made to the embodiments of the present invention without splitting the spirit of the present invention.

Literatures, patent documents such as publications for patent application and patent publications cited herein are incorporated herein by references.

The present invention relates to an angiogenic agent which contains, as the active ingredient, at least one substance selected from the group consisting of adrenomedullin, a substance inhibiting the activity of adrenomedullin degrading enzyme, an adrenomedullin receptor activity-modifying protein, a calcitonin receptor-like receptor and an adrenomedullin receptor and a method for angiogenesis in mammals using these substances.

The angiogenesis agent of the present invention will be further described below.

1. Adrenomedullin or Associated Proteins Thereof

Adrenomedullin (AM) used as an angiogenesis agent in the present invention is a peptide consisting of 52 amino acids found by Kitamura, Kangawa et al. from human pheochromocytoma tissue in 1993. AM distributes in tissues over the entire body including blood vessel and attracted attention as a venotropic agent with vasodilating effect when it has been found, however, subsequent studies revealed that it has a variety of physiological activities such as regulation of cell migration, regulation of differentiation, anti-inflammatory effect, body fluid volume regulating effect, and cardiac effect.

Adrenomedullin used in the present invention includes the protein comprising the amino acid sequence of SEQ ID No:2 as well as the one in which one or several amino acids are deleted, inserted or added relative to the amino acid sequence SEQ ID NO:2 and have an adrenomedullin (AM) activity (AM variant). In particular, the AM variants comprising:

(i) the amino acid sequences in which one or more (preferably one or several (for example, 1 to 10, more preferably 1 to 5)) amino acids of the amino acid sequence SEQ ID NO:2 are deleted;

(ii) the amino acid sequences in which one or more (preferably one or several (for example, 1 to 10, more preferably 1 to 5)) amino acids of the amino acid sequence SEQ ID NO:2 are substituted with other amino acids;

(iii) the amino acid sequences in which one or more (preferably one or several (for example, 1 to 10, more preferably 1 to 5)) amino acids are added to the amino acid sequence SEQ ID NO:2; and (iv) the amino acid sequence including the combination of (i) to (iii) as mentioned above, and having the effect similar to the AM.

Also, the AM used in the present invention may be a peptide having the homology to the aforementioned amino acid sequences as long as it has an AM activity. Such amino acid sequences include the one having homology of about 85% or more, preferably about 90% or more, more preferably about 95% or more relative to the aforementioned amino acid sequences.

The DNA encoding the amino acid sequences in which one or several amino acids are deleted, inserted or added relative to the amino acid sequence SEQ ID NO:2 can be prepared according to the cite-specific mutagenesis technique such as described in "Molecular Cloning, A Laboratory Manual 2nd ed." (Cold Spring Harbor Laboratory Press (1989)), and Kunkel (1985) Proc. Natl. Acad. Sci. USA 82: 488-92, Kunkel (1988) Method. Enzymol. 85: 2763-6.

Introduction of mutation to DNA can be carried out using the mutagenesis kit based on the cited-specific mutagenesis techniques such as Kunkel method or Gapped duplex method, for example, QuikChange™ Site-Directed Mutagenesis Kit (Stratagene), GeneTailor™ Site-Directed Mutagenesis System (Invitrogen), TaKaRa Site-Directed Mutagenesis System (such as Mutan-K, Mutan-Super Express Km: TaKaRabio).

Herein, the term "AM activity" means the angiogenesis activity through stabilizing the vascular structure and/or suppressing the vascular permeability. The term "stabilizing the vascular structure" means that stable capillary structure of blood structure is maintained for a long period of time through stabilization of vascular endothelial cells, stabilization of basal membrane structure, stabilization of layer structure of vascular smooth muscle, and the like. The term "suppressing the vascular permeability" means that the hemorrhage and edema are suppressed without leaking water or blood cells out of the blood vessels and also includes the suppression through the stabilization of vascular structure.

The stabilization of vascular structure can be confirmed by morphologic observation using electron microscopy, observation of vascular structure in AM knockout mice (to be hereinafter described), expression of adhesion factors and basal membrane construction factors, in vitro angiogenesis assay, and the like. The suppression of vascular permeability can be confirmed by in vitro vascular permeability assay (to be hereinafter described), observation of vascular permeability in knockout mice, expression of water channel gene, and the like.

Aforementioned AM peptides may be obtained directly with peptide synthesis as well as by expression using conventional genetic engineering technique ("Molecular Cloning, A Laboratory Manual 2nd ed." (Cold Spring Harbor Laboratory Press (1989)).

The base sequences of the DNA encoding AM are shown in SEQ ID NO:1 (human) and SEQ ID NO:13 (mouse). The DNA encoding AM include the DNA comprising the base sequence of SEQ ID NO:1 or 13 or mature protein encoding domain thereof (for SEQ ID:NO 1, No. 439-594, for SEQ ID NO:13, No. 2548-2697) as well as the DNA that hybridize with the DNA comprising the base sequence complement to the DNA comprising the base sequence of SEQ ID NO: 1 or 13 or encoding domain thereof under stringent condition and encode the protein having the aforementioned AM activity. The DNA encoding the AM protein having such activity can be obtained from cDNA libraries or genome libraries with hybridization technique known in the art such as colony hybridization, plaque hybridization, and Southern blotting using the probe prepared from the appropriate fragment using the method known to skilled in the art. The stringent condition for the hybridization as described above includes, for example, wash condition of a salt concentration of 100 to 900 mM, preferably 150 to 300 mM, and temperature of 50 to 70° C., preferably 55 to 65° C. For the detailed procedure of the hybridization technique, reference is made by, for example, "Molecular Cloning, A Laboratory Manual 2nd ed." (Cold Spring Harbor Laboratory Press (1989), "Current Protocols in Molecular Biology" (John Wiley & Sons (1987-1997). The DNA to be hybridized includes the DNA comprising the base sequence having homology of about 85% or more, preferably about 90% or more, more preferably about 95% or more relative to the base sequences of SEQ ID NO: 1 or 13 or mature protein encoding domain thereof.

Moreover, in the present invention, a substance inhibiting the activity of adrenomedullin degrading enzyme, an adrenomedullin receptor activity-modifying protein (RAMP), a calcitonin receptor-like receptor (CRLR), an adrenomedullin receptor (AMR) and the like may be used as the stabilizing agent of the vascular structure, suppressing agent of the vascular permeability, or the angiogenesis agent of the present invention. These proteins are herein referred to "AM-associated proteins". The amino acid sequences of AM and AM-associated proteins the gene encoding these proteins are shown below.

The Accession Numbers and SEQ ID NO's of aforementioned genes and proteins are shown in Table 1.

TABLE 1

| Name | Accession Number | Base Sequence | Amino Acid Sequence |
|---|---|---|---|
| Human AM | D14874 | SEQ ID NO 1 | SEQ ID NO 2 |
| Human CRLR | NM_005795 | SEQ ID NO 3 | SEQ ID NO 4 |
| Human AMR | NM_007264 | SEQ ID NO 5 | SEQ ID NO 6 |
| Human RAMP1 | NM_005855 | SEQ ID NO 7 | SEQ ID NO 8 |
| Human RAMP2 | NM_005854 | SEQ ID NO 9 | SEQ ID NO 10 |
| Human RAMP3 | NM_005856 | SEQ ID NO 11 | SEQ ID NO 12 |
| Mouse AM | D78349 | SEQ ID NO 13 | SEQ ID NO 14 |
| Mouse CRLR | NM_018782 | SEQ ID NO 15 | SEQ ID NO 16 |
| Mouse AMR | NM_007412 | SEQ ID NO 17 | SEQ ID NO 18 |
| Mouse RAMP1 | NM_016894 | SEQ ID NO 19 | SEQ ID NO 20 |
| Mouse RAMP2 | NM_019444 | SEQ ID NO 21 | SEQ ID NO 22 |
| Mouse RAMP3 | NM_019511 | SEQ ID NO 23 | SEQ ID NO 24 |

Among AM-associated proteins, the substance inhibiting the activity of AM degrading enzyme includes peptidase inhibitors such as omaptrilat.

The genes encoding aforementioned proteins and its variant and the proteins and its variant can be prepared based on the information of the Accession Numbers, or similar manner to the preparation of AM and its variants described above and used in the present invention.

2. Angiogenesis

Angiogenesis is a physiological phenomenon observed in the growth process of individuals from the early stage of development in various organs and tissues. In the present invention, "angiogenesis" means the formation of new blood vessels in the tissues in which originally no blood vessel exists, such as cure of wound and revascularization to necrotic tissues as well as the revascularization in the tissues in which the blood vessels disappeared for pathologic reason or wound (the blood vessel originally existed).

The mechanism of angiogenesis includes following steps of:

(a) activating the vascular endothelial cells by angiogenesis enhancing factor secreted to the blood vessel in the periphery;

(b) degrading the basal membrane by the enzyme in the vascular endothelial cells;

(c) migration and proliferation of the vascular endothelial cells; and (d) formation of vascular capillary by the vascular endothelial cells.

In the present invention, the mechanism in which AM or AM-associated proteins stabilize the vascular structure to enhance the angiogenesis is shown in addition to the mechanism described above and thus enhancing effect of AM on the angiogenesis is revealed. Hereinafter, as a matter of convenience, among AM and the AM-associated proteins, explanation may be made only on AM as an example.

As described above, confirmation of the stabilization of vascular structure by AM may be carried out by morphologic observation using electro microscopy, observation of vascular structure in AM knockout, expression of adhesion factors and basal membrane factors, in vitro angiogenesis assay, and the like. For example, AM-knockout mice may be prepared to observe the abnormalities arising from the knockout in comparison with the wild-type animal. Knockout animals can be prepared according to the procedure known in the art. Deletion of AM can be carried out using the conventional technique for preparing the knockout mice (Circulation, 104: 1964-71, 2001). For example, a targeting vector in which a part of the AM gene is substituted with the neomycin resistance gene is prepared and then introduced in ES cell to carry out homologous recombination with the original genome sequence artificially to prepare the ES cell in which AM gene is knocked out. Chimera mouse is prepared by microinjection of the ES cell into the mouse blastocyte, from which the knockout mouse is prepared.

Figure 2:
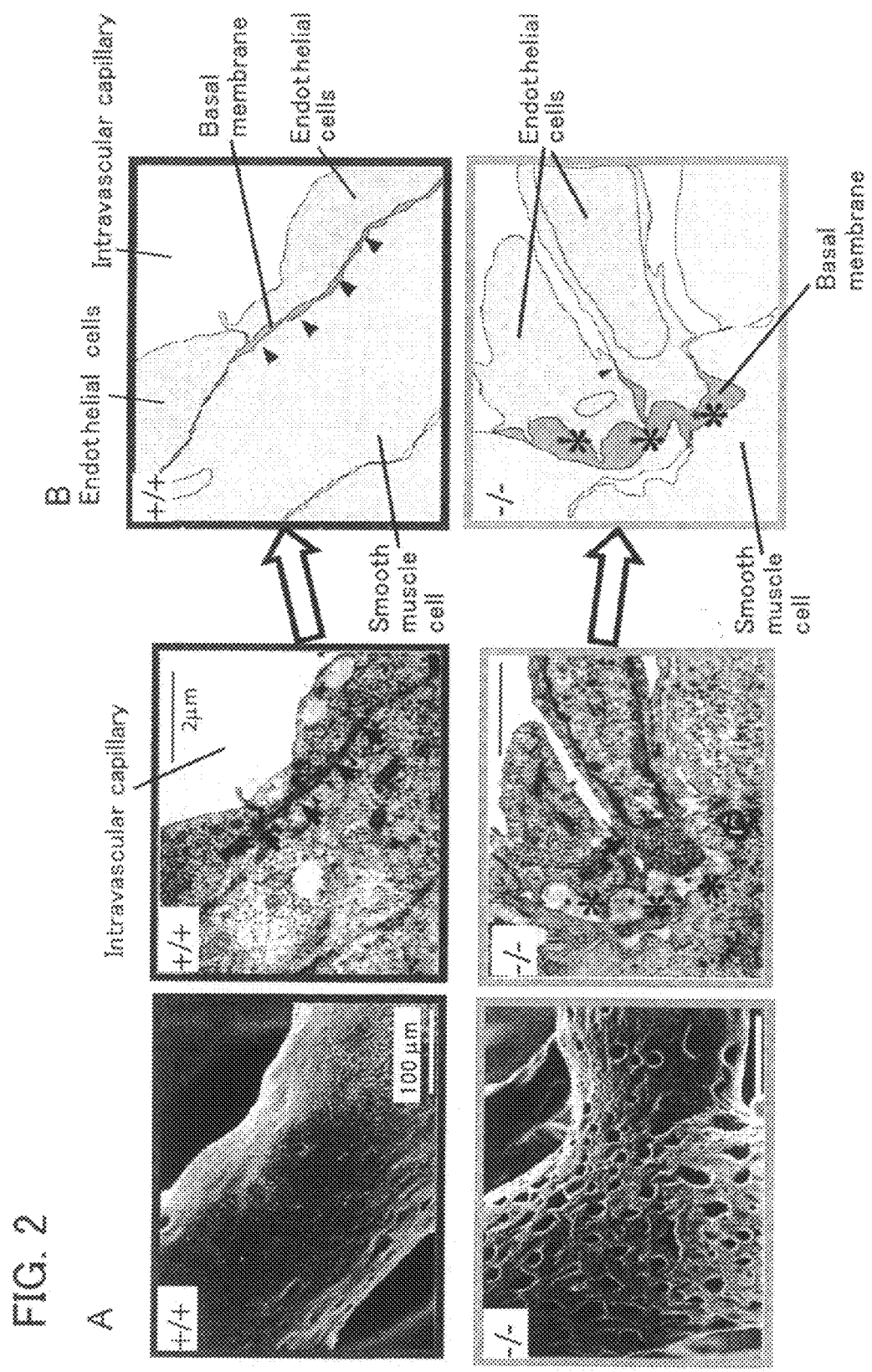
FIG. 2 shows the abnormality in the vascular structure in the development stage of AM homozygous knockout mice.
Figure 3:
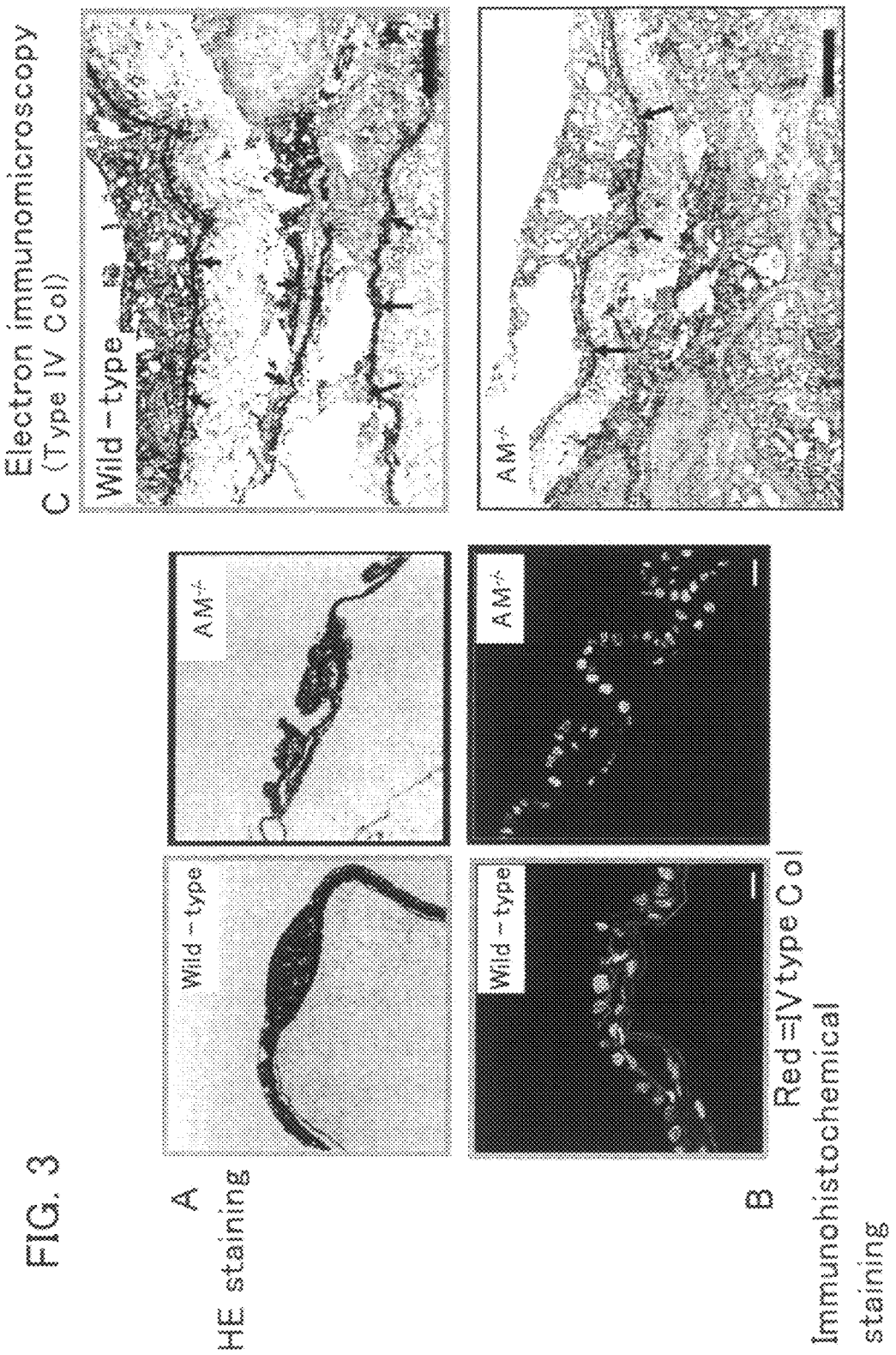
FIG. 3 shows the abnormality in the basal membrane of vitelline artery of AM homozygous knockout mice.

In the AM homozygous knockout mice, failure of development in vitelline artery, hemorrhage and edema in embryos, and accumulation of pericardial effusion are observed (FIG. 1). Abnormality in the vascular structure at the developing stage was observed in the electron microscopic observation of the vascular capillary (FIG. 2). In addition, abnormality was observed in the basal membrane of vitelline artery stained by HE staining, fluorescent immunohistochemical staining, and electron immunomicroscopic observation (FIG. 3). These results shows that AM is indispensable for the generation of the normal blood vessel and the maintenance of its structure.

In the present invention, the mechanism in which angiogenesis is enhanced by the suppression of the vascular permeability is shown in addition to the mechanism described above, and thus AM enhances the angiogenesis. The mechanism of enhancing the angiogenesis by suppressing the vascular permeability is as follows. Intercellular adhesion structure referred to as tight junction is developed among vascular endothelial cells and usually even small molecule are not permeable. However, at the cite of inflammation where the vascular endothelial cells are injured, plasma proteins that is not permeable normally leak out of the blood vessel through the gap formed between the vascular endothelial cells. Thus, it is desired that the vascular permeability is suppressed as much as possible in the injured vascular endothelial cells. The suppression of vascular permeability enhances the angiogenesis.

The suppression of vascular permeability by AM may be confirmed with in vitro vascular permeability assay. In vitro vascular permeability assay is an assay in which the cells are cultured in the insert placed on the culture plate with semipermeable membrane at the bottom to form monolayer, then the substance is added to the insert and the extent of permeability into the plate through the cell monolayer is measured. In particular, the extent of permeability is measured by addition of the substance for the vascular permeability test such as AM, followed by the addition of dextran labeled with FITC onto the cell monolayer, allowing it to permeate through the monolayer, and the fluorescence intensity in the plate well solution is measured. Thus, the suppression activity of AM on the vascular permeability may be investigated.

Figure 8:
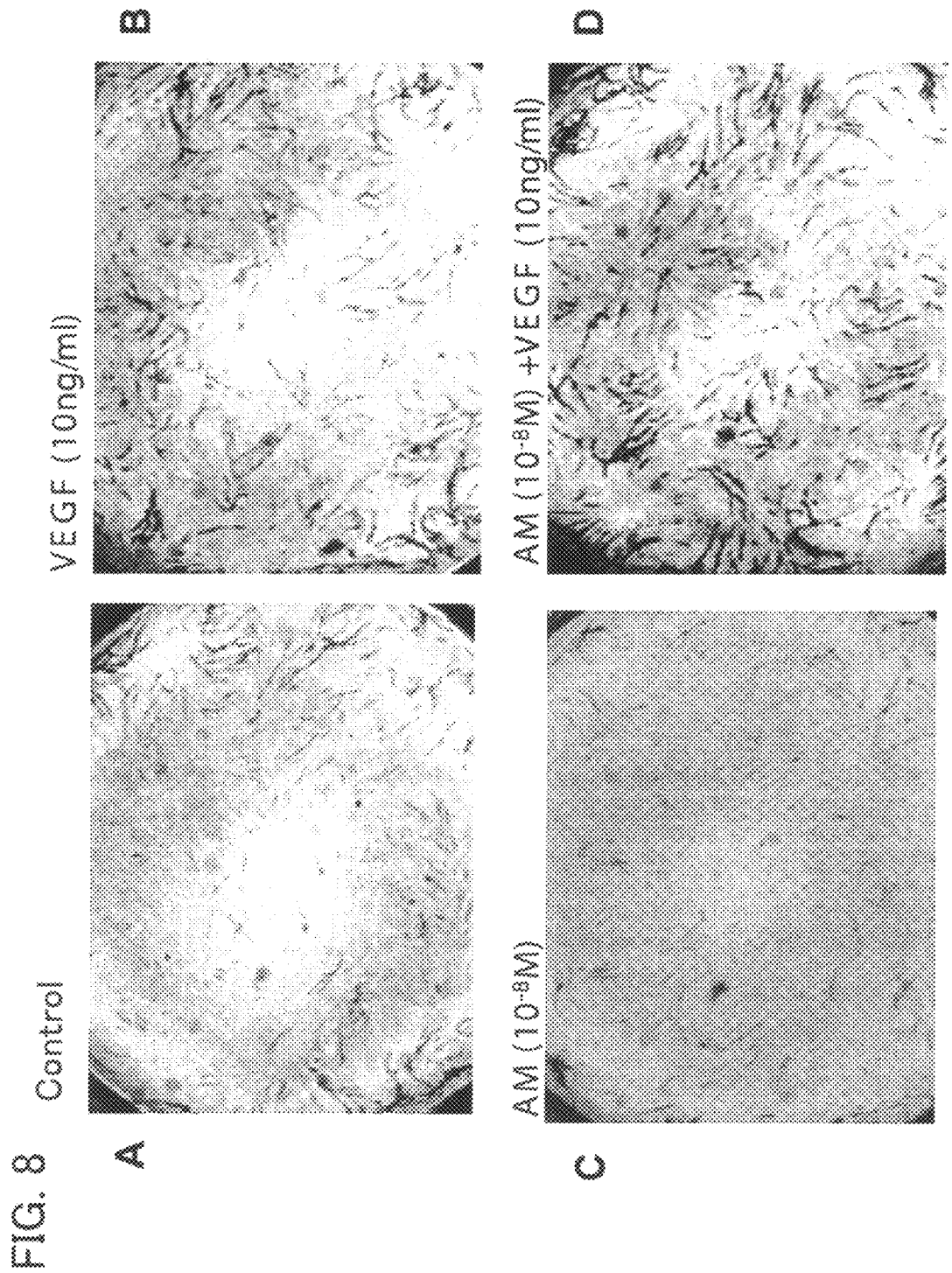
FIG. 8 shows the result of immunohistochemical staining using anti-PECAM-1 antibody showing capillary formation in the co-culture system of vascular endothelial and fibroblast.
Figure 9:
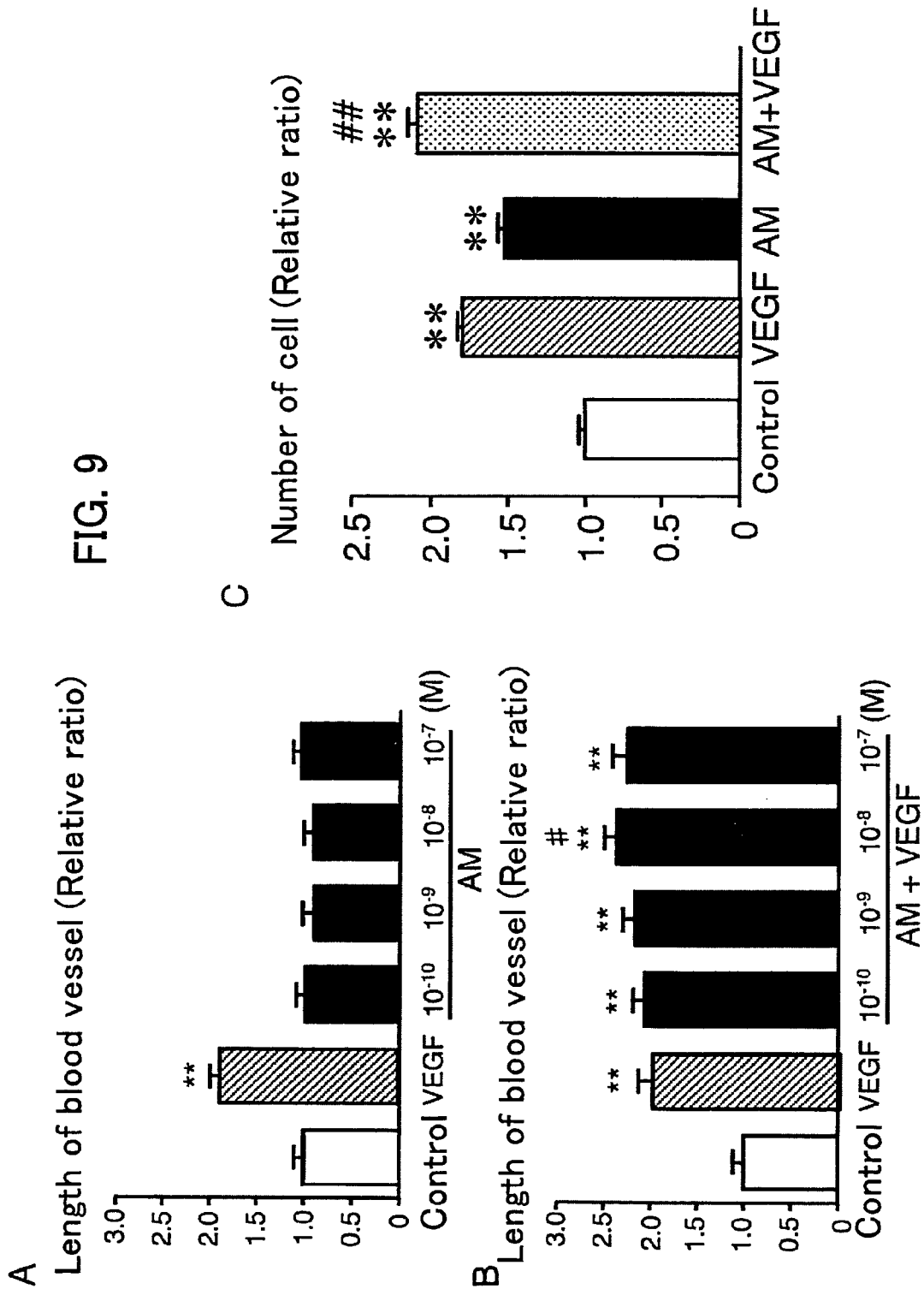
FIG. 9 shows the effect of combination of AM and VEGF on the capillary formation in the co-culture system of vascular endothelial cell and fibroblast.

Angiogenesis enhancing factors include the substance that enhances the angiogenesis through the mechanism consisting of aforementioned four steps. Such angiogenesis enhancing factors include, for example, endothelial cell growth factor (VEGF), hepatic cell growth factor (HGF), fibroblast growth factor-2 (FGF-2), angiopoietin, hypoxia induction factor-1α (HIF-1α), and transforming growth factor-β (TGF-β), one or more of which may used in combination with AM. In vitro model of angiogenesis, i.e. the result of immunohistochemical staining of PECAM-1 (Platelet Endothelial Cell Adhesion Molecule-1) expressed in the capillary face of the vascular endothelial cells showed that, for example, administration of AM and VEGF to the animals in combination enhances the angiogenesis in comparison with the administration of AM and VEGF alone (FIGS. 8 and 9).

Figure 10:
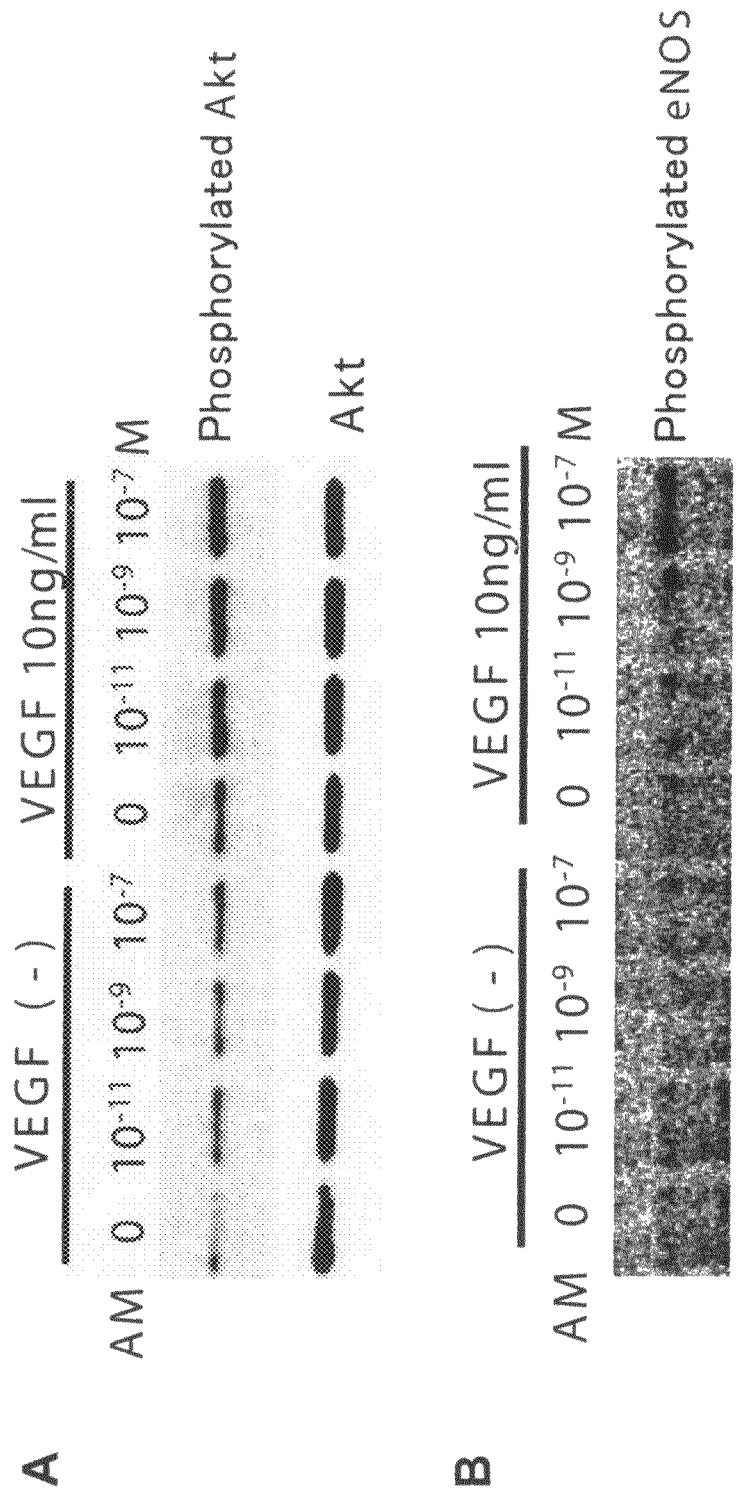
FIG. 10 shows the result that AM enhances the phosphorylation of Akt and eNOS by VEGF.

Also, AM has the effect of inducing other angiogenesis enhancing factors and adhesion factors. Adhesion factor is the substance having the effect of enhancing the adhesion of cells. The example of other angiogenesis enhancing factors induced by AM includes the expression of nitrogen monoxide (NO) via PI3K-Akt-eNOS pathway. Nitrogen monoxide (NO) is well known as an angiogenesis that enhances factor suppressing inflammation and induces vascular formation. The mechanism of the expression of NO via PI3K-Akt-eNOS pathway is as follows: the angiogenesis enhancing factors such as VEGF and HGF (Hepatic cell Growth Factor) induce the conversion of protein kinase Akt to the active form via phosphatidyl inositol 3-kinase (PI3K), then the active form of Akt converts the NO synthetase (eNOS) to the active form by phosphorylation to facilitate the expression of NO. AM contributes to the facilitation of NO synthesis through facilitating the phosphorylation of Akt and eNOS (FIG. 10). Other angiogenesis enhancing factors of which expression is facilitated by AM include, for example, PDGF-A (platelet derived growth factor-A), PDGFR β (PDGF receptor β), Tie-2, TGF-β, β-glycan, eNOS, and the like. Other adhesion factors and basal membrane factors of which expression is facilitated by AM include VCAM-1 (vascular cell adhesion molecule-1), cadherin family, integrin, ostenopontin, claudin 5, catenin α1 or 2, collagen 4, laminin, and the like.

AM receptor and receptor activity-modifying protein (RAMP), a modifier factor of AM receptor also contribute to the stabilization of vascular structure. RAMP is a protein, which has a single transmembrane domain and the existence of RAMP 1 to 3 are known. When the RAMP is co-expressed with calcitonin receptor like receptor (CRLR), RAMP 1 constructs calcitonin gene associated peptide receptor with CRLR. Moreover, the mechanism in which similar molecules RAMP 2 or RAMP 3 associate with same CRLR to construct adrenomedullin receptor, thereby the transport to cellular membrane and the specificity of ligand is determined. The present inventors found that RAMP 2 knockout mice showed the collapse of vascular architecture, leading to marked edema and hemorrhage. On the other hand, it was also found that overexpression of RAMP 2 in vascular endothelial cells stabilized the vascular structure and facilitated the angiogenesis. From these results, it was shown that RAMP is indispensable for the stabilization of vascular structure, suppression of vascular permeability, and angiogenesis.

Therefore, the effect of stabilizing the vascular structure or suppressing the vascular permeability may be used for the angiogenesis as described above in the present invention.

To confirm that the vascular structure is stabilized by AM receptor and RAMP, RAMP gene knockout animals may be prepared by gene targeting of RAMP gene to observe the presence of the abnormality of blood vessels in the knockout animals by electron microscopic observation, immunohistochemical staining, expression of the gene, and the like. Gene targeting may be carried out using a method known to skilled in the art. Abnormalities such as edema and anangioplasia are observed in the membrane of the ovum and embryos obtained from the RAMP knockout animals. In particular, suppression of the development of vitelline artery, embryonic edema, accumulation of pericardial effusion, hemorrhage, and the like. Cause of such hemorrhage and edema includes, but not limited to avulsion of vascular endothelial cells from basal membrane, thinning of vascular smooth muscle layer of aorta, decreased expression of collagen 4 and α actin in vascular wall of aorta. Moreover, comparison of expression levels of cell adhesion factors such as cadherin 3 and claudin 5, and major component of basal membrane such as collagen 4 in the homozygous knockout embryos, umbilical artery, and the like showed that the expression level of these cell adhesion factors and basal membrane factors decreased in RAMP homozygous knockout embryos. Therefore, RAMP may contribute to the regulation of the expression of these factors. Moreover, from the cultivation of aorta-gonad-mesonephros region, vascular rudiment sampled from the homozygous knockout embryos on OP 9 cells, reduction of vascular development is observed. On the other hand, the expression level of RAMP in blood vessel in the RAMP heterozygous knockout mice decreases by half, angiogenesis level observed by Matrigel plug assay also decreases. These results shows that RAMP is indispensable for normal vascular development and stabilization of vascular construction. In addition, AM-RAMP signal system contributes to the stabilization of vascular structure through the stabilization of cellular adhesion and the vascular basal membrane structure. Therefore, it is shown that AM receptor and RAMP; AM receptor modifier factor are also indispensable for the vascular formation (angiogenesis).

Here, it is considered that a substance modulating the AM signal via RAMP (AM-like substance) may also contribute to the stabilization of vascular structure through the stabilization of cellular adhesion and the vascular basal membrane structure. Therefore, such AM-like substance may also contribute the vascular formation (angiogenesis). These AM-like substance is, for example the substance that can induce the intracellular signal transduction in the cell expressing RAMP.

3. Establishment of Cell Line with Overexpressed RAMP 2

In the present invention, focus on RAMP 2, a cell line with overexpressed RAMP 2 gene was established using EAhy 926, a cell line derived from the human umbilical vein endothelial cell. In particular, the cell line was obtained by inserting and attaching the human RAMP 2 cDNA consisting of about 580 bp into the expression vector known in the art, then introducing the expression vector into the host. The expression vector and the host are not particularly limited as long as they are capable of expressing the target gene and HUVEC cell may be used as well as EAhy 926 cell as the host.

Therefore, the cell with overexpressed RAMP 2 gene in about 1000 times in comparison with control cells may be prepared.

The property of the cell with overexpressed RAMP 2 is as follows.

The proliferation potency of the cell line with overexpressed RAMP 2 is lower than that of control cells, however it shows the resistance against the apoptotic stimulation compared with control cells and capillary formation ability of cell with overexpressed RAMP 2 on Matrigel significantly increases.

In addition, the cell with overexpressed RAMP 2 cultured on Matrigel shows the increased expression of claudin 5 that is an importance factor for forming tight junction of endothelial cells. It may be confirmed by real-time PCR technique.

RAMP 2 forced expression system may be used for the screening of the substance with AM-like activity and facilitates the angiogenesis by using the intracellular cAMP elevating activity as a marker.

4. Stabilizing Agent of Vascular Structure, Suppressing Agent of Vascular Permeability, Angiogenesis Agent and Pharmaceutical Composition The stabilizing agent of vascular structure, suppressing agent of vascular permeability, and angiogenesis agent of the present invention are for treating or preventing ischemic disorders and edema and comprise AM as an active ingredient. Aforementioned AM associated proteins, i.e. other angiogenesis enhancing factors known in the art, a substance inhibiting the activity of AM degrading enzyme, RAMP, CRLR, AMR (AM receptor) (also referred to as "angiogenesis enhancing factors" herein) also contribute to the angiogenesis. Therefore, the stabilizing agent of vascular structure, suppressing agent of vascular permeability, and angiogenesis agent of the present invention comprise angiogenesis enhancing factor, a substance inhibiting the activity of AM degrading enzyme, RAMP, CRLR, AMR or combination thereof (AM-associated proteins) as active ingredients.

Thus, to enhance the angiogenesis, these AM or AM-associated proteins may be used alone or in combination accordingly. The present invention provides an agent for treating or preventing ischemic disorders and edema comprising at least one substance selected from the group consisting of AM, angiogenesis enhancing factor, a substance inhibiting the activity of AM degrading enzyme, RAMP, CRLR, AMR.

The present invention also provides a pharmaceutical composition for combination administration of AM and any one substance selected from the group consisting of angiogenesis enhancing factor, a substance inhibiting the activity of AM degrading enzyme, RAMP, CRLR, AMR or combination thereof (AM-associated proteins). The term "combination administration" means the administration method in which AM and angiogenesis enhancing factor and the like are administered simultaneously and one after another (regardless of the order of administration). Any administration methods are encompassed in the "combination administration" of the present invention as long as AM and AM-associated proteins are administered within the same administration schedule.

A particular example of the substance inhibiting the activity of AM degrading enzyme includes, but not limited to a protease inhibitor such as omaptrilat.

Ischemic disorders means the disorder arising from decreased blood flow in organs as a result of circulatory system disorder and a representative example is arteriosclerotic disease. Example of ischemic disorders such as arteriosclerotic disease includes, for example, cerebral infarction, myocardial infarction, angina pectoris, arteriosclerotic obliteration, Burger's disease (spontaneous gangrene (also referred to as thromboangiitis obliterans)) and other arteriosclerotic diseases. Myocardial infarction, angina pectoris, cerebral infarction, arteriosclerotic obliteration, and Burger's disease are arteriosclerotic diseases as well as ischemic disorders. However, as a matter of convenience, they are explained as part of ischemic disorders herein.

Edema means abnormal accumulation of water in intercellular space and may occur systemically or topically. Systemic factor for edema includes excretory disorder of water and sodium in kidney and topical factor includes such as interchange of water through capillary wall, lymph flow, and water conservation ability of tissue. Edema occurs as a result of complicate interaction of these factors. Edema includes cerebral edema, cardiac edema, hepatic edema, nutritional (hypoproteinemic) edema, vascular edema, angioneurotic edema, inflammatory edema, allergic edema, retinal edema, and crural edema, preferably cerebral edema.

Site of application of the stabilizing agent of vascular structure, suppressing agent of vascular permeability, angiogenesis agent or pharmaceutical composition of the present invention is not particularly limited but may be applied to blood vessel, joint, skin, eyes, nose, tumor and the like. Moreover, the type the ischemic disorders and edema are not particularly limited to one type in the present invention, but complication of a plurality of disorders or edemas is also encompassed in the application of the present invention.

The stabilizing agent of vascular structure, suppressing agent of vascular permeability, angiogenesis agent or pharmaceutical composition of the present invention may be administered to mammals in need of angiogenesis. The mammal to be administered includes, but not limited to, for example, livestock such as cattle, horse, sheep, and goat; pet such as dog and cat; experimental animal such as mouse, rat, guinea pig, and rabbit.

The stabilizing agent of vascular structure, suppressing agent of vascular permeability, angiogenesis agent or pharmaceutical composition of the present invention may be administered either orally or parenterally. For oral administration, for example, tablets, capsules, granules, powders, or syrups may be used. For parenteral administration, injections, suppositories or ophthalmic solutions and the like, pulmonary formulation (for example, the one using nebulizer), nasal formulation, transdermal formulation (such as ointments and creams), and the like. The formulation for injection may be administered systemically or topically via intravenous injection such as infusion, intramuscular injection, interperitoneal injection, subcutaneous injection and the like. These formulations may be produced by the method well known in the art using pharmaceutically acceptable additives such as excipients, lubricants, binders, disintegrants, stabilizing agents, correctives, diluents and the like.

Excipients include, for example, starch such as potato starch, corn starch, lactose, crystalline cellulose, calcium hydrogen phosphate, and the like.

Lubricants (coatings) include, for example, ethyl cellulose, hydroxypropyl cellulose, hydroxypropylmethyl cellulose, shellac, talc, carnauba wax, paraffin, and the like.

Binders include, for example, polyvinyl pyrrolidone, macrogol, and the compounds similar to the aforementioned excipients.

Disintegrators include, for example, the compounds similar to the aforementioned excipients, chemically modified starch, cellulose such as croscarmellose Sodium, carboxymethylstarch sodium, cross-linked polyvinylpyrrolidone.

Stabilizing agents include para-oxy benzoic acid esters such as methylparaben, propylparaben; alcohols such as chlorobutanol, benzyl alcohol, phenylethyl alcohol; benzalkonium chloride; phenols such as phenol, cresol. Moreover, they include thimerosal, dehydroacetic acid, and sorbic acid.

Correctives include sweetners, acidulants, and flavors usually used.

Solvent for the production of solutions include ethanol, phenol, chlorocresol, purified water, distilled water, and the like.

Surfactants or emulsifiers include, for example polysorbate 80, polyoxylstearate 40, lauromacrogol, and the like.

The additives as described above may be used alone or in combination depending on the formulation of the angiogenesis agent of the present invention. For example, for the injections, purified AM dissolved in solvent (for example, saline, buffer solution, glucose solution, and the like) with additives such as Tween 80, Tween 20, gelatin, human serum albumin, and the like. Alternatively, such formulation may be in the form of freeze-dried powder for dissolving prior to use. For example, sugar alcohols or sugars such as mannitol and glucose may be used as excipients for freeze-drying.

Dosage of the stabilizing agent of vascular structure, the suppressing agent of vascular permeability, the angiogenesis agent, or the pharmaceutical composition of the present invention varies depending on the age, sex, symptom, route of administration, number of doses, and dosage form. Administration method may be chosen depending on the age and symptom of the patient. Effective dose is, for example, may be 50 ng/hour for continuous use and may be 1.0 to 5.0 µg/kg/hour per each dose. However, the dosage of the stabilizing agent of vascular structure, the suppressing agent of vascular permeability, and the angiogenesis agent is not limited to these dosages.

As described above, angiogenesis enhancing factor known in the art may be used in combination with the dosage of the stabilizing agent of vascular structure, the suppressing agent of vascular permeability, and the angiogenesis agent of the present invention. The angiogenesis enhancing factor that may be used in the present invention includes, but not limited to vascular endothelial growth factor (VEGF), hepatic cell growth factor (HGF), fibroblast growth factor-2 (FGF-2), angiopoietin, hypoxia-inducible factor-1α (HIF-1α) and TGF-β.

In the pharmaceutical composition for the combination therapy, the dosage of AM and the AM-associated protein varies depending on the age, sex, symptom, route of administration, number of doses, and dosage form. Administration method may be chosen depending on the age and symptom of the patient. Effective dose is, for example, may be 50 ng/hour for continuous use and may be 1.0 to 5.0 µg/kg/hour per each dose.

Effect of the stabilizing agent of vascular structure, the suppressing agent of vascular permeability, the angiogenesis agent, or the pharmaceutical composition of the present invention may be tested and investigated as follow. For example, angiogenesis potency may be evaluated using lower-extremity ischemia model mouse (see Examples).

Rescue test using AM knockout mouse may also be carried out. In the lower-extremity ischemia model prepared from the AM knockout mouse with decreased expression level of AM, angiogenesis potency decreases. When AM is administered exogenously to the AM knockout mouse, recovery of angiogenesis potency may be observed. This is referred to as "rescue test".

Moreover, in the present invention, AM and the AM-associated protein (angiogenesis enhancing factor, a substance inhibiting the activity of adrenomedullin degrading enzyme, adrenomedullin receptor activity-modifying protein, calcitonin receptor-like receptor, and adrenomedullin receptor) may be administered to mammals (human or no-human mammals) in need of angiogenesis to induce angiogenesis, or aforementioned AM and AM-associated proteins may be expressed (for example, through gene expression) in mammals in need of angiogenesis to induce the angiogenesis in the mammals. The term "expression" means production of AM or AM-associated proteins in mammals. To carry out gene therapy, AM gene, a gene encoding angiogenesis enhancing factor, a gene encoding an adrenomedullin receptor activity-modifying protein, a gene encoding a calcitonin receptor-like receptor and a gene encoding an adrenomedullin receptor may be administered to mammals alone or in combination.

For the gene therapy, each gene may be directly administered via injection or the vector in which nucleic acid is incorporated may be administered. Such vector includes adenovirus vector, adeno-associated viral vector, herpesvirus vector, vaccinia virus vector, retroviral vector, lentivirus vector, and the like. Administration may be carried out efficiently using these virus vectors.

The aforementioned genes incorporated into phospholipids-based vesicle such as liposome may also be administered. For example, vesicles in which the gene is incorporated is injected into the desired cell using lipofection technique. The resulting cells may be administered systemically via intravenously, intra-arterially and the like. The cells may be administered topically such as intracerebrally.

Dosage of the stabilizing agent of vascular structure, the suppressing agent of vascular permeability, the angiogenesis agent, or the pharmaceutical composition of the present invention varies depending on the age, sex, symptom, route of administration, number of doses, and dosage form. For gene therapy, dosage of adenovirus vector, for example, may be in the range of about $10^6$ to $10^{11}$ per single daily dose.

Commercially available transfection kit (for example, AdenoExpress™: Clontech) may be used for the delivery of AM gene and RAMP gene for the gene therapy to the desired organs or tissues.

Moreover, treatment or prevention of ischemic disorders or edemas by the stabilizing agent of vascular structure, suppressing agent of vascular permeability, angiogenesis agent or method for angiogenesis may be confirmed by topical injection of hyperosmotic substance to lower-extremity edema model animal (see Examples).

5. Screening Method

The present invention provides a method for screening a substance having an effect of stabilizing vascular structure, a substance having angiogenesis effect or a substance enhancing the angiogenesis effect using cells or animals with decreased expression level of AM or AM-associated proteins (knockout cells or animals). For example, desired substance may be obtained by administering test article to the animal with decreased level of expression of AM gene or AM-associated gene (knockout animal) then analyzing the effect of the test article in the animal (for example, the presence of angiogenesis).

The present invention also provides a method for screening (for example, screening in vitro) a substance having an effect of stabilizing vascular structure, a substance having angiogenesis effect or a substance enhancing the angiogenesis effect using the cell having AM or AM-associated protein or cell with overexpressed AM or AM-associated protein comprising contacting a test article to these cells, then analyzing the effect of the test article in the cells.

The term "effect of test article" means the effect arising from the test article bound to the protein expressed, leading to a certain effect in the cell, which means both of the effect that enhance or suppress the activity of AM or AM-associated proteins. The term "analyzing" means measuring the angiogenesis effect or effect of enhancing the angiogenesis through such interaction. The mechanism of the interaction includes the interaction with receptor, intracellular signal transduction, and the like. In general, the screening of agonists or antagonists for treating or preventing the diseases in need of the angiogenesis is carried out.

In particular, the screening method comprises contacting the test article with the cells with overexpressed AM or AM-associated proteins, then measuring the signal transduction within the cells, and selecting a substance showing similar signal transduction to AM. The intracellular signal transduction may be determined by detection assay kit available from commercial sources. For example, elevation activity of second messenger such as intracellular cAMP, cGMP, calcium ion, inositol 3-phosphate; second messenger synthetic enzyme such as adenyl cyclase, phospholipase; protein kinase such as tyrosine/threonine kinase; protein dephosphorylase; low molecular GTP-binding protein (for example, G protein, ras protein, and the like); caspase and the like may be used as a marker.

The target of the screening method of the present invention is a substance having an effect of stabilizing vascular structure, a substance having angiogenesis effect or a substance enhancing the angiogenesis effect, in particular, AM-like substances the bind with AM receptor mediated by RAMP.

The term "substance having stabilizing effect of vascular structure" means the substance having the effect as defined in the term "stabilize vascular structure", the substance having the effect of stabilizing vascular structure for a long period of time through stabilizing the adhesion between endothelial cells, stabilization of basal membrane structure, stabilization of layer structure of vascular smooth muscles, and the like.

The term "substance having the effect of suppressing vascular permeability" means the substance having the effect as defined in the term "suppressing vascular permeability", the substance having the effect of suppressing ischemic disorders and edemas without leaking water and plasma cells out of the blood vessels The term "substance having the effect of enhancing angiogenesis" means the substance having angiogenesis activity itself including the substance having the effect similar to that of growth factors such as VEGF.

The term "substance having the effect of enhancing the angiogenesis activity" means the both of the substances that increases the expression level and the activity of the substance having angiogenesis activity and the substance that induces the angiogenic activity by decreasing the expression level and activity of the substance that suppresses the angiogenesis Test article subjected to the screening includes, for example, peptides, polypeptides, synthetic compounds, microorganisms, metabolites of microorganisms, extracts from tissues or cells of animals and plants, or the libraries thereof. Library includes a library of synthetic compounds (for example, combinatorial library), peptide library (for example, combinatorial library), and the like. The substance subjected to the screening may be either naturally occurring or synthetic. Single candidate chemical substance may be tested independently, as well as the combination of several candidate chemical substances (including libraries) may be tested. The substance having desired activity may be isolated by fractionating repeatedly from the cellular extract.

The stabilization activity of vascular structure of the target substance can be confirmed by any of the method described above, including, but not limited to morphologic observation using electron microscopy, observation of vascular structure in AM knockout mice, expression of adhesion factors and basal membrane construction factors, in vitro angiogenesis assay, and the like. The determination and confirmation may also be made by the rescue test described above.

The suppression activity of vascular permeability may be confirmed by in vitro vascular permeability assay (to be hereinafter described), observation of vascular permeability in knockout mice, expression of water channel gene, and the like, without limiting to the certain methods. The determination and confirmation may also be made by the rescue test described above.

Angiogenesis activity or enhancing activity of the target substance may be determined or confirmed by, for example, the rescue test as described above (however, the method is not limited to the rescue test). In the AM or AM-associated proteins homozygous knockout mice, failure of development in vitelline artery, hemorrhage and edema in embryos, and accumulation of pericardial effusion are observed, and the vascular formation and the maintenance of vascular structure may be used as marker. The vascular formation and the maintenance of the vascular structure may be determined using HE staining, immunohistochemical staining, electron microscopic observation, and the like.

When the in vitro screening is carried out using cells, candidate substance is administered to the cell with overexpressed AM receptor or RAMP. The substance increasing the formation of capillary structure in the in vitro culture on Matrigel, or activating the intracellular cAMP or PI3k-Akt-eNOS system may be considered to be a substance enhancing the angiogenesis via AM receptor or RAMP.

EXAMPLES

Now the present invention will be further illustrated in reference to the following Examples. However, the present invention is not intended to be limited to these Examples.

Example 1

Generation of AM-Knockout Mice

A targeting vector was constructed to replace exons 1 to 3 and part of exon 4 of mouse AM gene with the neomycin resistance gene.

λ-Pharge clone comprising AM genome sequence was screened from the λ-pharge library from 129 mice using cDNA of AM gene as a probe. From the clone, a about 7.8 kb fragment of AM gene from exon 1 to 5' side and a about 1 kb fragment from in the middle of exon 4 to 3' side were removed by restriction enzyme. These two fragments were subcloned to pBluescript so that they sandwich neomycin resistance gene (PGK-neor) in between to prepare targeting vector. The targeting vector was designed so that the genome DNA of about 2.4 kb containing exons 1 to 3 and part of exon 4 of AM gene is destroyed by homologous recombination of the targeting vector and genome DNA.

The resulting vector was transfected into the mouse ES cells by means of electroporation. The ES cells in which homologous recombination of transfected gene with the genome sequence was carried out were screened, and then the resulting ES cells were introduced in mouse blastocyst to prepare chimera mouse. The chimera mice were mated with wild-type mice and the mice with introduced gene were selected to obtain AM heterozygous knockout mice. The heterozygous mice were mated with each other to obtain homozygous mice.

In the homozygous knockout mice at embryonic day 13.5 embryos, failure of development in vitelline artery, hemorrhage and edema in embryos, and accumulation of pericardial effusion were observed, which shows that AM is indispensable for the normal vascular formation and maintaining the vascular structure (FIG. 1).

In FIG. 1, panel A shows, panel B shows embryos, and panel C shows heart of embryos and cardiac sac, respectively. The result of wild-type mice is shown in upper panel and the result of AM homozygous knockout mice is shown in lower panel.

The vascular capillary of AM homozygous knockout mouse at embryonic day 12.5 embryos was observed using electron microscope. Abnormality in the vascular structure in the development stage was observed (FIG. 2). In FIG. 2, left hand side of panel A shows the scanning electron micrograph, the right hand side of panel A shows the transmission electron micrograph, and panel B shows the illustration of the transmission electron micrograph. In normal mice ("+/+" in panel A and B), vascular formation occurred normally, however, in homozygous knockout mice ("−/−" in panel A and B), many gaps were observed in blood vessels.

Moreover, the HE staining, immunofluorescent staining, and electron immunomicroscopic observation of basal membrane of vitelline artery in AM homozygous knockout mice showed the abnormality in the expression of collagen 4 that forms the basal membrane of vitelline artery (FIG. 3). In FIG. 3, panel A shows the HE stained image, panel B shows the immunofluorescent stained image, and panel C shows the electron immunomicrograph, respectively.

As AM homozygous knockout mouse is embryonic lethal, AM heterozygous knockout mouse was used in the following experiments.

Example 2

Evaluation of the Potency of Angiogenesis Using the Lower Extremity Ischemia Model Mouse Mouse lower extremity ischemia model was prepared as follows.

C3H mice were anesthetized with nembutal and then skin of one side of lower extremity was cut open to expose artery of lower extremity. The lower extremity ischemia model was prepared by ligating artery of lower extremity at upper groin and lower popliteal region and resecting the artery of lower extremity at this region. The recovery of the blood flow after the resection of the artery of lower extremity by the development of the collateral circulation was observed.

C3H mice at the age of 6 months were divided into three groups; AM administration group, VEGF administration group, and control group. Mice of AM treatment group was continuously injected with AM (50 ng/h) by osmotic pump. Each mouse of VEGF administration group was injected with 20 µl of VEGF (5 ng/h) intramuscularly and used as positive control. Mice of control group were injected with PBS continuously.

Figure 4:
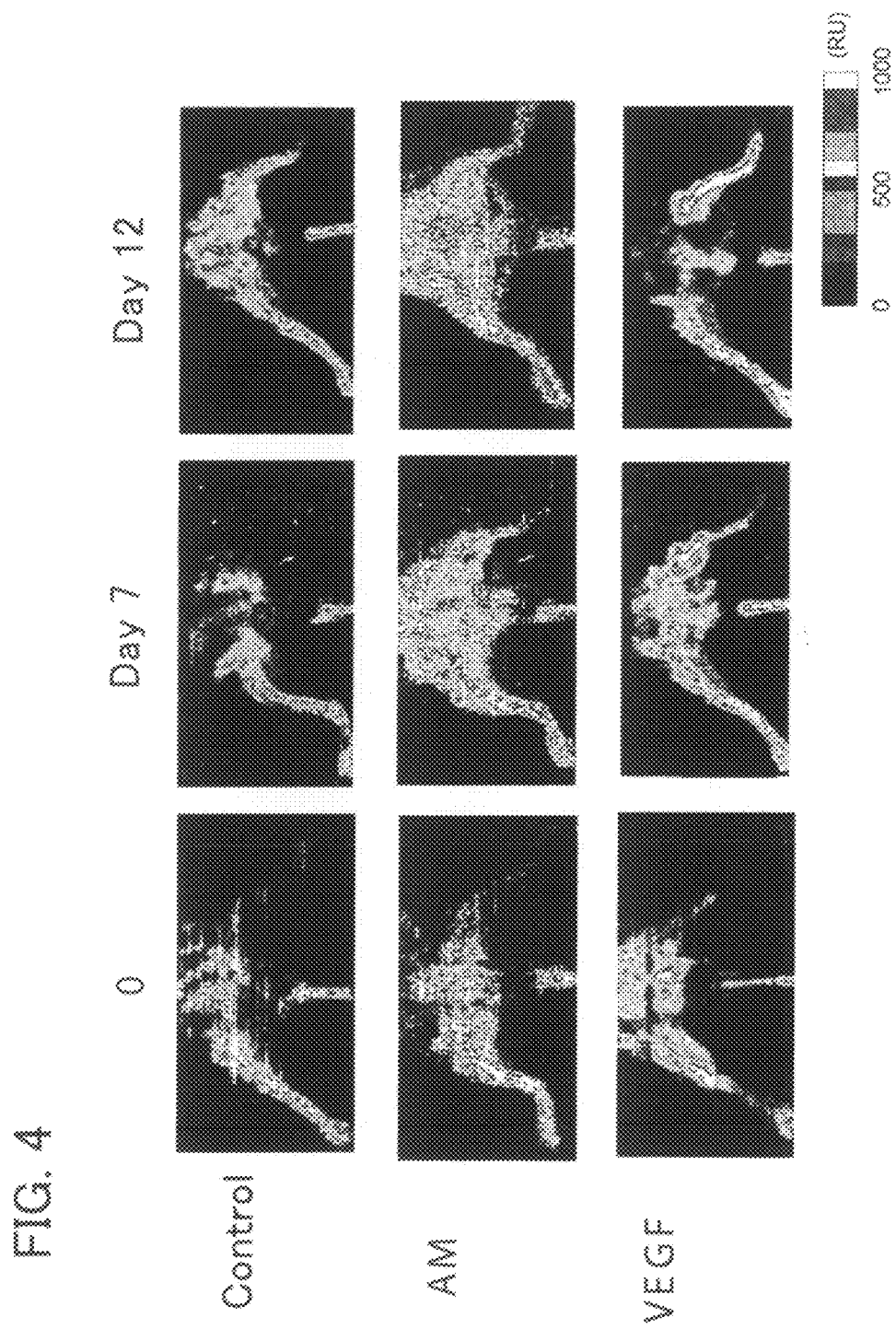
FIG. 4 shows the laser Doppler perfusion imaging showing that the blood flow is recovered in lower extremities of AM administered mice group.
Figure 5:
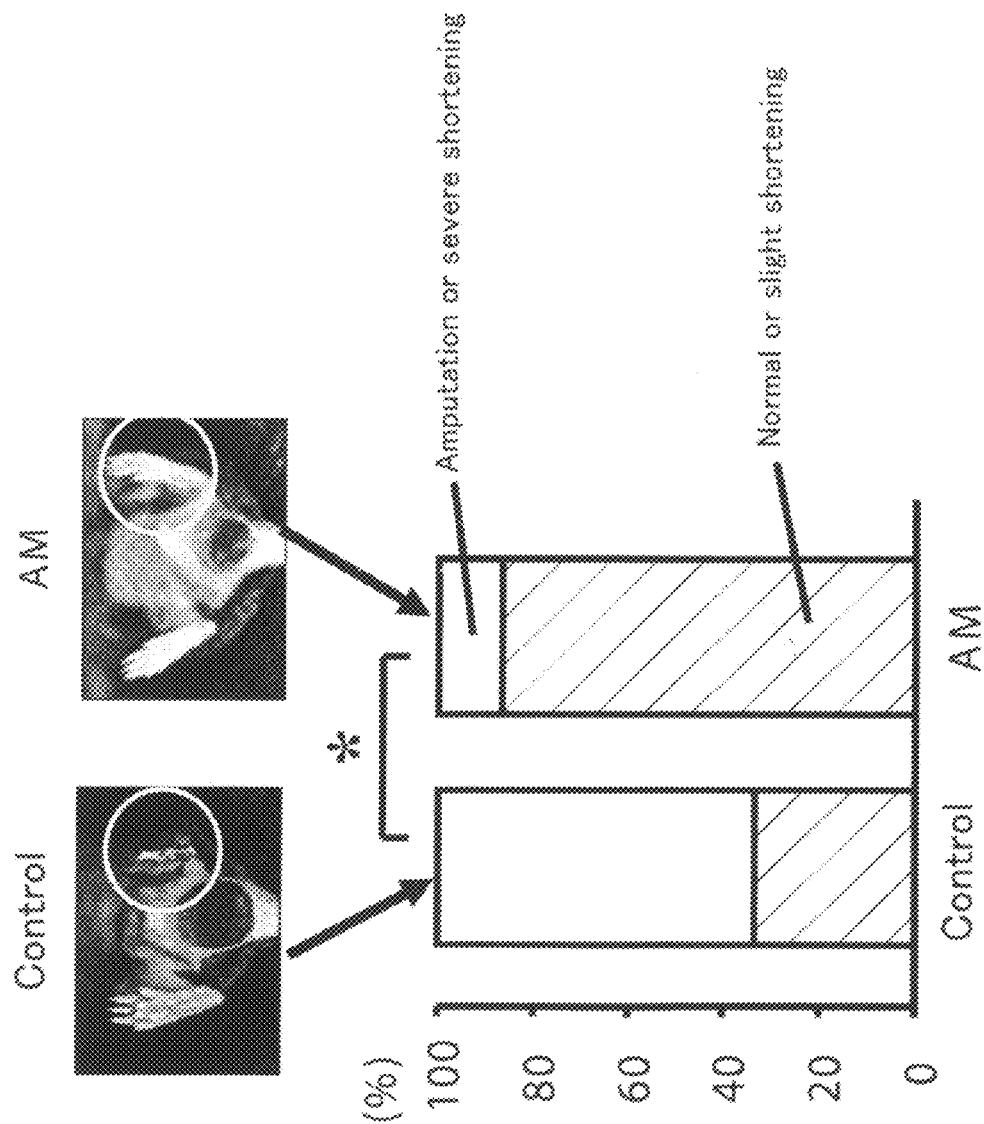
FIG. 5 shows the recovery of the wound in lower extremities of AM administered mice group.

The blood flow in the lower extremity ischemia model was monitored using laser Doppler perfusion imaging. The effect of AM on wound healing was also investigated. Improvement in the recovery of the blood flow of lower extremity was observed in the AM administration group (FIG. 4, AM). In FIG. 4, almost no blood flow in ischemic lower limb was observed on the first day of ischemic model preparation (embryonic day 0). Day 7 and 12, the recovery of blood flow was observed in AM administration group. Reduction of wound and decreasing in the number of amputation and shortening of lower limb were observed in mice of AM administration group (FIG. 5). FIG. 5 shows that in AM administration group the percentage of the mice in which the lower limb is normal or with slight wound is more than 80% and the number of mice in which the lower limb was amputated or with severe wound was smaller than that in the control group.

In FIG. 5, the mark "*" denotes $p<0.05$. Hereinafter the same.

Quantification of the recovery of the blood flow using the ratio between the blood flow of lower limb at ischemic side (left: L) and the blood flow of lower limb at non-ischemic side (right: R) (L/R) confirms the significant recovery in the blood flow by the administration of AM (FIG. 6, panel A). The increasing of the number of new intramuscular blood vessel at the side of operation was also observed (FIG. 6, panel B). In contrast, in AM heterozygous knockout mice (AM +/−), and the mice administered with "AM 22-52", a truncated form of AM consisting of from 22 to 52 amino acid sequence (AM antagonist), suppression of the recovery of blood flow and the angiogenesis were observed (FIG. 7). In FIG. 7, the mark "**" denotes p<0.01. Hereinafter the same.

Example 3

Evaluation of the Potency of Angiogenesis Upon Administration of AM and VEGF Using In Vitro Model in the Co-Culture System of Endothelial Cells and Fibroblast The co-cultivation of fibroblast cells from human skin and human umbilical vein endothelial cell (HUVEC) was carried out for 11 days and the cultured cells were subjected to the immunohistochemical staining using anti-PECAM-1 (Platelet Endothelial Cell Adhesion Molecule-1). Therefore, the formation of capillary structure may be visualized. Using this system, angiogenesis activity may be evaluated in vitro. AM and VEGF were administered to the system to evaluate their angiogenesis activity.

Results are shown in FIGS. 8 and 9. In FIG. 8, panel A shows control, panel B shows the result of the administration of VEGF, panel C shows the result of the administration of AM, and panel D shows the result of administration of AM and VEGF in combination, respectively. In FIG. 9, panel. A shows the length of the blood vessel (relative value) when AM was used alone, panel B shows the length of blood vessel (relative value) when AM and VEGF were used in combination, and panel C shows the cell numbers (relative values), respectively. In the endothelial cells and fibroblast cells cultured with AM and VEGF administered in combination, larger number of capillary structure was visualized with the staining with PECAM-1 in comparison with the cultivation system in which AM or VEGF was administered alone (FIG. 8, panel D). These result shows that the combination of AM and VEGF enhanced angiogenesis.

Concentration-dependent enhancement of the formation of capillary structure was observed (FIG. 9, panel B). Proliferation of vascular endothelial cells was determined in the cultivation system as another experiment, which shows that the combination administration enhances the increasing in cell number in comparison with single administration of AM and VEGF (FIG. 9, panel C). In FIG. 9, the mark "##" denotes p<0.01 in comparison with AM single administration group.

Example 4

Phosphorylation of Akt and eNOS by the Administration of VEGF and AM

Single administration of AM ($10^{-11}$ to $10^{-7}$ M) alone, or administration of AM in combination with VEGF (10 ng/ml) to the cultivating system of human umbilical vein endothelial cell was carried out. Protein was extracted from cells and the phosphorylation of Akt and eNOS was investigated using Western Blot analysis.

The result shows that AM enhanced the phosphorylation of Akt and eNOS by VEGF (FIG. 10). In FIG. 10, panel A shows the phosphorylation of Akt, and panel B shows the phosphorylation of eNOS, respectively. From these results, it was confirmed that AM enhances PI3k-Akt-eNOS pathway, the signal pathway of VEGF.

Example 5

Enhancement of Expression of VEGF Mediated by AM

The lower extremity ischemia model mouse prepared as in Example 2 was sacrificed by cervical dislocation, then femoral muscle sampled, from which protein was extracted and Western Blot analysis was conducted.

Result is shown in FIG. 11. In FIG. 11, panel A shows the Western Blot of VEGF obtained from the AM administration group and control group of lower extremity ischemia model mice, panel B shows the quantified result shown in panel A, panel C shows the Western Blot of VEGF obtained from the lower extremity ischemia model mice prepared from AM homozygous knockout and wild-type mice, and panel D shows the quantified result shown in panel C, respectively.

In the mouse of AM administration group, expression level of VEGF increased from the early stage after the ischemia operation (day 1) (FIG. 11, panel A and B). In contrast, the expression level of VEGF in AM heterozygous knockout mice (AM +/−) decreased in comparison with wild-type (FIG. 11, panel C and D).

Also, the expression of VEGF in human artery endothelial cell (HAEC) was analyzed using RT-PCR.

Figure 12:
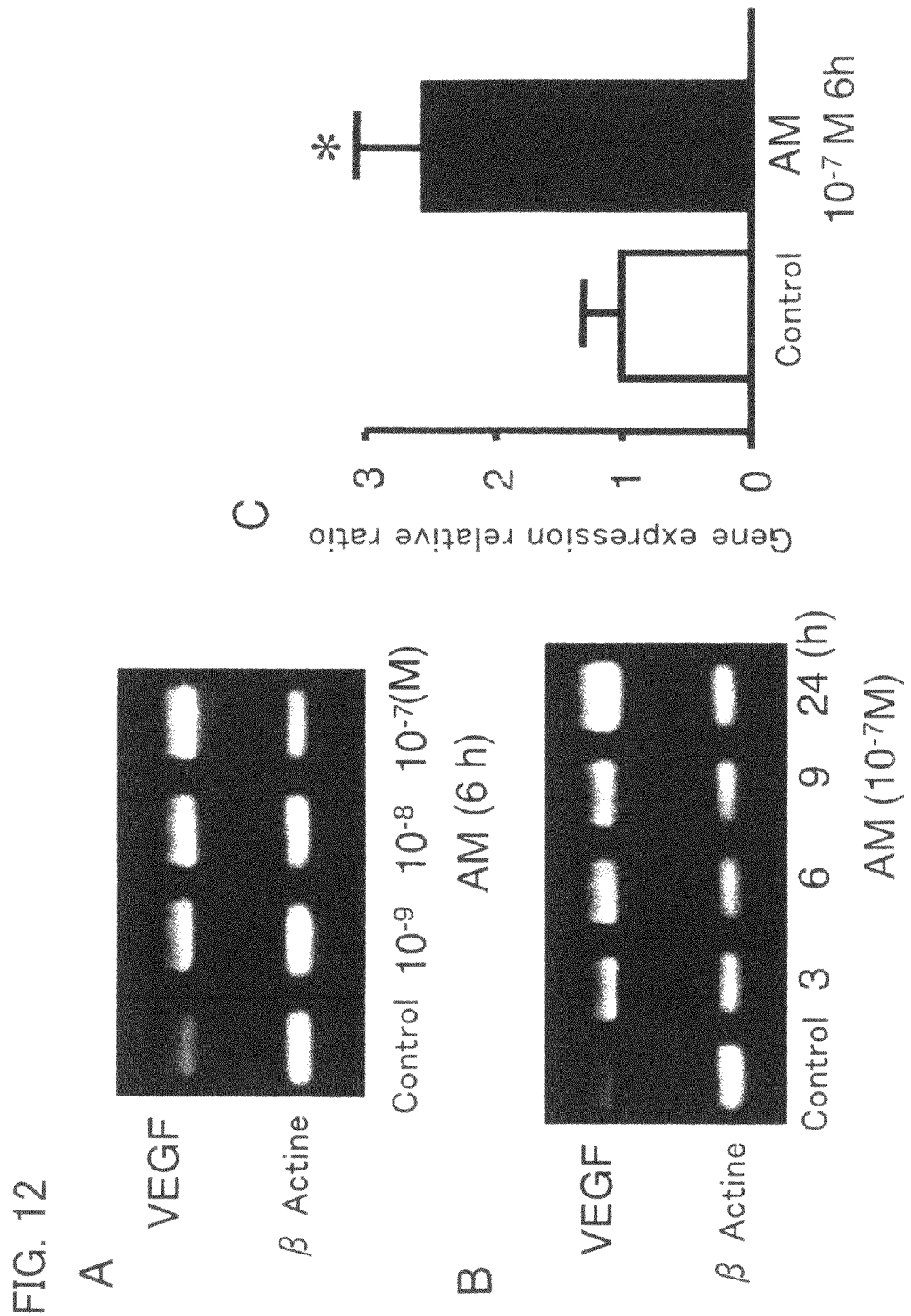
FIG. 12 shows the result of real time PCR showing the expression of VEGF is increased by the administration of AM.

The result is shown in FIG. 12. In FIG. 12, panel A shows the AM concentration dependence of the expression level of VEGF, and panel B shows the AM stimulation time dependence of the expression level of VEGF, respectively. The expression level of VEGF increased concentration- and time dependently upon administrating AM (FIG. 12, panel A and B).

Example 6

Rescue Test Using AM-Knockout Mice and Flk-1-Knockout Mice

In this example, The lower extremity ischemia model mice were prepared as in Example 2, and the recovery of blood flow of the AM heterozygous knockout mice (AM +/−) supplemented with exogenous AM or VEGF.

Figure 13:
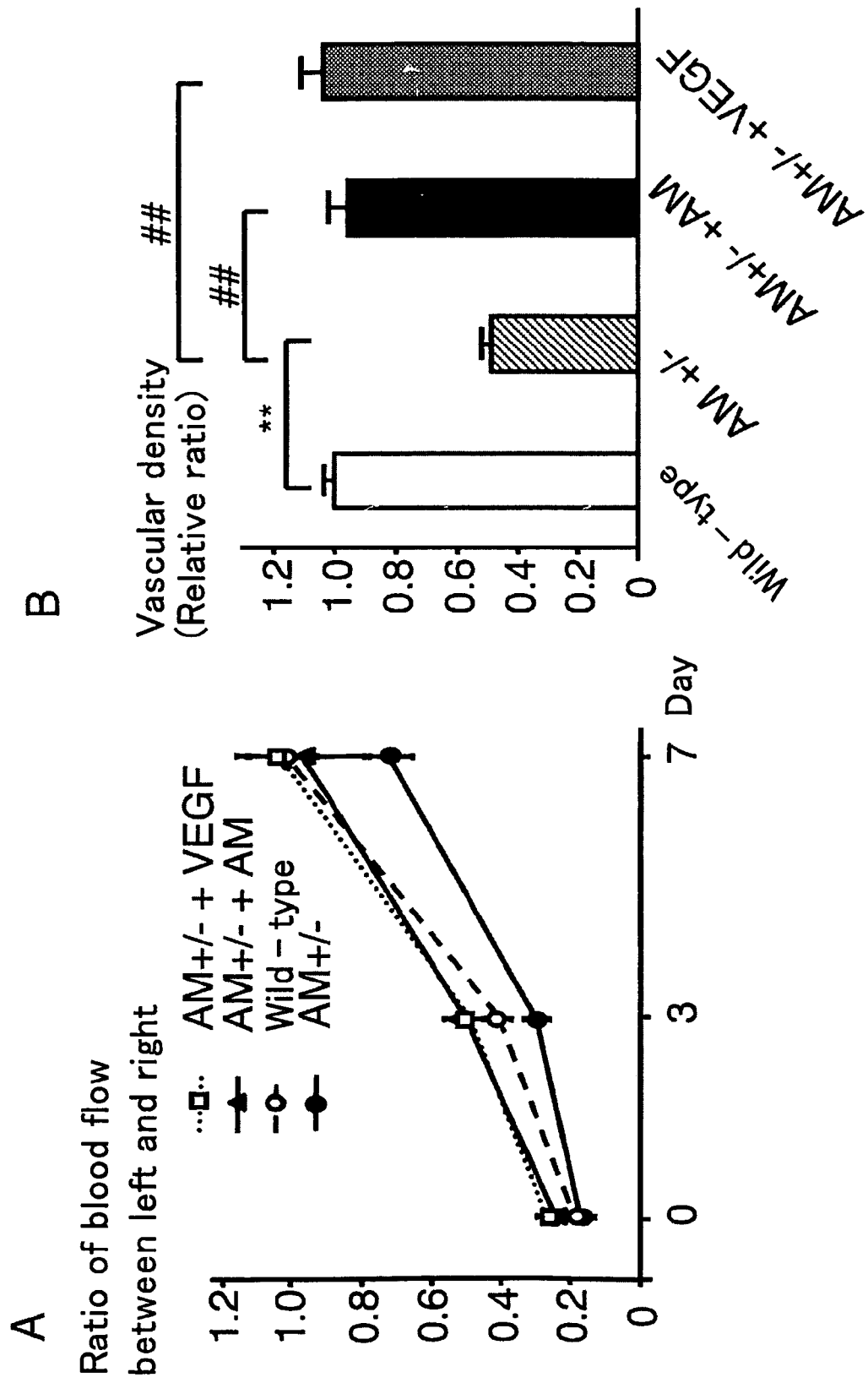
FIG. 13 shows the result of rescue test using AM heterozygous knockout mice.

In AM +/− with decreased expression of AM, the recovery of blood flow decreased (FIG. 13, black circle in panel A). It was confirmed that the supplementation of AM (FIG. 13, black triangle in panel A) or VEGF (FIG. 13, open square in panel A) resulted in the recovery of the angiogenesis effect.

Formation of new blood vessel was also recovered to the level comparable to the wild-type by the supplementation of AM or VEGF to AM +/− (FIG. 13, panel B).

Figure 14:
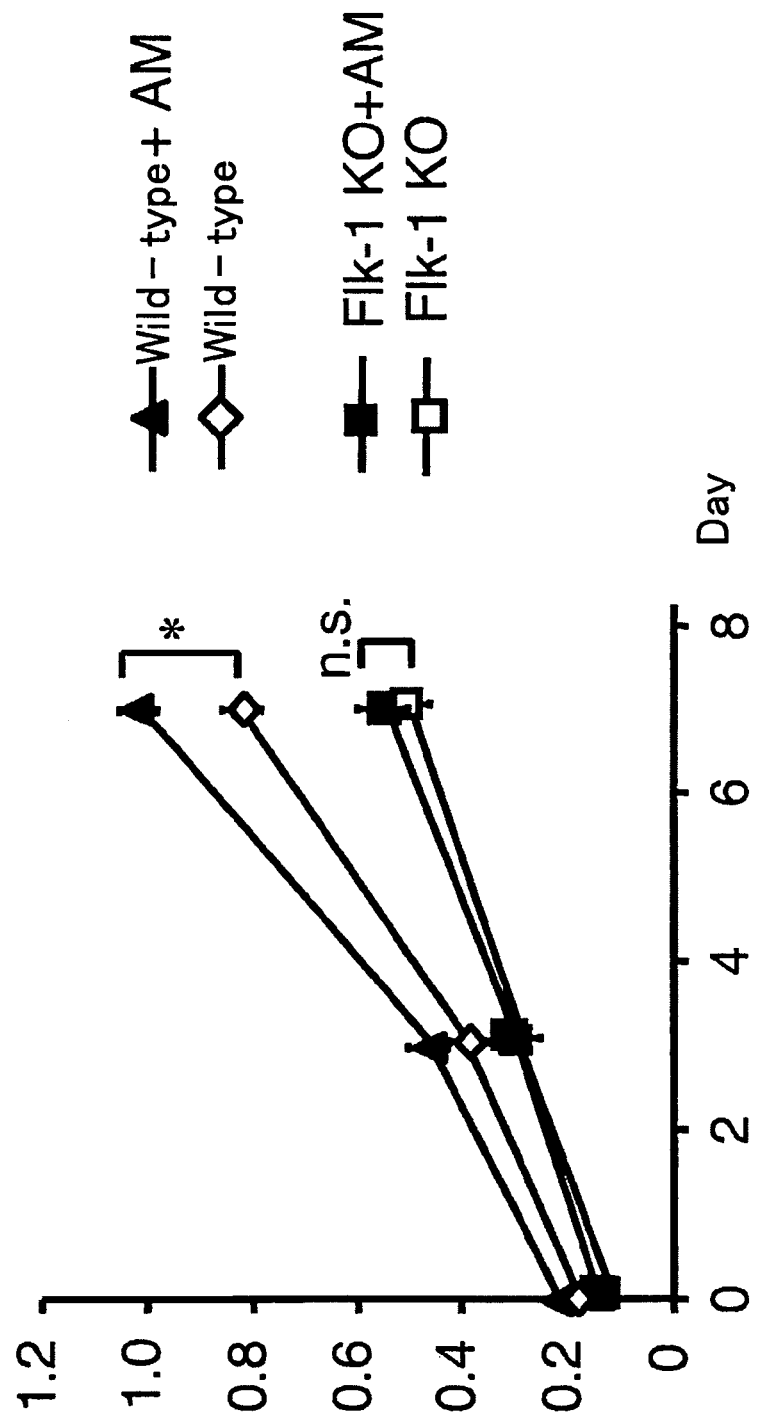
FIG. 14 shows the result of rescue test using Flk-1 knockout mice.

On the other hand, supplementation of AM to Flk-1, a receptor of VEGF knockout mice was conducted as a rescue test opposite to that mentioned above. The recovery of blood flow in Flk-1 knockout mice decreased in comparison with wild-type. The administration of exogenous AM to wild-type mice enhance the recovery of blood flow. However, the administration of exogenous AM to Flk-1 knockout mice showed no recovery of blood flow (FIG. 14).

From these results, it was confirmed also in vivo that angiogenesis effect of AM is mediated by VEGF signal.

Example 7

Detection of the Expressed Gene Using Gene Array

Figure 15:
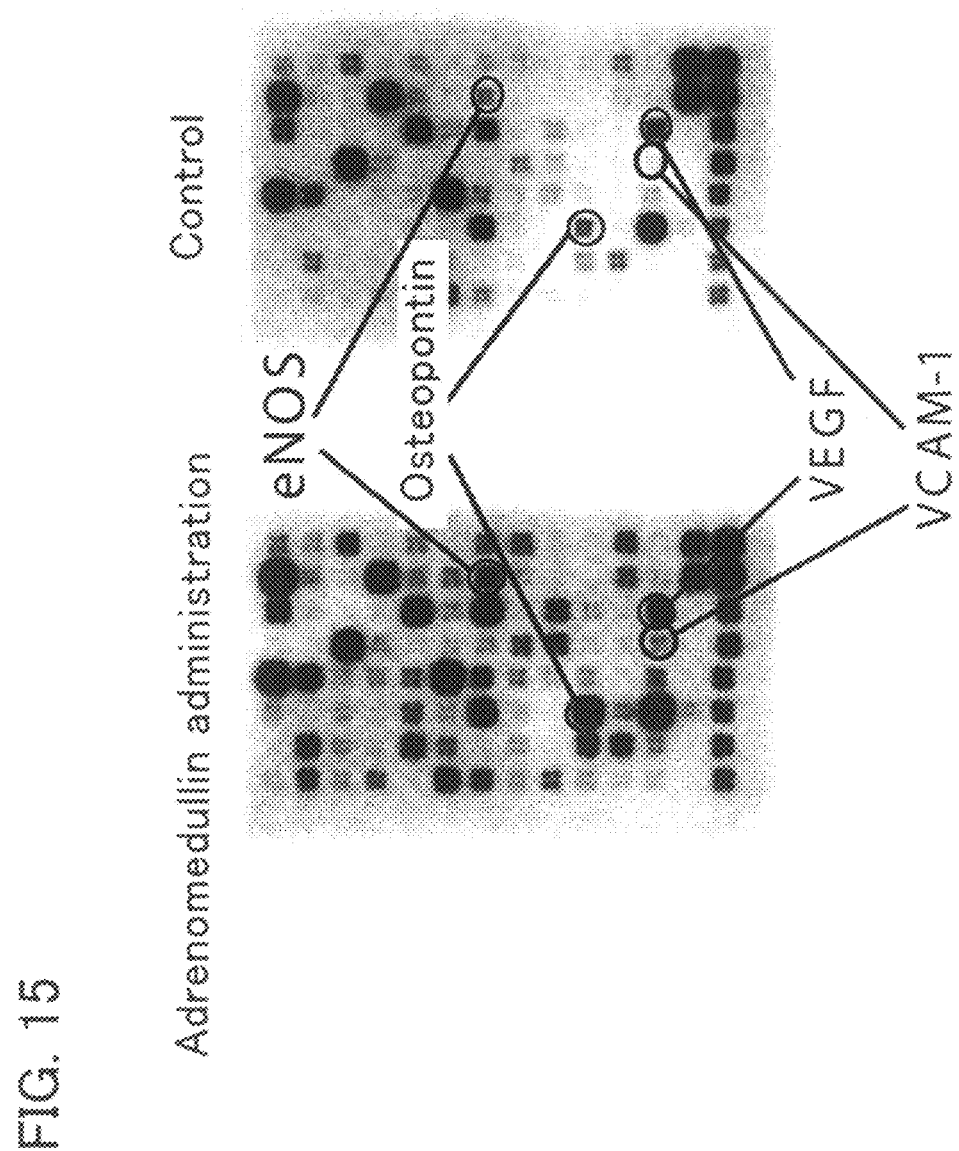
FIG. 15 shows the analysis of gene expression by the treatment with AM using a gene array.

In this Example, the gene group of which expression level changes by the administration of AM were monitored by gene array using the sample form the lower extremity ischemia model mice As a result, AM induced the expression of a plurality of angiogenesis enhancing factors and adhesion factor. FIG. 15 shows an example of gene array. The expression levels of eNOS, Osteopontin, VEGF, VCAM-1 and the like increased by the administration of AM in comparison with control group.

The comparison of AM administration group and control group and the genes expressed at higher level in AM heterozygous knockout mice in comparison with wild-type are shown in Table 2.

TABLE 2

|  | AM(+)/Control | Wild/AM+/− |
|---|---|---|
| eNOS | 1.71 | 2.20 |
| Osteopontin | 1.93 | 7.80 |
| VEGF | 1.50 | 1.70 |
| VCAM-1 | 3.65 | 3.55 |
| TGFβ | 4.04 | 1.70 |
| β-glycan | 6.76 | 3.22 |
| Tie-2 | 3.61 | 2.81 |
| COL18A1 | 2.72 | 2.61 |
| PAI-1 | 1.79 | 1.92 |
| PDGF-A | 5.60 | 6.06 |
| PDGFRβ | 1.58 | 2.08 |

Example 8

In Vitro Vascular Permeability Assay

Figure 16:
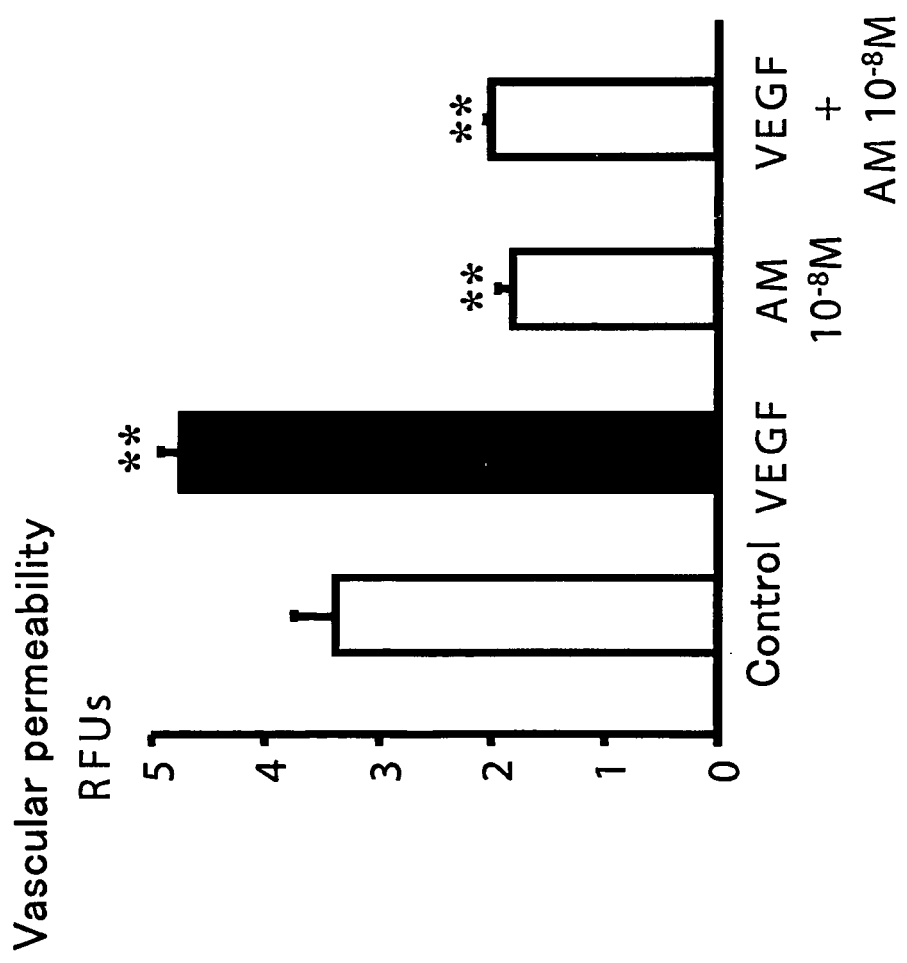
FIG. 16 shows the suppression of vascular permeability by AM.

An insert made of semi-permeable membrane was placed on a cultivation plate, in which HUVEC was cultured so that the cells formed monolayer (EBM-2 medium, 5% $CO_2$, 37° C., 24 hours). The extent of permeability was measured by addition of the substance for the vascular permeability test to the plate on which cell were cultured, followed by the addition of dextran labeled with FITC onto the cell monolayer, allowing it to permeate through the monolayer, and the fluorescence intensity in the plate well solution was measured. These result shows that VEGF enhanced vascular permeability and, in contrast, the addition of AM led to the suppression of vascular permeability. Moreover, the administration of AM in addition to VEGF suppressed the enhancement of vascular permeability by VEGF (FIG. 16).

Example 9

The Lower Extremity Edema Model Mice by Topical Injection of Hyperosomotic Substance Transient edema may be prepared by topical injection of carrageenan, a hyperosmotic substance to pad of foot of mouse. Magnitude of the edema thus formed was evaluated by measuring the thickness of feet pad from time to time.

Figure 17:
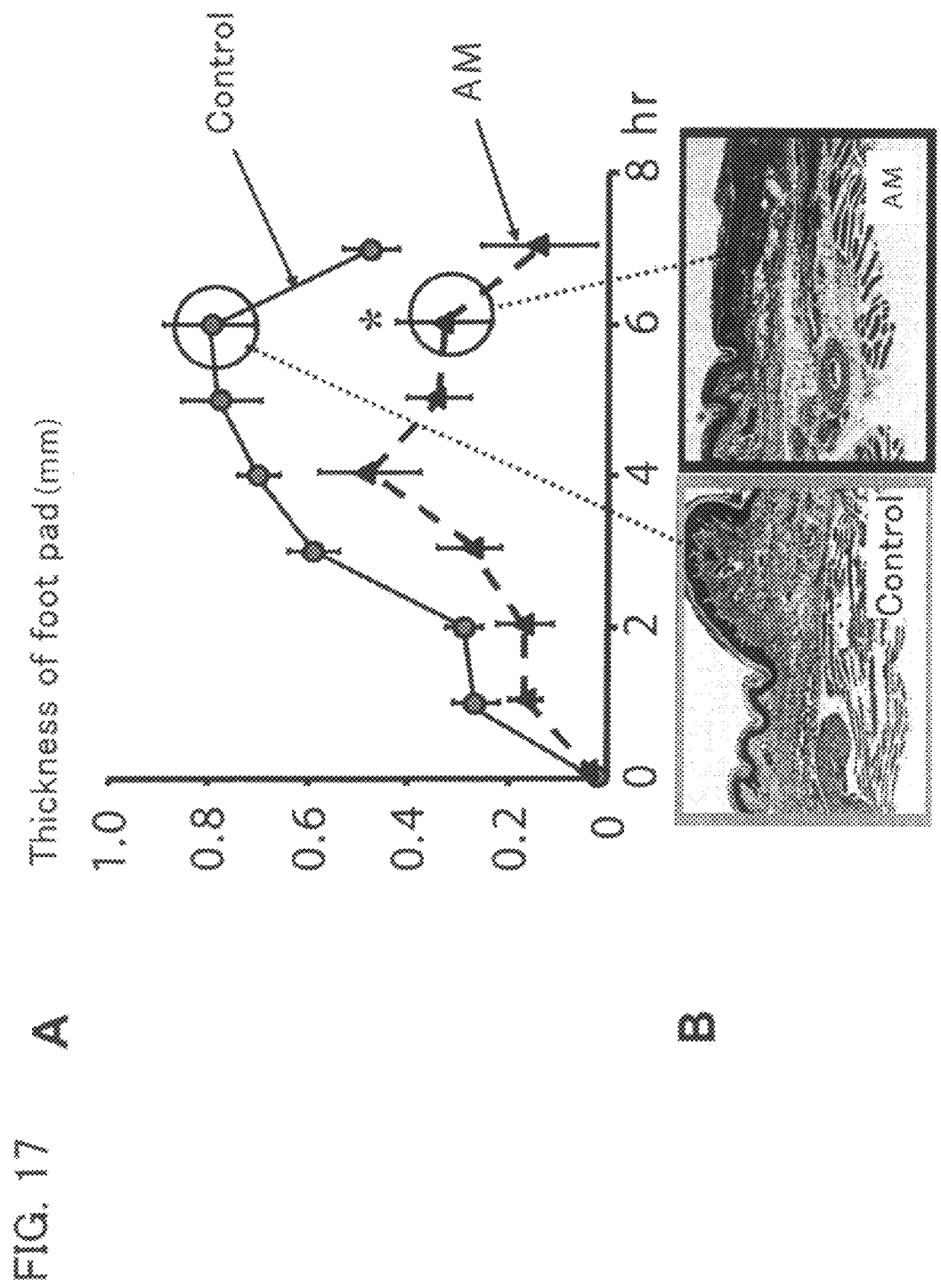
FIG. 17 shows the relief of edema by the administration of AM.

The result shows that edema formed in control group (FIG. 17, black circle), whereas the formation of edema at lower limb was suppressed by continuous administration of AM (FIG. 17, black triangle).

The result of this Example shows that AM suppresses vascular permeability and useful to the treatment of the edema at lower limb.

Example 10

Suppression of Cerebral Edema

Mice were anesthetized with nembutal and then skull was opened. Injury was provided by contacting a cylinder cooled to −80° C. against dura mater. After 24 hours, mice were sacrificed, brain was removed and the increasing in the weight of the brain due to the cerebral edema was quantified. In the similar cerebral edema model, fluorescent-labeled dextran was injected into the tail vein and the leakage of the fluorescence dye out of the vessel in brain was quantified using fluorescent plate reader.

Figure 18:
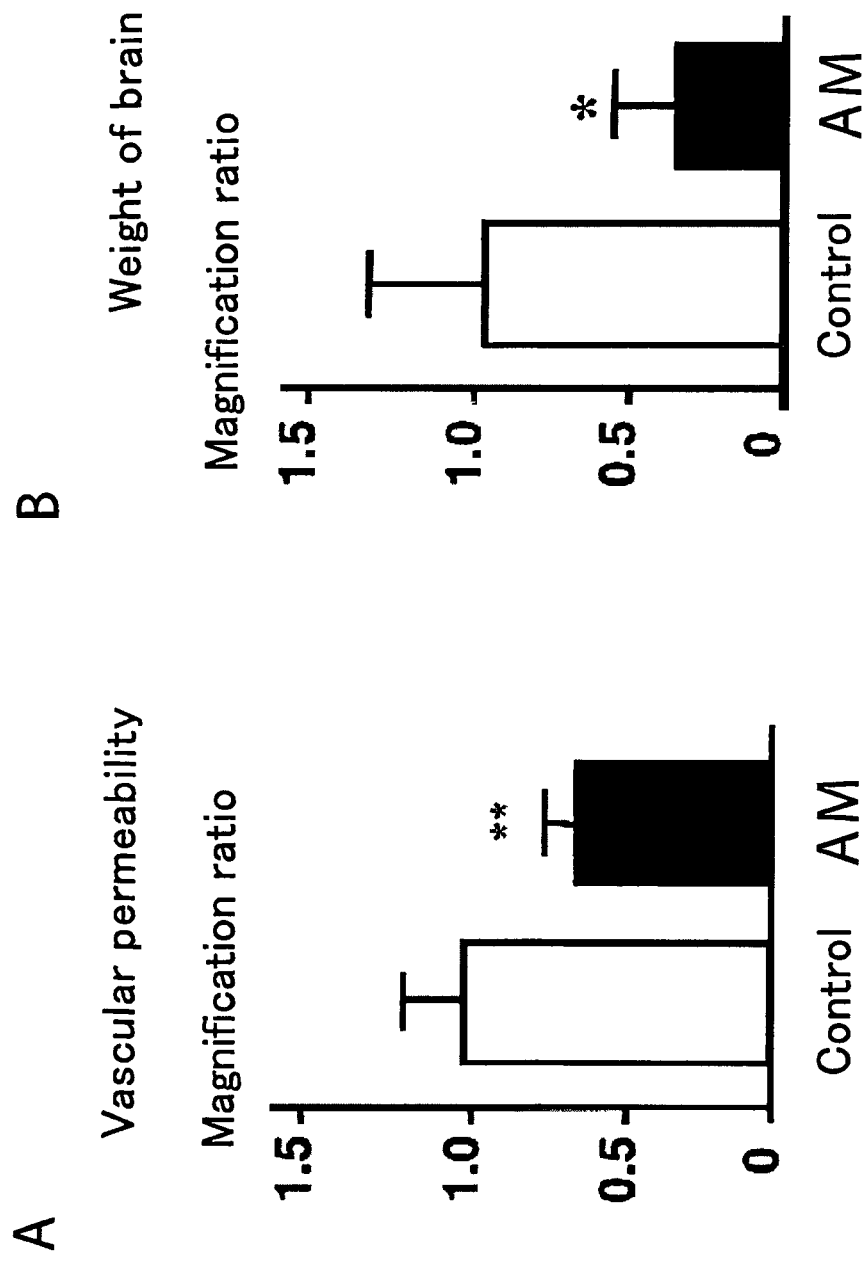
FIG. 18 shows the improvement of cerebral edema by the administration of AM.

The result is shown in FIG. 18. In FIG. 18, panel A shows the result of the measurement of vascular permeability, and panel B shows the result of the measurement of weight of brain. In AM administration group, vascular permeability was suppressed in comparison with control (FIG. 18, panel A), and the weight of brain was also decreased (FIG. 18, panel B). Enhancement of vascular permeability in brain may lead to cerebral edema. Therefore, the result of this Example shows that AM is useful for the treatment of cerebral edema.

Example 11

Preparation of RAMP 2 Gene Knockout Mice

In this Example, adrenomedullin receptor activity-modifying protein 2 (RAMP 2) gene-knockout mice were prepared similar manner to Example 1.

RAMP 2 homozygous knockout mice were lethal at the middle embryonic stage as AM homozygous knockout mice. The reason was edema and hemorrhage due to the abnormality in the development of blood vessel, as described hereafter. AM receptor composes of the combination of CRLR (calcitonin receptor like receptor) and RAMP 2 or RAMP 3. This result shows that RAMP 2 is important as RAMP in the angiogenesis of AM.

Figure 19:
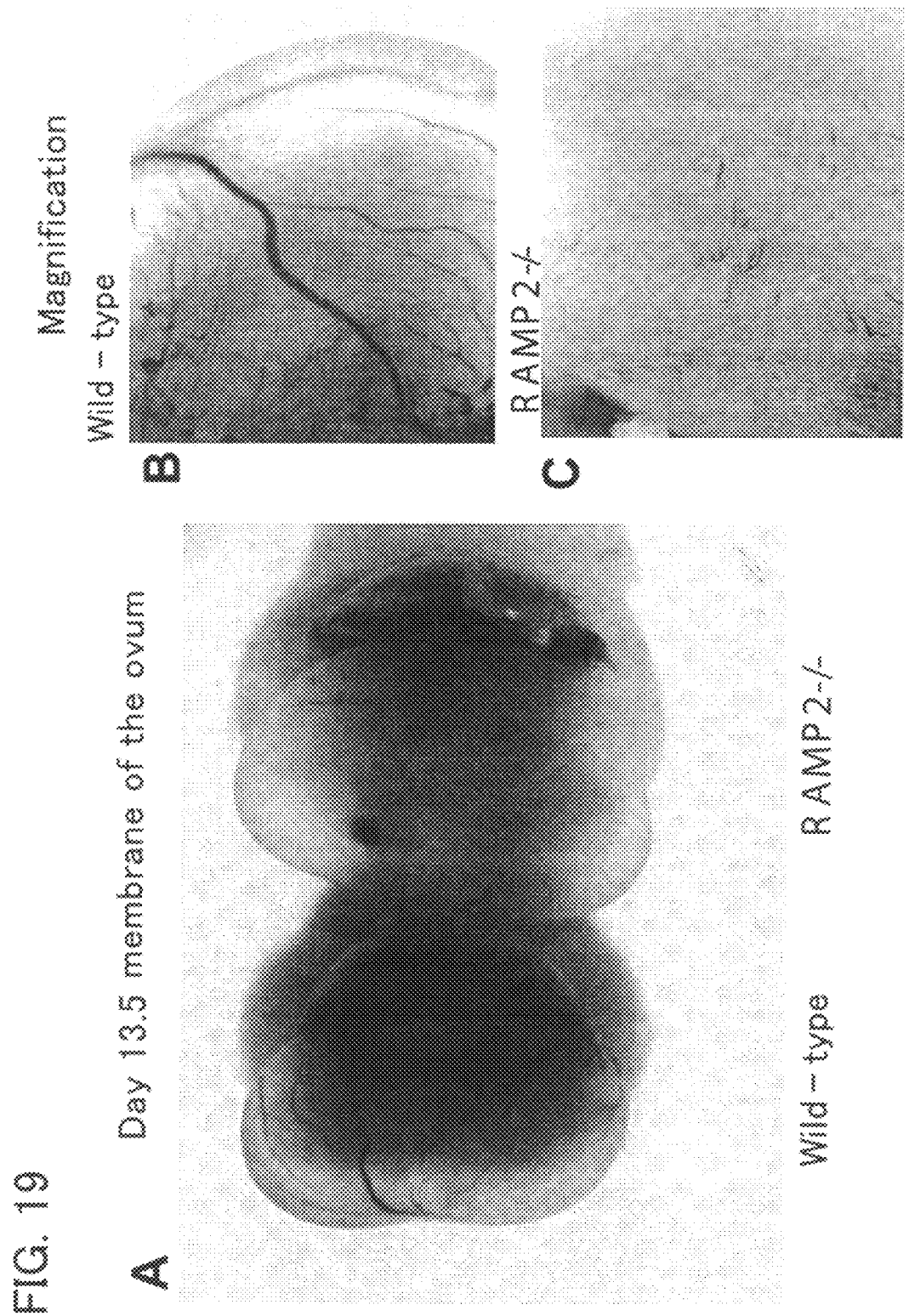
FIG. 19 shows the membrane of the ovum of RAMP 2 homozygous knockout mouse.
Figure 21:
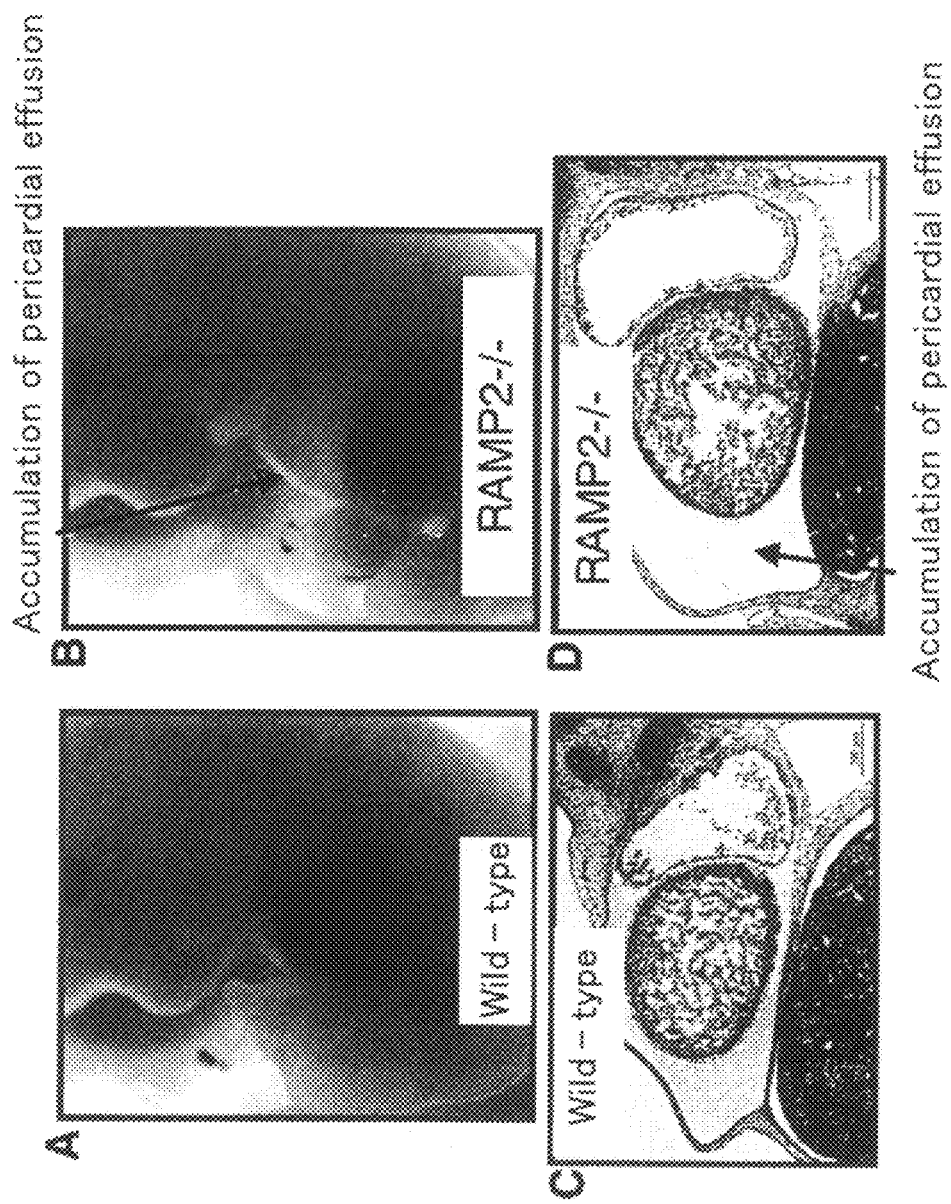
FIG. 21 shows the accumulation of pericardial effusion in the embryo of RAMP 2 homozygous knockout mice at embryonic day 13.5 embryos.

Membrane of the ovum in RAMP 2 homozygous knockout mice (RAMP 2−/−) was expanded in comparison with wild-type (FIG. 19, panel A). The development of vitelline artery on the membrane of the ovum in RAMP 2−/− (FIG. 19, panel C) was suppressed in comparison with wild-type (FIG. 19, panel B) (FIG. 19, panel C). Moreover, in RAMP 2−/− edema occurred systemically in comparison with wild-type at embryonic day 13.5 embryos (FIG. 20). The accumulation of pericardial effusion was also observed in RAMP 2−/− (FIG. 21, panel B, D). In FIG. 21, panel C and D show micrograph of the slice of heart and cardiac sac of wild-type mouse and RAMP 2−/−, respectively.

Figure 22:
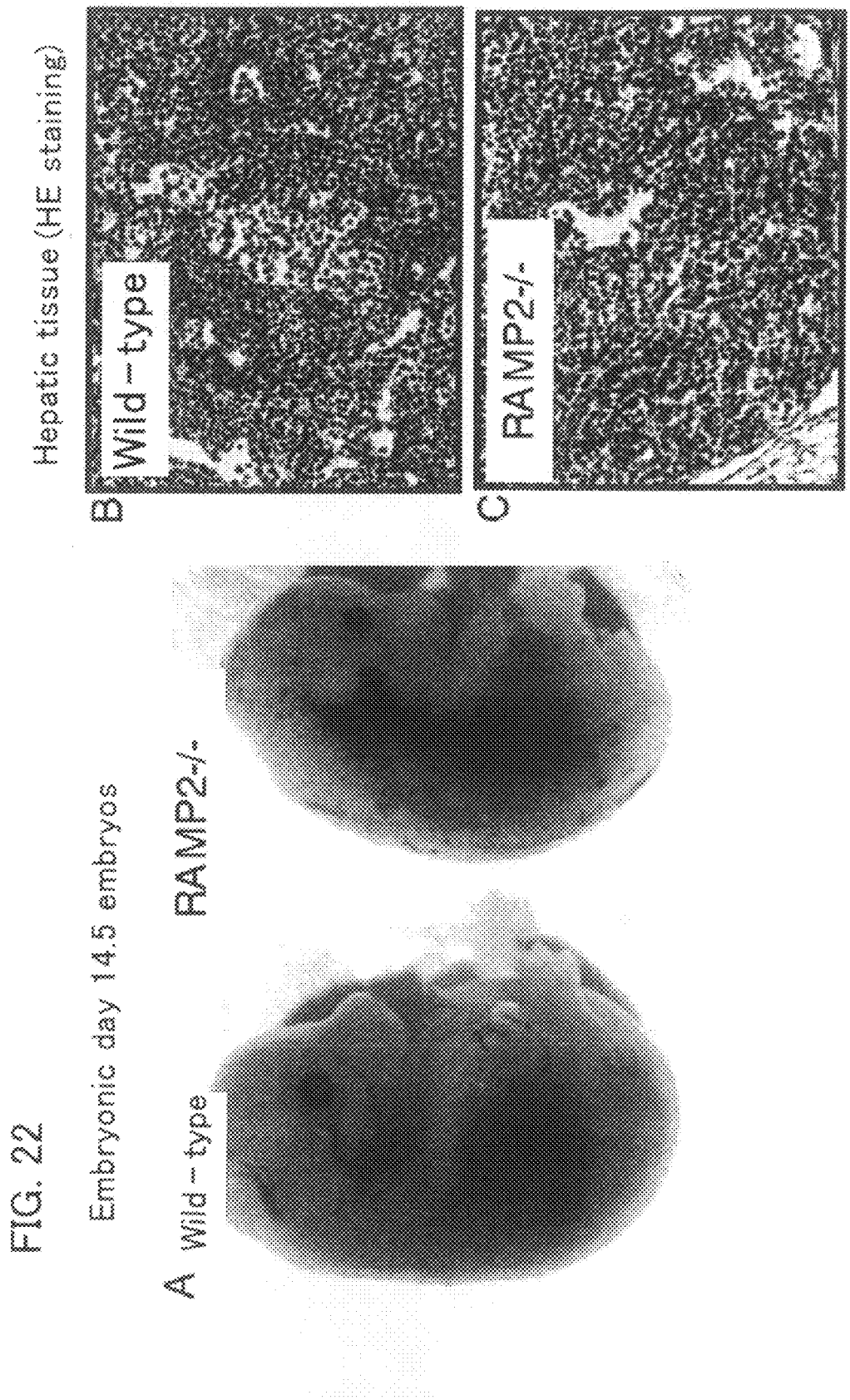
FIG. 22 shows the hemorrhage in the embryo of RAMP 2 homozygous knockout mice at embryonic day 14.5 embryos.

In the embryos of RAMP 2−/− at embryonic day 14.5, significant hemorrhage was observed (FIG. 22). In FIG. 22, panel A shows the photograph of embryos at embryonic day 14.5, panel B and C show the HE stained image of hepatic tissues of wild-type mouse and RAMP 2−/−, respectively. In the hepatic tissue, hemorrhage due to the collapse of vascular architecture was observed in RAMP 2−/−.

These changes was similar to those observe in adrenomedullin homozygous knockout mice and it was shown that adrenomedullin-RAMP 2 signal is indispensable for normal vascular formation.

Example 12

Abnormality in the Blood Vessel of RAMP 2 Homozygous Knockout

Figure 23:
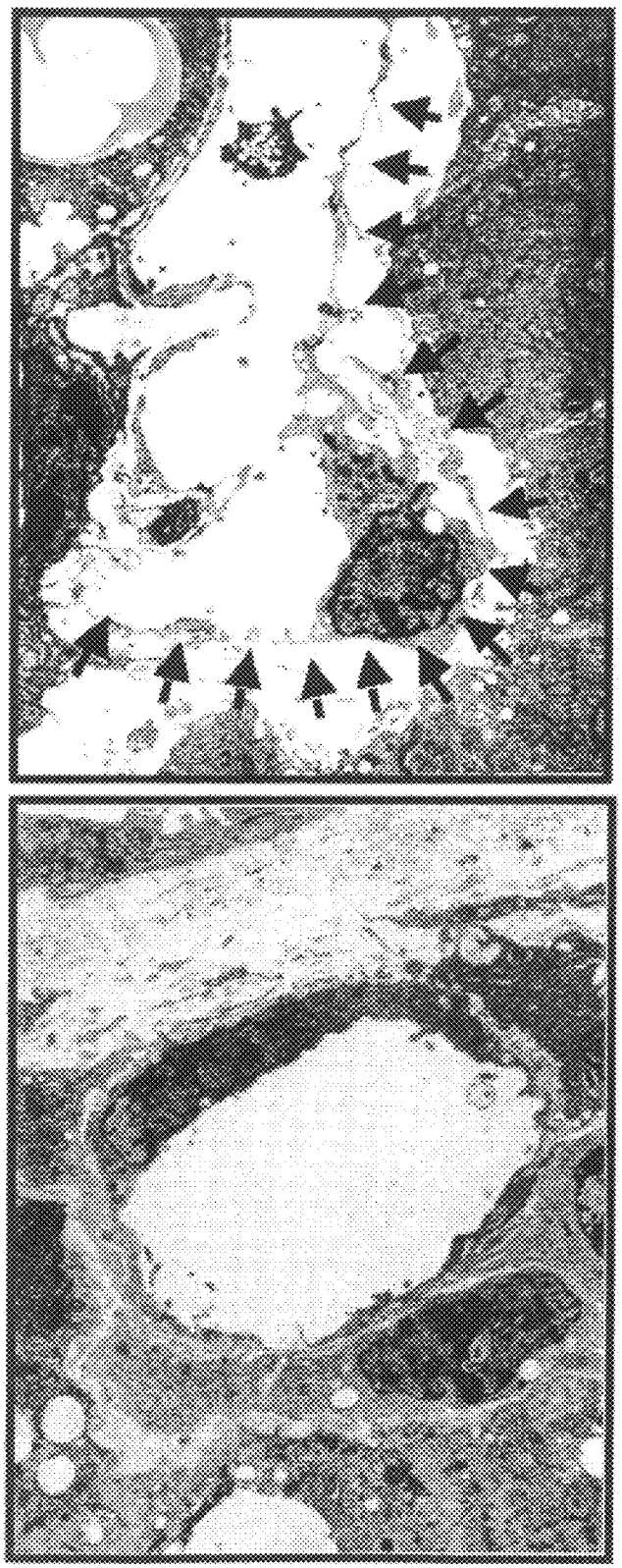
FIG. 23 shows the electric micrographs of vitelline artery of RAMP 2 homozygous knockout mice.
Figure 24:
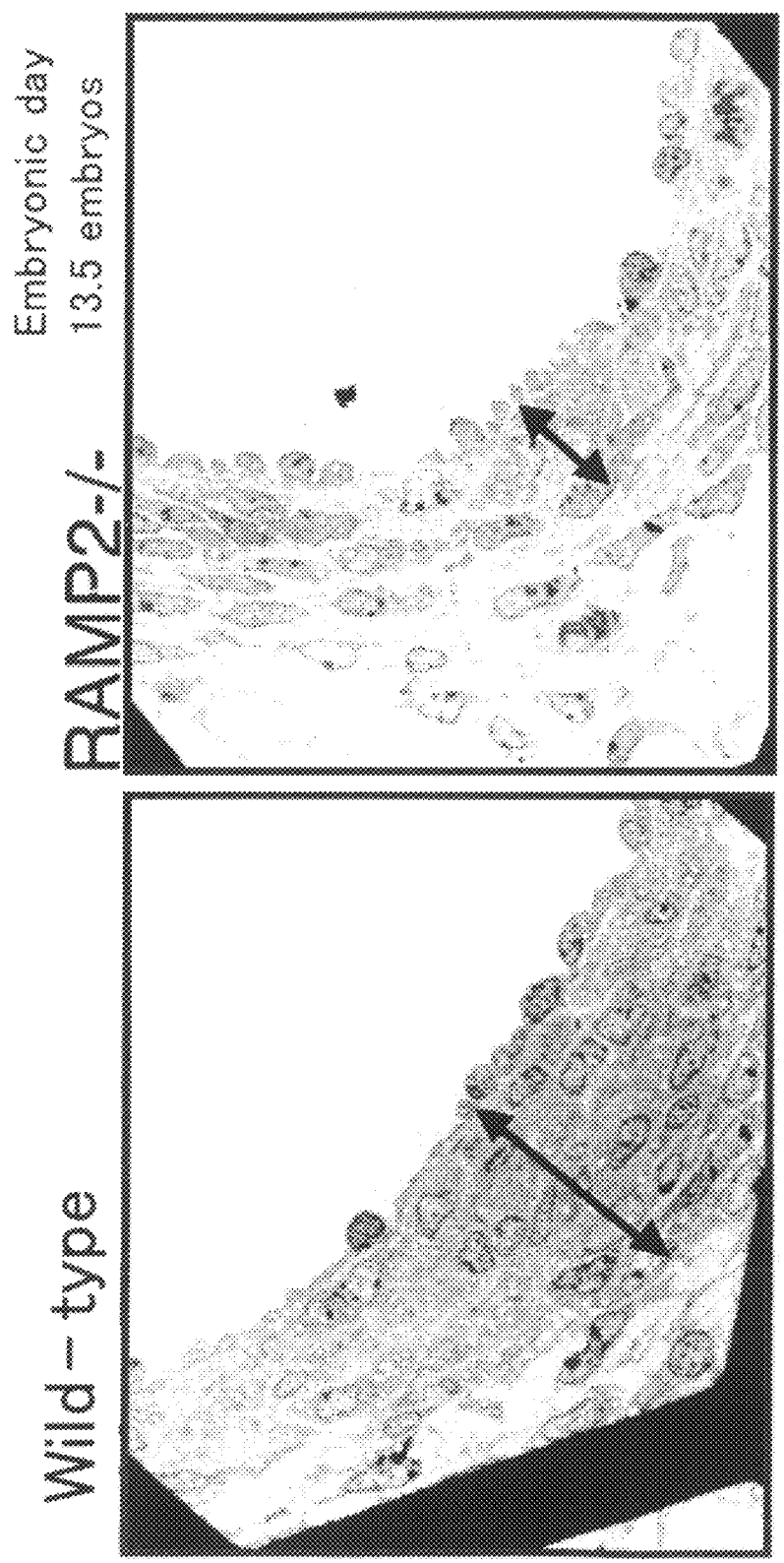
FIG. 24 shows the electric micrographs of aortic wall of RAMP 2 homozygous knockout mice.

In this Example, vascular formation in RAMP 2 homozygous knockout mouse (RAMP 2−/−) at embryonic day 13.5 embryos was analyzed in detail. Electron microscopic observation showed that the image in which avulsion of endothelial cells of vitelline artery from basal membrane was observed (FIG. 23, arrow). moreover, in aorta of RAMP 2−/−, vascular smooth muscle layer was thinner in comparison with that of wild-type (FIG. 24, arrow).

Figure 25:
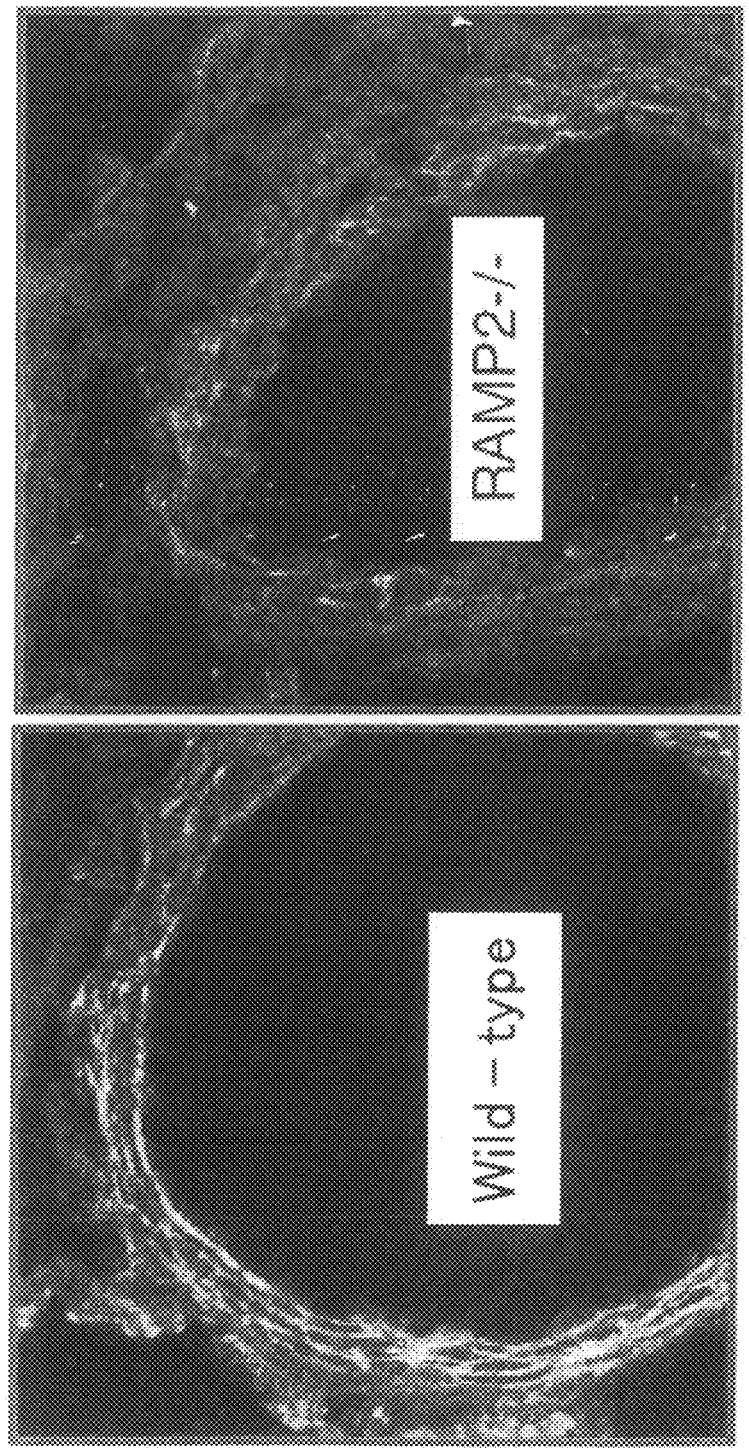
FIG. 25 shows the fluorescent immunohistochemical staining of aortic wall of RAMP 2 homozygous knockout mice.

Immunohistochemical fluorescence staining of aorta showed the decreasing in the expression level collagen 4 and α actin in the vascular wall was observed (FIG. 25). Such abnormality in blood vessel causes the hemorrhage and edema in RAMP 2−/− and it was shown that the adrenomedullin-RAMP 2 signal is indispensable for the stabilization of vascular formation.

Example 13

Figure 26:
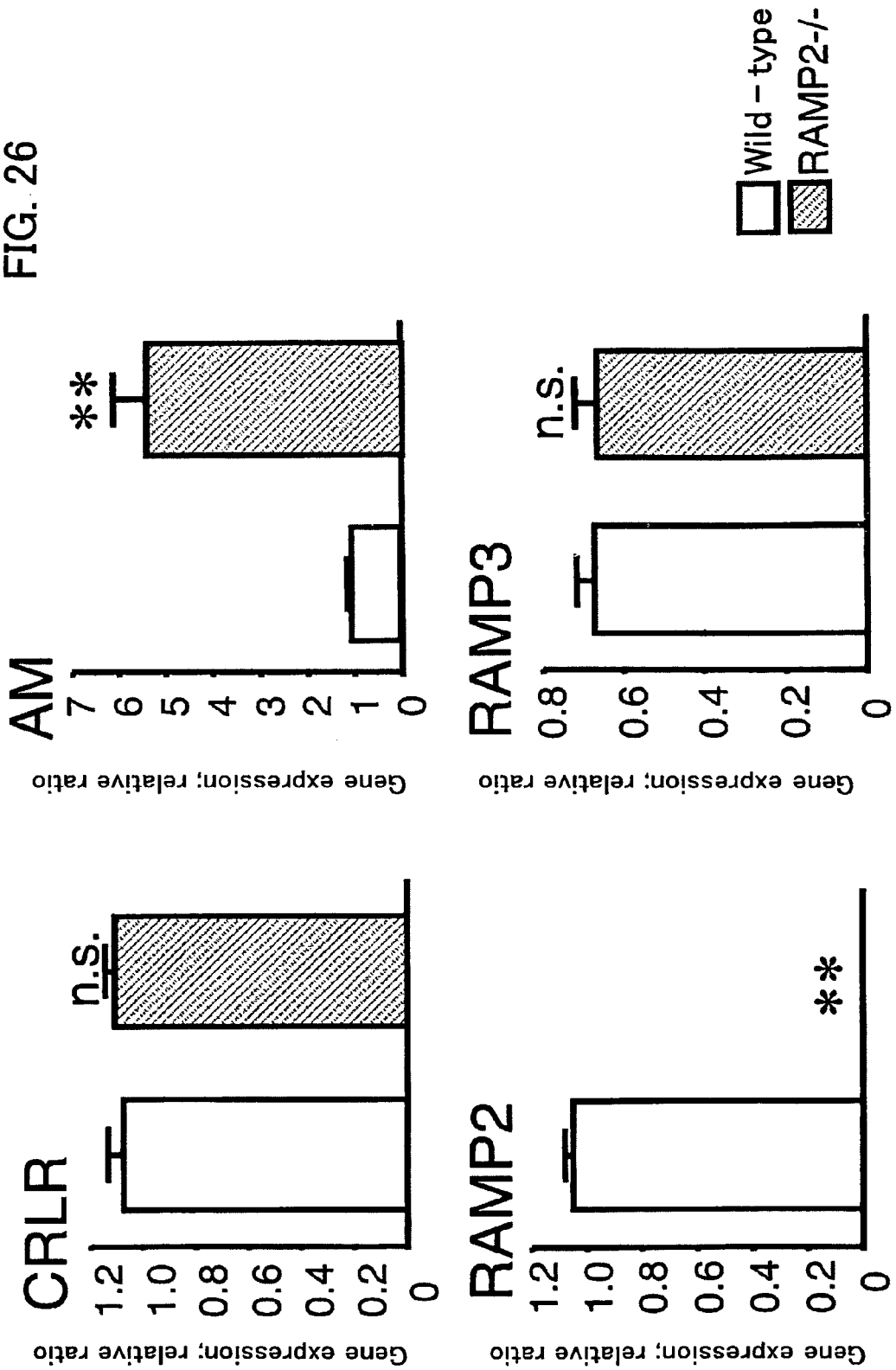
FIG. 26 shows the comparison of the change of gene expression in mice embryos at embryonic day 13.5 embryos between wild-type mice and RAMP 2 homozygous knockout mice.

Change in the Expression of Gene in Embryos of RAMP 2 Homozygous Knockout and Umbilical Artery Change in the expression of gene was investigated by real-time PCR technique using the sample of embryonic day 13.5 embryos of mouse. Compensatory increase in the expression of adrenomedullin in embryos of RAMP 2 homozygous knockout mouse (RAMP 2−/−) as adrenomedullin-RAMP 2 signal was disappeared. On the other hand, no change was observed in the expression of CRLR, an adrenomedullin receptor, and RAMP 3, another adrenomedullin receptor activity-modifying protein (FIG. 26).

These results shows that there is no complementary between RAMP 2 and RAMP 3, and adrenomedullin-RAMP 2 signal is indispensable for the normal vascular formation.

Figure 27:
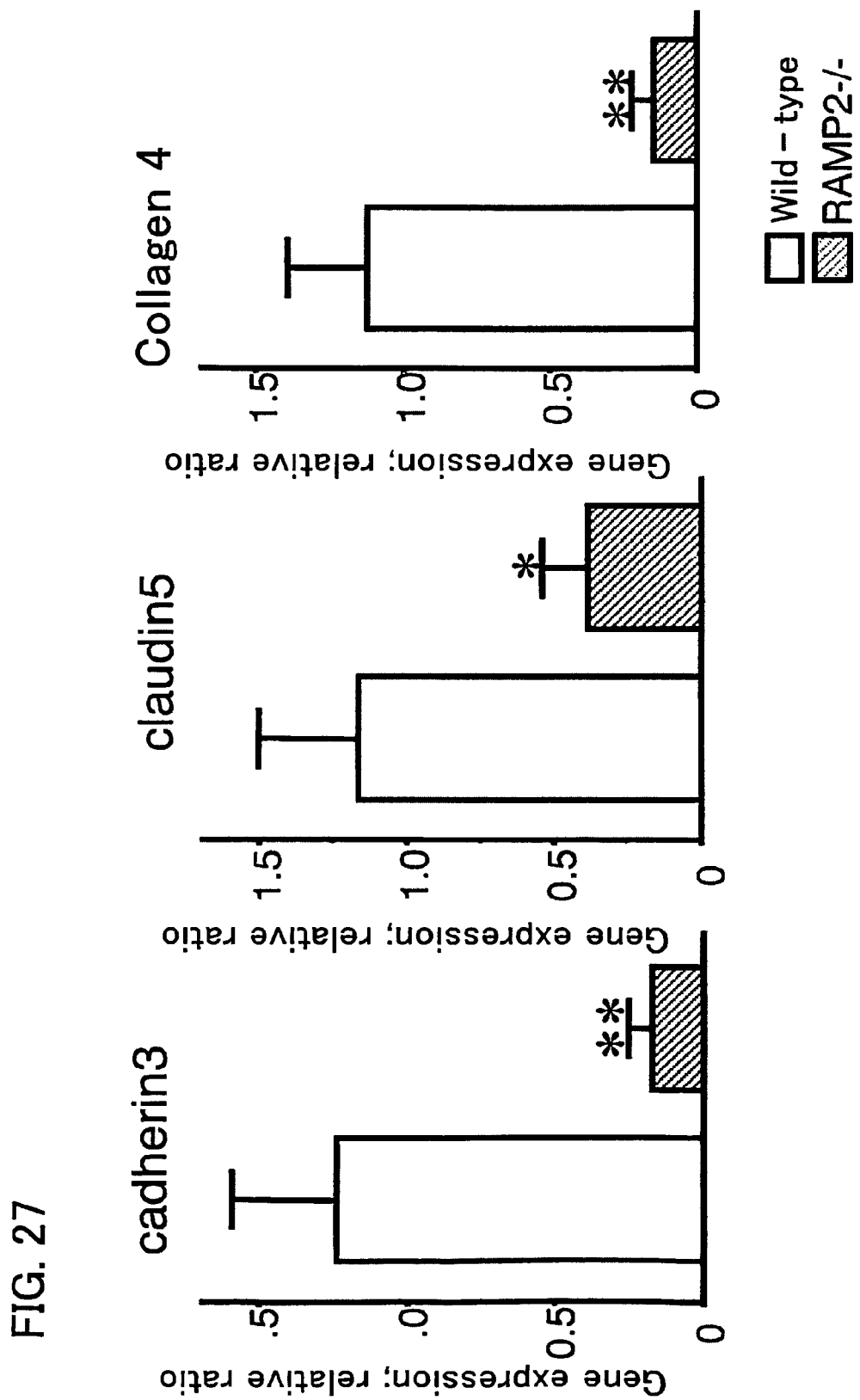
FIG. 27 shows the comparison of the change of gene expression in mice umbilical arteries at embryonic day 13.5 embryos between wild-type mice and RAMP 2 homozygous knockout mice.

In addition, gene expression in mouse umbilical artery at embryonic day 13.5 embryos was investigated using real-time PCR. As a result, in RAMP 2 homozygous knockout, decreasing in the expression of cadherin 3 and claudin 5, adhesion factors; and collagen 4, major component of basal membrane was confirmed (FIG. 27).

From these results, it was shown that adrenomedullin-RAMP 2 signal system contributes to cellular adhesion, stabilization of vascular basal membrane structure, and stabilization of vascular structure.

Example 14

Measurement of Expression Levels of CRLR, AM, RAMP 2 and RAMP 3

(1) The expression levels of CRLR, AM, RAMP 2 and RAMP 3 in wild-type mouse embryos were measured using real-time PCR technique.

Measurements were conducted at embryonic days of 11.5 (E 11.5), 12.5 (E 12.5), 13.5 (E 13.5) and 14.5 (E 14.5).

Figure 28:
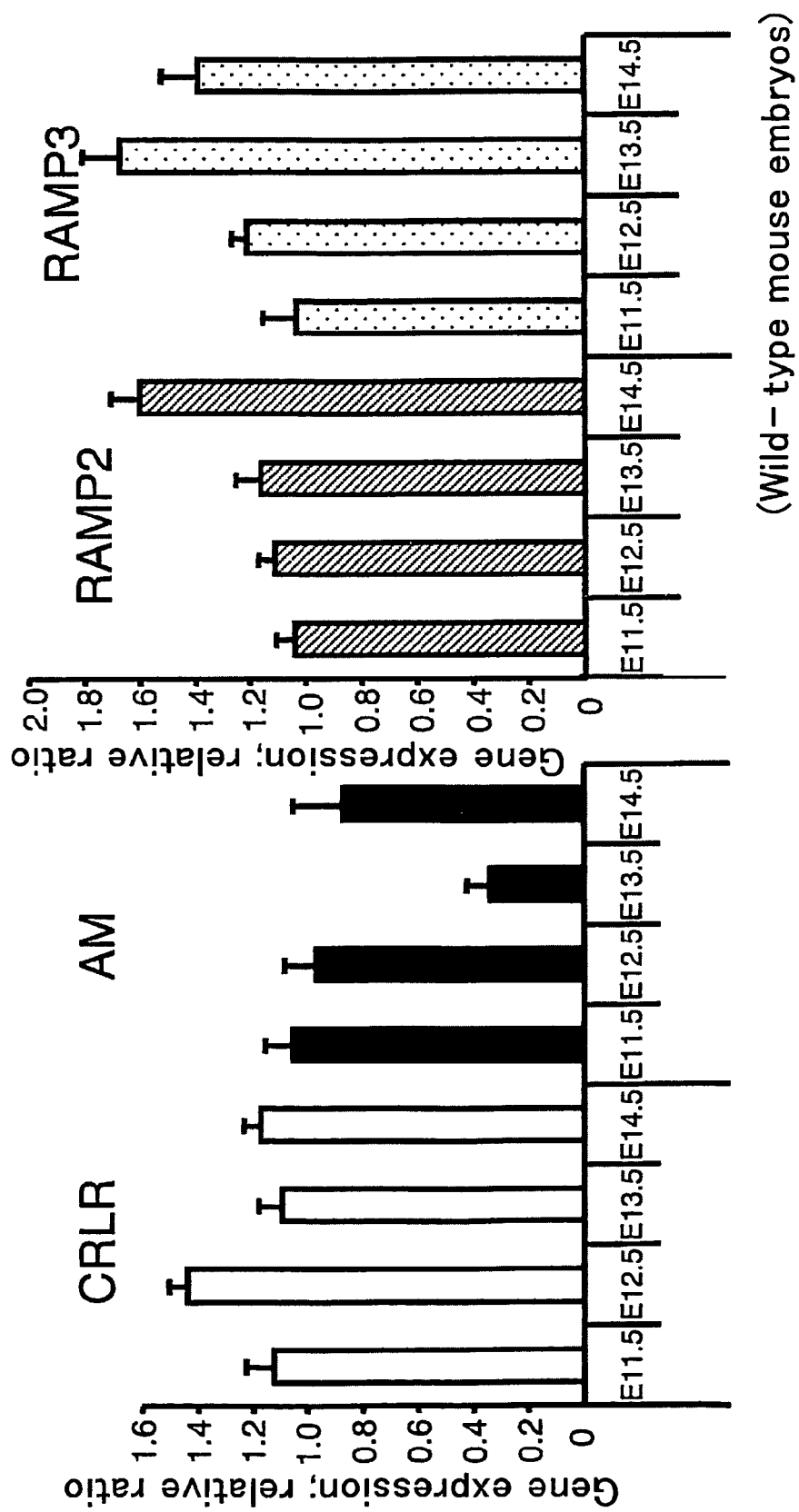
FIG. 28 shows the time course of the expression of CRLR, AM, RAMP 2 and RAMP 3 in the developing stage of the embryos of wild-type mice.

It was shown that the expression of RAMP 2 increased in the middle embryonic stage (FIG. 28).

(2) Then AGM (aorta-gonad-mesonephros region) at embryonic day 10.5 embryos cultured on OP 9 cells was stained immunohistochemically using PECAM-1, which showed that angiogenesis in cultured embryonic AGM decreased in RAMP 2 homozygous knockout mouse (FIG. 29).

From the result, it is shown that RAMP 2 is indispensable for angiogenesis.

Example 15

Gene Expression in HUVEC Cultured on Matrigel (1) Adrenomedullin was administered exogenously to HUVEC cultured on Matrigel. After stimulating for 24 hours, the cell was recovered and RNA was extracted. The expression of claudin 5 gene was investigated using real-time PCR technique.

Figure 30:
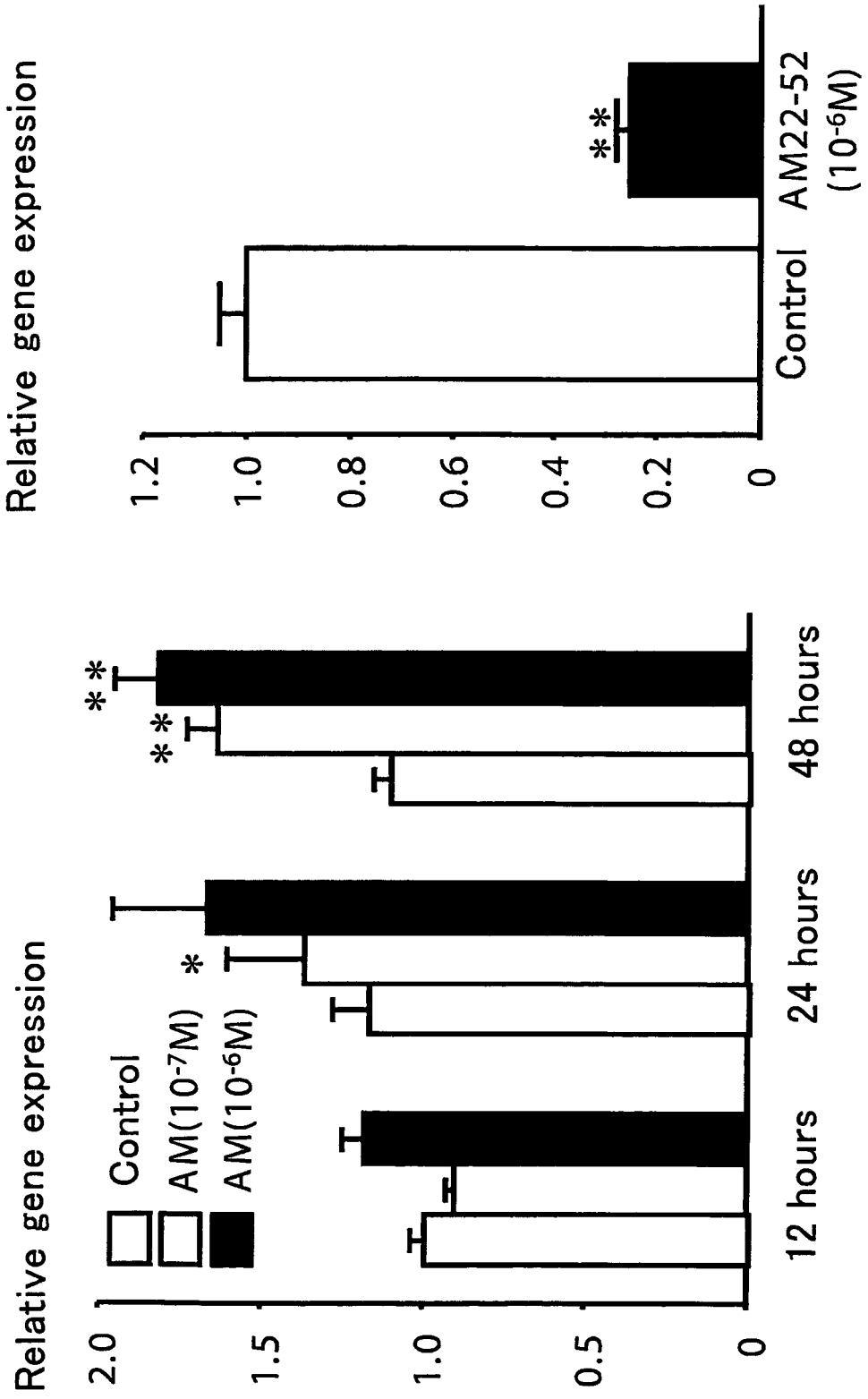
FIG. 30 shows the gene expression level of claudin 5 in HUVEC cultured on Matrigel administered AM or AM 22-52, an AM antagonist.

Results are shown in FIG. 30.

In FIG. 30, left panel shows the relative expression level of claudin 5 twelve hours, 24 hours and 48 hours after stimulus.

AM administration enhanced the expression of claudin 5 in endothelial cell (FIG. 30, left panel).

(2) "AM 22-52", a truncated form of AM consisting of from 22 to 52 amino acid sequence was administered to HUVEC cultured on Matrigel to investigate the gene expression level.

As a result, administration of "AM 22-52" adversely decreased the expression level of claudin 5 (FIG. 30, right panel).

Example 16

Expression Level of RAMP 2, RAMP 3, CRLR and AM in Aorta and Heart of RAMP 2+/−

(1) Expression level of RAMP 2, RAMP 3, CRLR and AM in aorta and heart of RAMP 2 heterozygous knockout mouse (RAMP 2+/−) and wild-type adult was investigated using real-time PCR technique.

As a result, it was shown that the expression level of RAMP 2 in cardiovascular system (aorta and heart) in RAMP 2+/− decreased by half.

Figure 31:
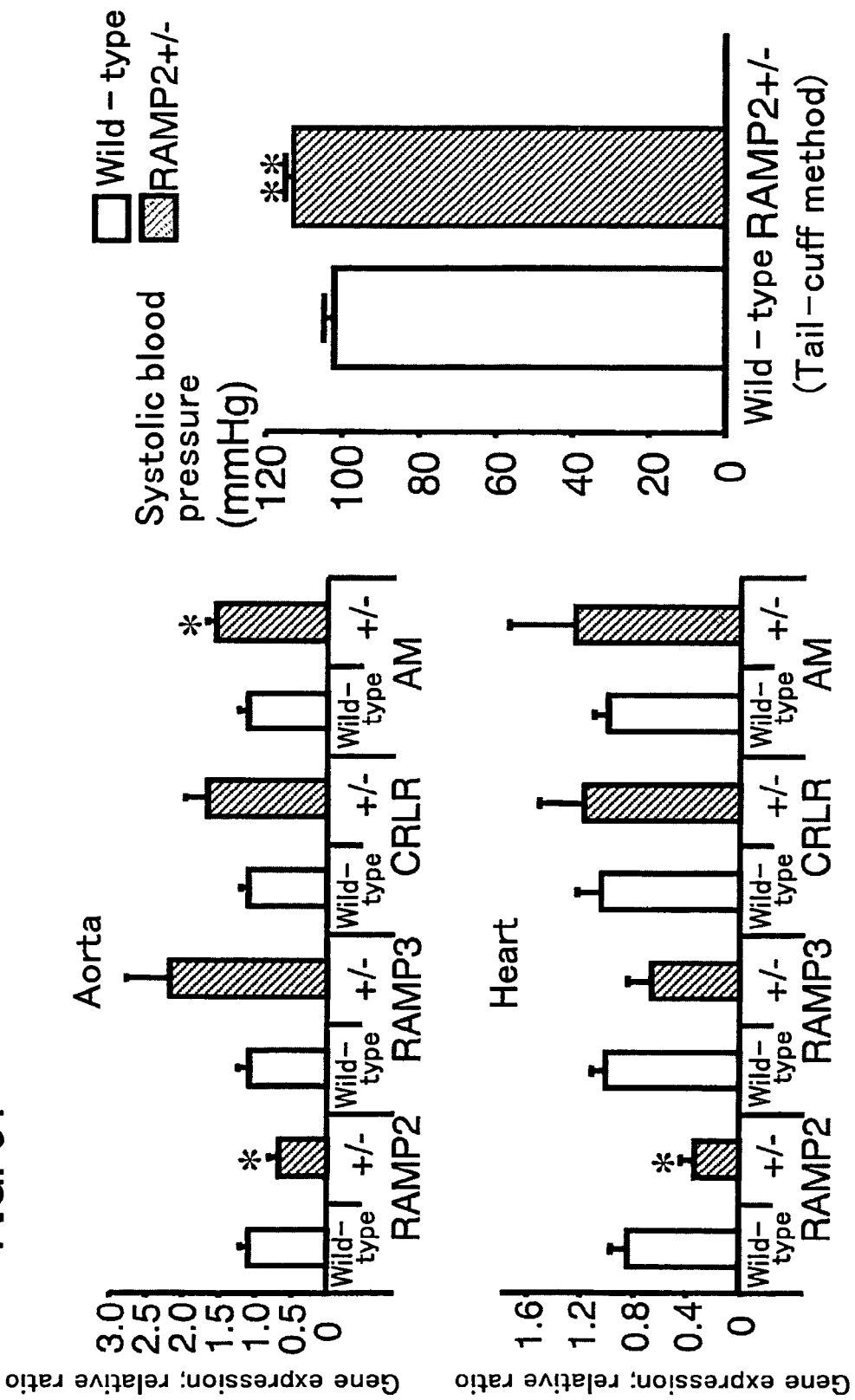
FIG. 31 shows the measurement of the expression levels of RAMP 2, RAMP 3, CRLR and AM in aorta and heart of adult RAMP 2 heterozygous mice, and the measurement of blood pressure of adult RAMP 2 heterozygous knockout mice and wild-type mice.

Systolic blood pressure of mice was measured using tail-cuff, it was shown that the systolic blood pressure of RAMP 2+/− mice was significantly higher than that of wild-type. That is, it was shown that the expression of RAMP 2 was suppressed in RAMP 2+/−, resulting in higher blood pressure (FIG. 31, right panel).

(2) Matrigel Plug Assay Using RAMP 2+/−

Matrigel containing bFGF was injected subcutaneously to a mouse. A week later, the skin at the injection cite was cut open and the new blood vessel penetrated into Matrigel was observed.

Figure 32:
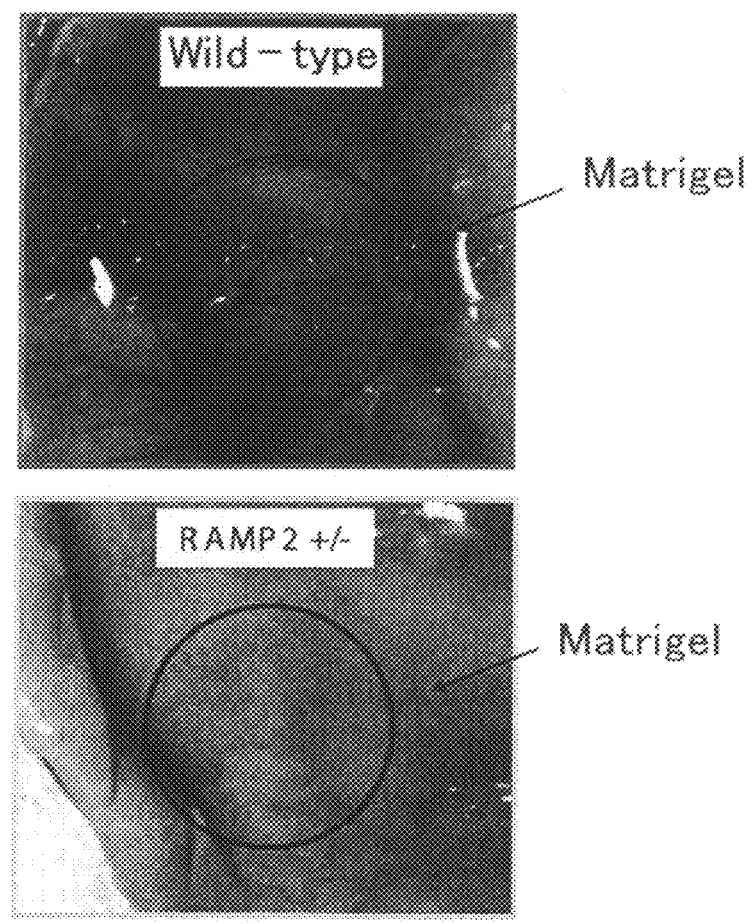
FIG. 32 shows the result of Matrigel plug assay using adult RAMP 2 heterozygous knockout mice.
Figure 33:
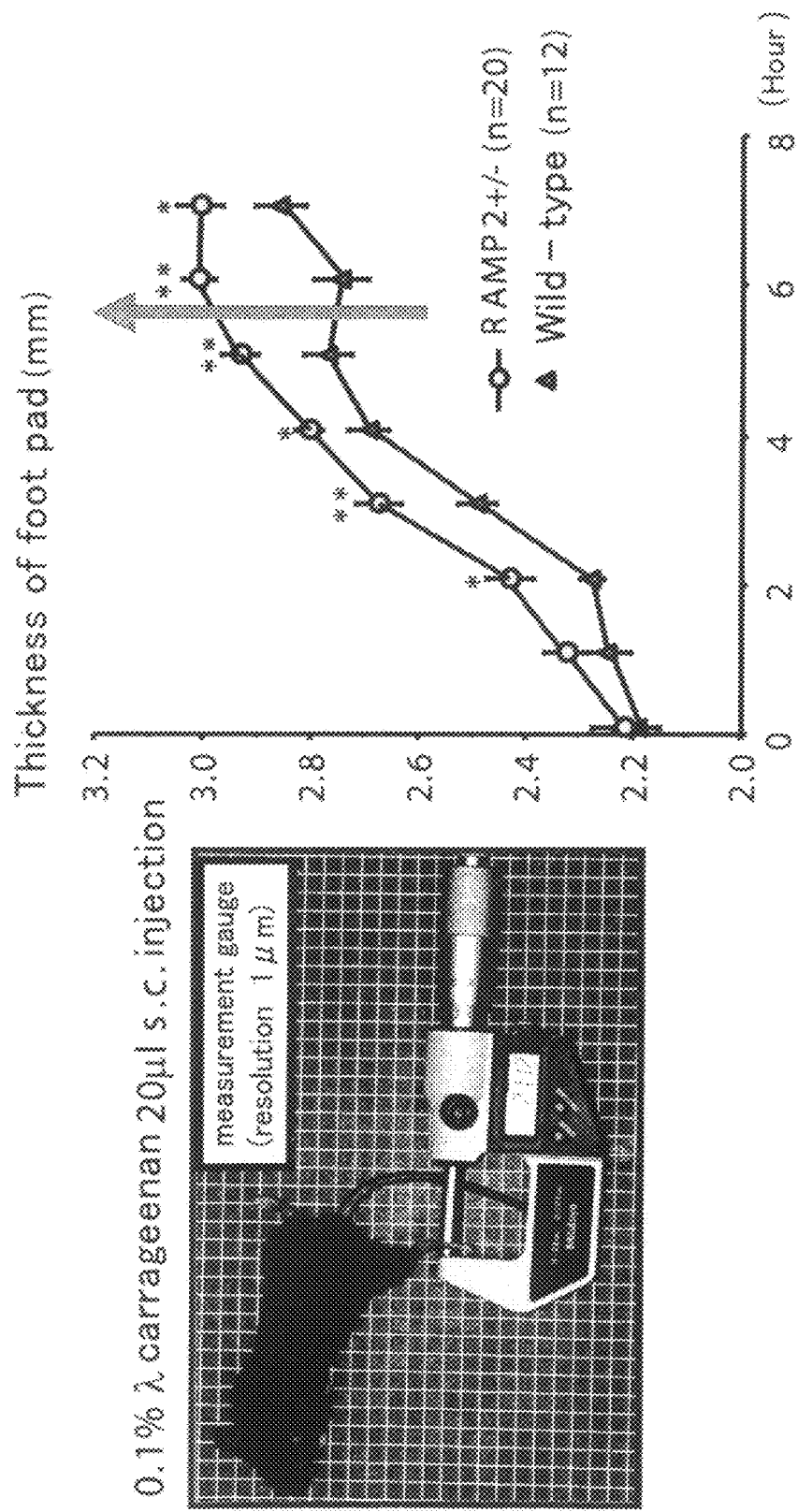
FIG. 33 shows the models of edema of the lower extremities by injecting hyperosmotic substances.

As a result, it was shown that angiogenesis decreased in RAMP 2+/− (FIG. 32).

(3) The Lower Extremity Edema Model by Topical Injection of Hyperosomotic Substance Transient edema may be prepared by topical injection of carrageenan, a hyperosmotic substance to pad of foot of mouse. Magnitude of the edema thus formed was evaluated by measuring the thickness of feet pad from time to time.

As a result, it was shown that the edema at lower limb increased in RAMP 2+/− mouse (FIG. 323)

Example 17

Investigation Using Cell Line with Stably Overexpressed RAMP 2

(1) Preparation of Cell Line with Stably Overexpressed RAMP 2

In this Example, a cell line with stably overexpressed RAMP 2 gene was prepared using EAhy 926, a cell line derived from the human umbilical vein endothelial cell by introducing RAMP 2 gene.

As a procedure, human RAMP 2 cDNA about 580 bp was inserted into the expression vector pcDNA 3.1. The expression vector (FIG. 34) was treated with restricted enzyme (Sal I) to convert to linear DNA, then transfected into EAhy 926 cell using Effectene, a transfection agent by QIAGEN.

Cell colony in which the gene was successfully transfected was screened by adding neomycin in culture fluid, then picking up the survived colony.

Figure 34:
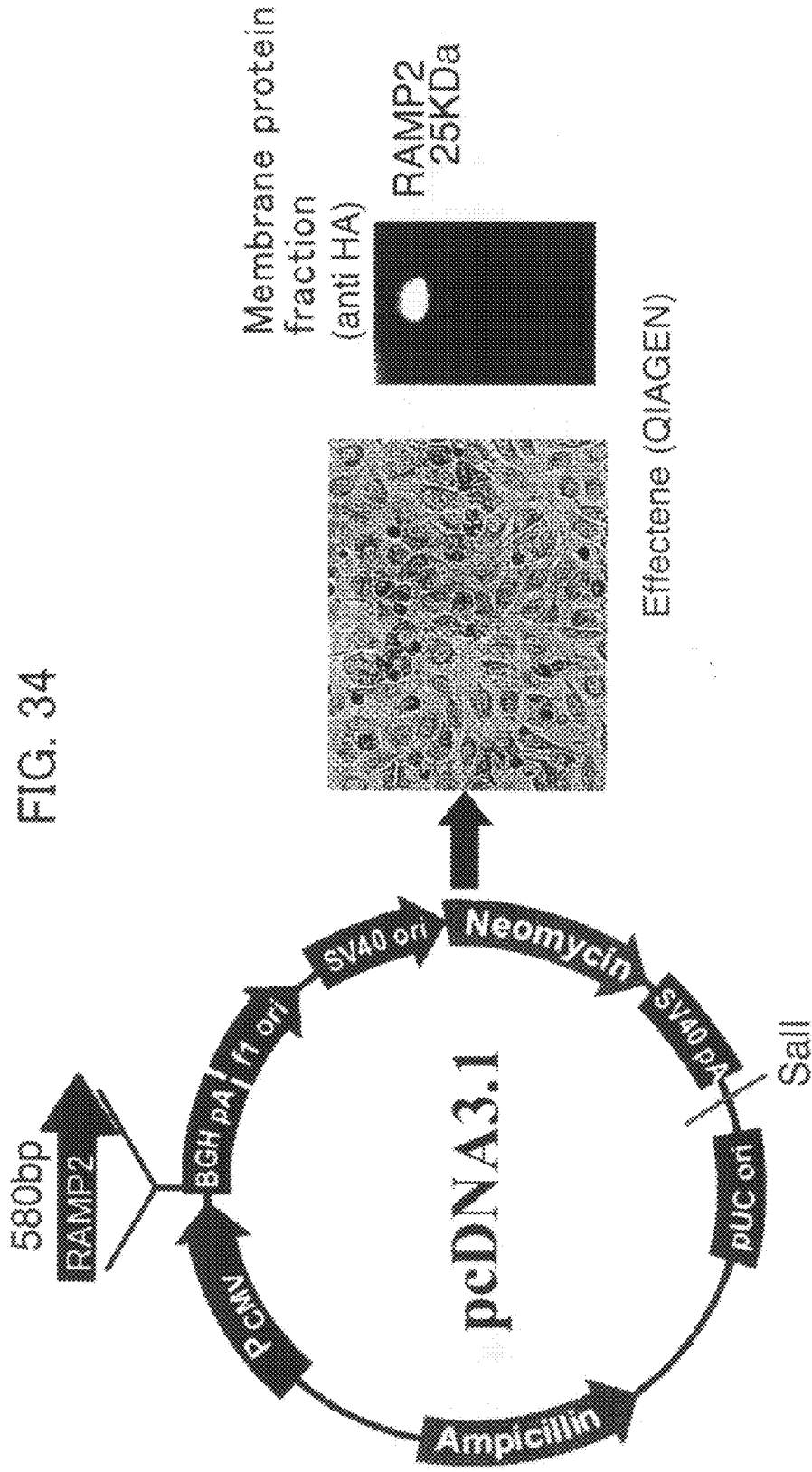
FIG. 34 shows the establishment of the cell line of endothelial cell in which RAMP 2 is stably overexpressed.

As a result, the cell with overexpressed RAMP 2 gene in about 1000 times in comparison with control cells was obtained (FIG. 34).

Proliferating potency, response to apoptotic stimulation, capillary formation ability were investigated as follows.

(2) Expression Level of RAMP 2, RAMP 3, AM and CRLR

The cells transfected with RAMP 2 gene and control cells transfected with control vector were cultured on normal plate or the plate coated with Matrigel.

RNA was extracted from these cultured cells and the expression levels of RAMP 2, RAMP 3, AM and CRLR were compared using real-time PCR technique.

As a result, overexpression of RAMP 2 was observed in both RAMP 2 transfected cells cultured on normal plate and Matrigel-coated plate.

Figure 35:
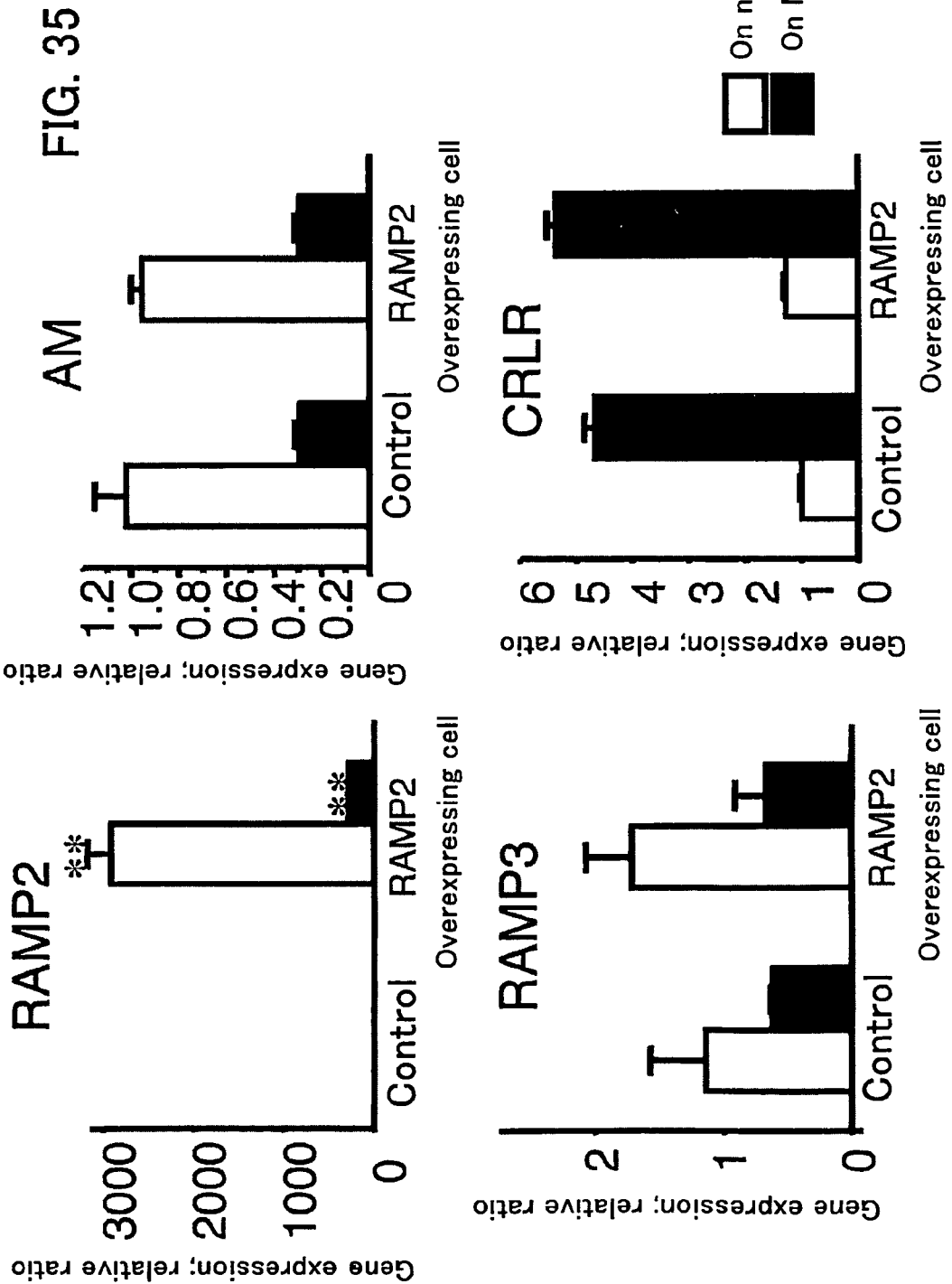
FIG. 35 shows the expression levels of CRLR, AM, RAMP 2 and RAMP 3 using the strain of endothelial cell in which RAMP 2 is overexpressed in comparison with control cells.

No significant difference was observed in the expression of RAMP 3, AM, and CRLR between control cells and RAMP 2 transfected cells (FIG. 35).

(3) Capillary Formation Ability of Cells with Overexpressed RAMP 2

When EAhy 926 cells are cultured on Matrigel-coated plate, the capillary structure was formed in Matrigel.

Comparison of capillary formation was made between RAMP 2 overexpressing cells and control cells shows that capillary formation ability significantly increases in RAMP 2 overexpressing cells (FIG. 36).

(4) Cell Proliferation and Survival Test

Proliferation potency of RAMP 2 overexpressing cells and control cells was compared by uptake of BrdU.

Figure 37:
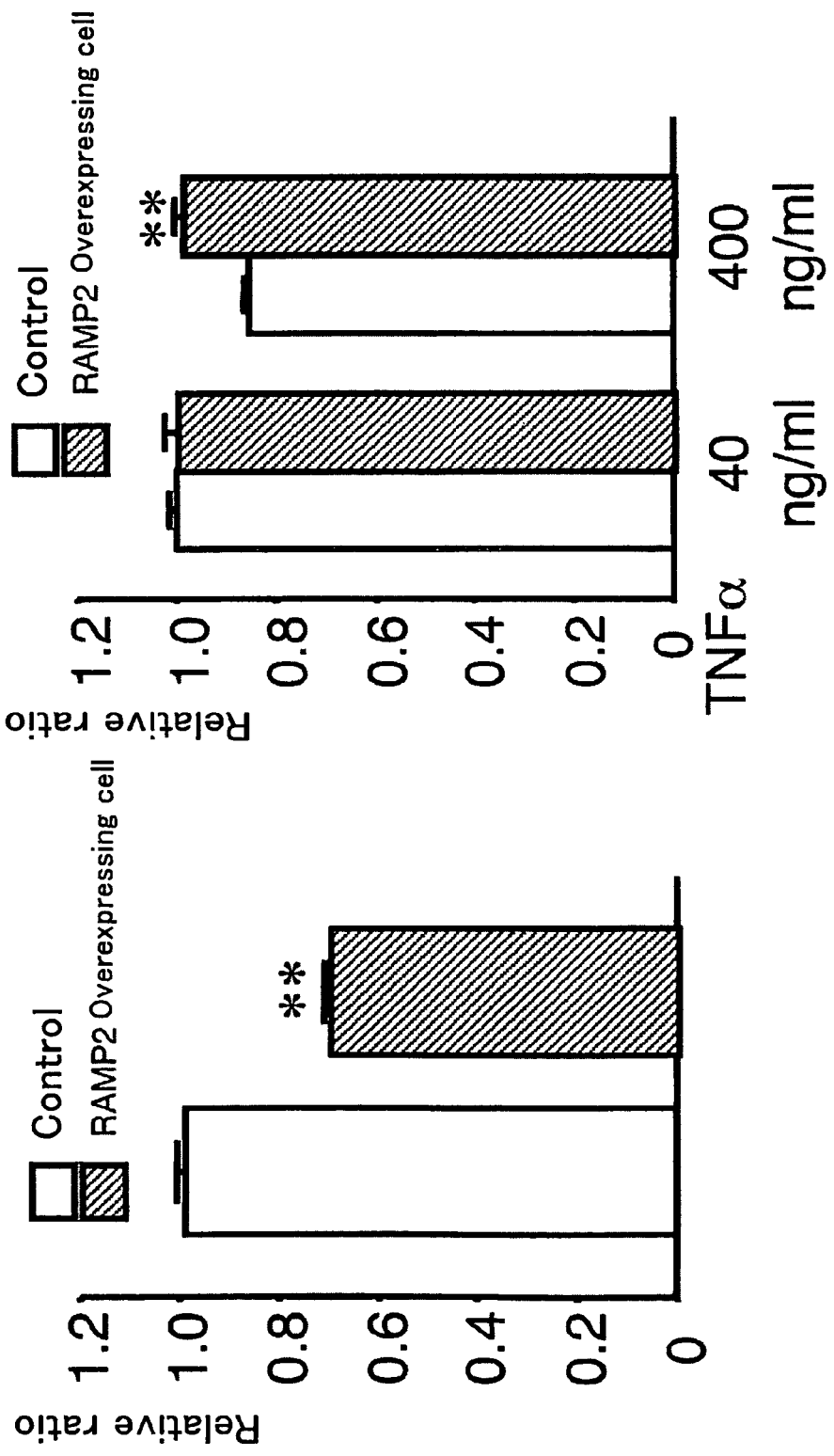
FIG. 37 shows the result of cell proliferation of RAMP 2 overexpressing cells in comparison with control cells using BrdU uptake assay and the result of cell survival of RAMP 2 overexpressing cells in comparison with control cells using WST-8 assay.

As a result, cell proliferation of RAMP 2 overexpressing cells rather decreased in comparison with control cells (FIG. 37, left panel).

On the other hand, number of cells survived after adding TNF α was measured using cell survival assay (WST-8 assay).

The result shows that the number of cell survived upon adding 400 ng/ml of TNF α in RAMP 2 overexpressing cell is significantly higher in comparison with control cells (FIG. 37, right panel).

(5) Apoptosis Induced by TNF α

Response to apoptosis induced by TNF α was investigated by quantifying the level of LDH (lactose dehydrogenase) leaked from the cell conducting apoptosis to the supernatant of culture fluid.

Expression of apoptosis-associated gene was investigated by treating the cells with TNF α, extracting RNA, followed by analysis using RT-PCR technique.

Figure 38:
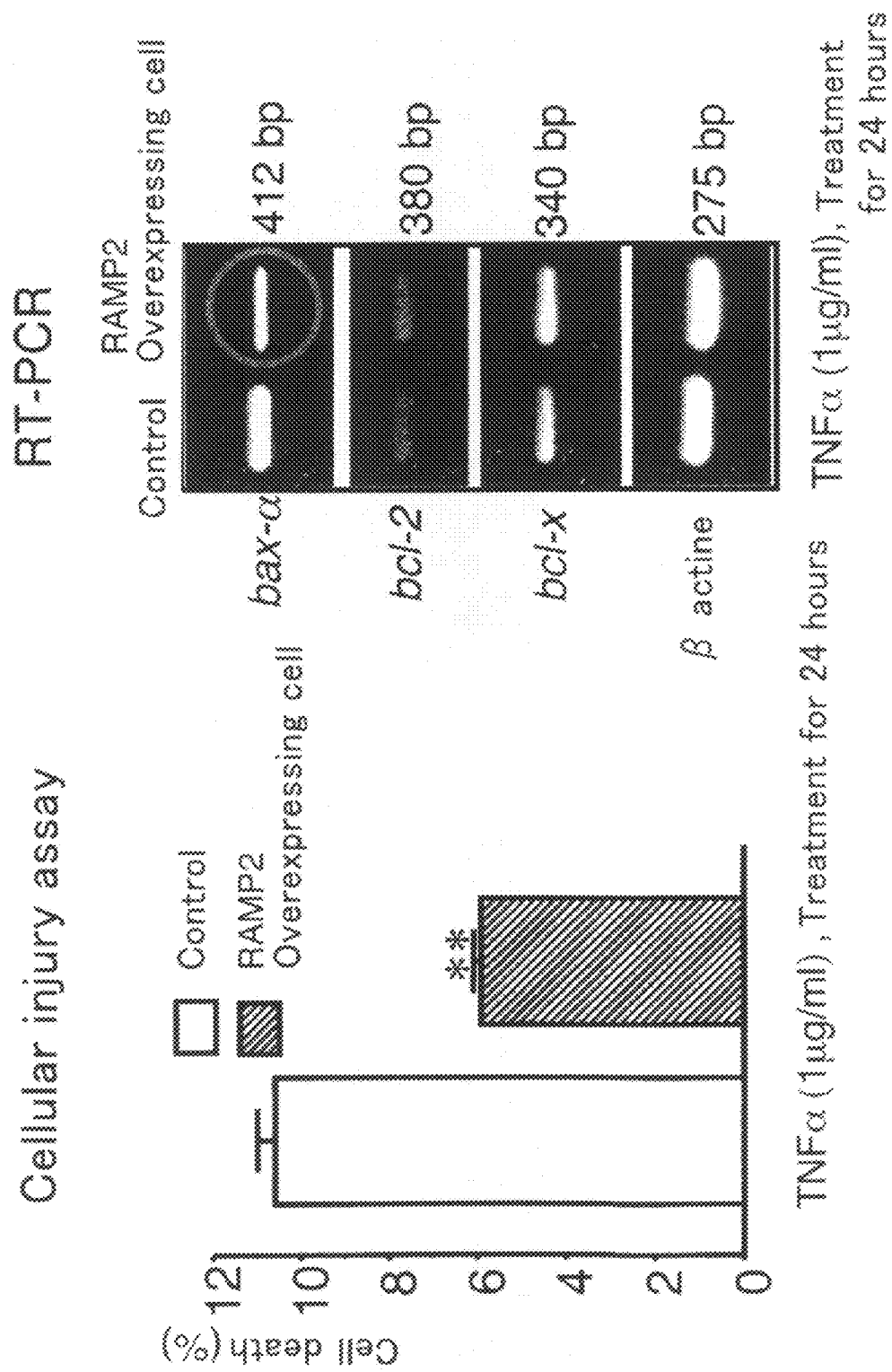
FIG. 38 shows the result of cell mortality and the expression of apoptosis-associated genes in the RAMP 2 overexpressing cells in comparison with control cells upon apoptogenic stimuli.

As a result, cell death by apoptosis decreased in RAMP 2 overexpressing cells (FIG. 38, left panel).

The expression of bax-α, a promoter of apoptosis decreased (FIG. 38, right panel).

From these results, it was shown that RAMP 2 overexpressing cells have resistance against apoptosis in comparison with control cells.

INDUSTRIAL APPLICABILITY

The present invention provides an angiogenesis agent including adrenomedullin as an active ingredient. The present invention also provides an angiogenic agent which contains, as the active ingredient, at least one substance selected from the group consisting of a substance inhibiting the activity of adrenomedullin degrading enzyme, an adrenomedullin receptor activity-modifying protein, a calcitonin receptor-like receptor and an adrenomedullin receptor.

AM stabilizes vascular structure and, moreover, has anti-arteriosclerotic effect. Therefore, the present invention is expected to provide a novel solution to the issues concerning the current angiogenesis therapy.

Moreover, AM has a unique effect of suppressing vascular permeability that is not observed in other angiogenesis enhancing factors. It is considered to be effective for the treatment of cerebral infarction, cerebral hemorrhage, cerebral edema, and the like.

The invention claimed is:

1. A method for screening a substance having an effect enhancing angiogenesis, comprising: administering a substance to a cell with reduced expression of endogenous RAMP 2 gene, wherein the substance is not adrenomedullin, measuring signal transduction within the cell, analyzing an effect of the substance on angiogenesis in the cell in vitro, and selecting the substance showing similar signal transduction to adrenomedullin by exhibiting enhanced angiogenesis.

2. The method of claim 1, wherein the cell is a RAMP 2 heterozygous knockout cell.

* * * * *